US011015184B2

(12) United States Patent
Huisman et al.

(10) Patent No.: US 11,015,184 B2
(45) Date of Patent: *May 25, 2021

(54) POLYNUCLEOTIDES ENCODING ENGINEERED TYROSINE AMMONIA LYASE VARIANTS

(71) Applicant: Codexis, Inc., Redwood City, CA (US)

(72) Inventors: Gjalt W. Huisman, Redwood City, CA (US); Nicholas J. Agard, San Francisco, CA (US); David Elgart, San Mateo, CA (US); Xiyun Zhang, Fremont, CA (US)

(73) Assignee: Codexis, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/689,503

(22) Filed: Nov. 20, 2019

(65) Prior Publication Data

US 2020/0071688 A1 Mar. 5, 2020

Related U.S. Application Data

(62) Division of application No. 16/367,640, filed on Mar. 28, 2019, now Pat. No. 10,533,168, which is a division of application No. 15/432,429, filed on Feb. 14, 2017, now Pat. No. 10,287,567, which is a division of application No. 14/688,126, filed on Apr. 16, 2015, now Pat. No. 9,605,252.

(60) Provisional application No. 61/980,167, filed on Apr. 16, 2014.

(51) Int. Cl.
*C12N 9/88* (2006.01)
*A61K 38/51* (2006.01)
*A61K 31/122* (2006.01)
*C12P 13/22* (2006.01)
*C12P 7/42* (2006.01)
*C12Q 1/527* (2006.01)

(52) U.S. Cl.
CPC ............. *C12N 9/88* (2013.01); *A61K 31/122* (2013.01); *A61K 38/51* (2013.01); *C12P 7/42* (2013.01); *C12P 13/225* (2013.01); *C12Q 1/527* (2013.01); *C12Y 403/01023* (2013.01)

(58) Field of Classification Search
None
See application file for complete search history.

(56) References Cited

U.S. PATENT DOCUMENTS

| 5,605,793 | A  | 2/1997  | Stemmer        |
|-----------|----|---------|----------------|
| 5,811,238 | A  | 9/1998  | Stemmer et al. |
| 5,830,721 | A  | 11/1998 | Stemmer et al. |
| 5,834,252 | A  | 11/1998 | Stemmer et al. |
| 5,837,458 | A  | 11/1998 | Minshull et al.|
| 5,928,905 | A  | 7/1999  | Stemmer et al. |
| 6,096,548 | A  | 8/2000  | Stemmer        |
| 6,117,679 | A  | 9/2000  | Stemmer        |
| 6,132,970 | A  | 10/2000 | Stemmer        |
| 6,165,793 | A  | 12/2000 | Stemmer        |
| 6,180,406 | B1 | 1/2001  | Stemmer        |
| 6,251,674 | B1 | 6/2001  | Tobin et al.   |
| 6,277,638 | B1 | 8/2001  | Stemmer        |
| 6,287,861 | B1 | 9/2001  | Stemmer et al. |
| 6,287,862 | B1 | 9/2001  | delCardayre et al. |
| 6,291,242 | B1 | 9/2001  | Stemmer        |
| 6,297,053 | B1 | 10/2001 | Stemmer        |
| 6,303,344 | B1 | 10/2001 | Patten et al.  |
| 6,309,883 | B1 | 10/2001 | Minshull et al.|
| 6,319,713 | B1 | 11/2001 | Patten et al.  |
| 6,319,714 | B1 | 11/2001 | Crameri et al. |
| 6,323,030 | B1 | 11/2001 | Stemmer        |
| 6,326,204 | B1 | 12/2001 | delCardayre et al. |
| 6,335,160 | B1 | 1/2002  | Patten et al.  |
| 6,335,198 | B1 | 1/2002  | delCardayre et al. |
| 6,344,356 | B1 | 2/2002  | Stemmer        |
| 6,352,859 | B1 | 3/2002  | delCardayre et al. |
| 6,355,484 | B1 | 3/2002  | Patten et al.  |
| 6,358,740 | B1 | 3/2002  | Patten et al.  |
| 6,358,742 | B1 | 3/2002  | Stemmer        |
| 6,365,377 | B1 | 4/2002  | Patten et al.  |
| 6,365,408 | B1 | 4/2002  | Stemmer        |
| 6,368,861 | B1 | 4/2002  | Crameri et al. |
| 6,372,497 | B1 | 4/2002  | Stemmer        |
| 6,376,246 | B1 | 4/2002  | Crameri et al. |

(Continued)

FOREIGN PATENT DOCUMENTS

WO 95/22625 A1 8/1995
WO 95/33836 A1 12/1995

(Continued)

OTHER PUBLICATIONS

Altschul, S.F., et al., "Gapped BLAST and PSI-BLAST: a new generation of protein database search programs," Nucleic Acids Res., 25(17):3389-3402 (1997).
Altschul, S., et al., "Basic local alignment search tool," J. Mol. Biol., 215: 403-410 (1990).
Beaucage, S.L., et al., "Deoxynucleoside phosphoamidites—A new class of key intermediates for deoxypolynucleotide synthesis," Tetrahedron Letters, 22(20):1859-62 (1981).
Bershtein, S., et al., "Protein Quality Control Acts on Folding Intermediates to Shape the Effects of Mutations on Organismal Fitness," Mol.Cell., 49:133-144 [2013].
Black, M.E., et al., "Creation of drug-specific herpes simplex virus type 1 thymidine kinase mutants for gene therapy," Proc Natl Acad Sci USA, 93:3525-3529 (1996).

(Continued)

Primary Examiner — Hope A Robinson
(74) Attorney, Agent, or Firm — Codexis, Inc.

(57) ABSTRACT

The present invention provides engineered tyrosine ammonia-lyase (TAL) polypeptides and compositions thereof. In some embodiments, the engineered TAL polypeptides have been optimized to provide enhanced catalytic activity while reducing sensitivity to proteolysis and increasing tolerance to acidic pH levels. The invention also provides methods for utilization of the compositions comprising the engineered TAL polypeptides for therapeutic and industrial purposes.

22 Claims, 1 Drawing Sheet
Specification includes a Sequence Listing.

(56) References Cited

U.S. PATENT DOCUMENTS

| | | |
|---|---|---|
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,531,341 B1 | 5/2009 | Vellard et al. |
| 7,534,564 B2 | 5/2009 | Patten et al. |
| 7,534,595 B2 | 5/2009 | Vellard et al. |
| 7,553,653 B2 | 6/2009 | Kakkis et al. |
| 7,560,263 B2 | 7/2009 | Kakkis et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 8,383,346 B2 | 2/2013 | Colbeck et al. |
| 9,605,252 B2 | 3/2017 | Huisman et al. |
| 10,287,567 B2 | 5/2019 | Huisman et al. |
| 10,533,168 B2 * | 1/2020 | Huisman ............. C12N 9/88 |
| 2008/0008695 A1 | 1/2008 | Vellard et al. |
| 2008/0220990 A1 | 9/2008 | Fox |
| 2009/0312196 A1 | 12/2009 | Colbeck et al. |
| 2010/0278802 A1 | 11/2010 | Kakkis et al. |
| 2012/0177722 A1 | 7/2012 | Weiner et al. |
| 2013/0005012 A1 | 1/2013 | Yu |
| 2013/0039898 A1 | 2/2013 | Okhamafe et al. |
| 2013/0340119 A1 | 12/2013 | Plesch et al. |
| 2017/0191050 A1 | 7/2017 | Huisman et al. |
| 2018/0016568 A1 | 1/2018 | Huisman et al. |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 00/42651 A1 | 7/2000 |
| WO | 01/75767 A2 | 10/2001 |
| WO | 2008/069958 A2 | 6/2008 |
| WO | 2009/152336 A1 | 12/2009 |
| WO | 2010/014225 A2 | 2/2010 |
| WO | 2010/144103 A1 | 12/2010 |
| WO | 2011/097335 A2 | 8/2011 |
| WO | 2014/172541 A2 | 10/2014 |

OTHER PUBLICATIONS

Botstein, D., et al., "Strategies and applications of in vitro mutagenesis," Science, 229(4719):1193-1201, 1985.

Caldwell, R.C., et al., "Mutagenic PCR," PCR Methods Appl., 3:S136-S140 (1994).

Carter, P., "Site-directed mutagenesis," Biochem. J., 237:1-7 (1986).

Christians, F.C., et al., "Directed evolution of thymidine kinase for AZT phosphorylation using DNA family shuffling," Nat. Biotechnol., 17:259-264 (1999).

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15(5):436-438 (1997).

Dale, S.J., et al., "Oligonucleotide-directed random mutagenesis using the phosphorothioate method," Methods Mol. Biol., 57:369-74 (1996).

De Boer, H.A., et al., "The tac promoter: A functional hybrid derived from the trp and lac promoters," Proc. Natl Acad. Sci. USA, 80:21-25 (1983).

Geetha, N.P., et al., "HPLC Method for Determination of p-coumaric acid from the Medicinal Herb Leptadinia reticulata," Int. J. Phytomed., 3:319-324 [2011].

Grompe, M., et al., "Loss of fumarylacetoacetate hydrolase is responsible for the neonatal hepatic dysfunction phenotype of lethal albino mice," Genes & Dev.,.7:2298-2307 [1993].

Guo, Z., et al., "3'-End-Forming Signals of Yeast mRNA," Mol. Cell. Biol., 15(11):5983-5990 [1995].

Hienikoff, S., et al., "Amino acid substitution matrices from protein blocks," Proc. Natl. Acad. Sci. USA, 89:10915-10919 [1992].

Ikeda, K., et al., "Phenylalanine ammonia-lyase modified with polyethylene glycol: potential therapeutic agent for phenylketonuria," Amino Acids, 29(3):283-287 [2005].

Kramer, B., et al., "Different base/base mismatches are corrected with different efficiencies by the methyl-directed DNA mismatch-repair system of E coli," Cell, 38(3):879-887, 1984.

Ling, M.M., et al., "Approaches to DNA Mutagenesis: An Overview," Anal. Biochem., 254(2):157-78 [1997].

Matthes, H.W.D., et al., "Simultaneous rapid chemical synthesis of over one hundred oligonucleotides on a microscale," EMBO J., 3(4):801-05 (1984).

Minshull, J., et al., "Protein evolution by molecular breeding," Curr. Op. Chem. Biol., 3(3):284-290 (1999).

Needleman, S., et al., "A general method applicable to the search for similarities in the amino acid sequence of two proteins," J. Mol. Biol. 48:443-453 (1970).

Overturf, K., et al., "Ex Vivo Heptatic Gene Therapy of a Mouse Model of Hereditary Tyrosinemia Type I," Hum. Gen. Ther., 9:295-304 [1998].

Pearson, W.R., "Improved tools for biological sequence comparison," Proc. Nat'l. Acad. Sci. USA, 85:2444-2448 (1988).

(56) References Cited

OTHER PUBLICATIONS

Romanos, M.A., et al., "Foreign gene expression in yeast: a review," Yeast 8:423-488 [1992].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Southwood, S., et al., "Several Common HLA-DR Types Share Largely Overlapping Peptide Binding Repertoires1,2," J. Immunol., 160:3363-3373 [1998].
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Tangri, S., et al., "Rationally Engineered Therapeutic Proteins with Reduced Immunogenicity," J. Immunol., 174:3187-3196 [2005].
Villa-Komaroff, L., et al., "A bacterial clone synthesizing proinsulin," Proc. Natl Acad. Sci. USA, 75:3727-3731 (1978).
Vita, R., et al., "The Immune Epitope Database 2.0," Nucl. Acids Res., 38:D854-62 [2010].
Watts, K.T., et al., "Discovery of a Substrate Selectivity Switchin Tyrosine Ammonia-Lyase, a Member of the Aromatic Amino Acid Lyase Family," Chem. Biol., 13:1317-26 [2006].
Wells, J.A., et al., "Cassette mutagenesis: an efficient method for generation of multiple mutations at defined sites," Gene, 34:315-323 (1985).
Zhang, J-H., et al., "Directed evolution of a fucosidase from a galactosidase by DNA shuffling and screening ," Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
NCBI Accession No. YP_001865631.1 dated Jun. 10, 2013.
NCBI Accession No. YP_007056096.1 dated Jun. 11, 2013.
NCBI Accession No. YP_007127054.1 dated Jun. 11, 2013.
NCBI Accession No. YP_324488.1 dated Jun. 10, 2013.
NCBI Accession No. ZP_07108482.1 dated Nov. 9, 2010.
Wang, L., et al., "Structural and Biochemical Characterization of the Therapeutic Anabaena variabilis Phenylalanine Ammonia Lyase," J.Mol.Bio., 380(4):623-635 [2008].
Jaliani, H.Z., et al., "Engineering and Kinetic Stabilization of the Therapeutic Enzyme Anabeana variabilis Phenylalanine Ammonia Lyase," Appl. Biochem. Biotech., 171(7):1805-1818 [2013].
Moffitt, M.C, et al., "Discovery of Two Cyanobacterial Phenylalanine Ammonia Lyases: Kinetic and Structural Characterization," Biochemistry, 46(4):1004-1012 [2007].
Kang, T.S., et al., "Converting an injectable protein therapeutic into an oral form: Phenylalanine ammonia lyase for phenylketonuria," Molecular Genetics and Metabolism, 99:4-9 [2010].
UniProt Accession No. Q3M5Z3 dated Jan. 22, 2014.
Louie, G.V., et al., "Structural Determinants and Modulation of Substrate Specificity in Phenylalanine-Tyrosine Ammonia-Lyases," Chemistry & Biology, 13:1327-1338 [2006].
Cooke, H.A., et al., "Structure and chemistry of 4-methylideneimidazole-5-one containing enzymes," Curr. Opinion Chem. Bio., 13(4):460-468 [2009].

\* cited by examiner

SEQUENCE LISTING

<160> NUMBER OF SEQ ID NOS: 17

<210> SEQ ID NO 1
<211> LENGTH: 7407
<212> TYPE: DNA
<213> ORGANISM: Anabaena variabilis

<400> SEQUENCE: 1

```
tctcatgttt gacagcttat catcgataag ctttaatgcg gtagtttatc acagttaaat    60
tgctaacgca gtcaggcacc gtgtatgaaa tctaacaatg cgctcatcgt catcctcggc   120
accgtcaccc tggatgctgt aggcataggc ttggttatgc cggtactgcc gggcctcttg   180
cgggatatcc ggatatagtt cctcctttca gcaaaaaacc cctcaagacc cgtttagagg   240
ccccaagggg ttatgctagt tattgctcag cggtggcagc agccaactca gcttcctttc   300
gggctttgtt agcagccgga tccttaatgc agacacggca gaatgtcctg aacggcctga   360
acaataacac caccggctgc aatatctgca ctaatacgtg caatatgttc atccagaccc   420
tgttcattat cattccaaat atacggacga tctgaggtcg gtttctgacc aacaacatga   480
cgaactgcgc tatacagacg ttcggttgcc ggtgacagac aggcacgtgc atcataatga   540
ccggtttttt tgtaggtacg cagatcaact gcctgaacac caaacatcag ggcaatggca   600
acataattct gaaaaatatc aacgctacga cgtgccaggg ttgcgctggt ataaccctgg   660
ctgttaatat tctggttaaa ctgttcggca tgggtcggaa acgatctgc aatactatta   720
ccataaaagg tcagcagcgg cataatgcta ttaccgcaaa tctgcagacc tttcagaccc   780
atattaactt tacgttcacg attacccagc agactcggag gcagaccatt gctaaattcc   840
ggtgatgcca gcagtgcaat ctgaacatcc agatgttttg ccagcagacc gatataatag   900
cgcagatgat ccatacccat accaacatac tgacccagaa aattaccacc atgatagctt   960
gcctgattat caacatcaat cagcgggtta tcggtaacgc tgttaatctc aatttcgatt  1020
tgtttggcaa tctggctaat accatcaaca atcggaccca gatactgcgg cagacaacgc  1080
aggctataac gatcctggat cagttcatga tcacgataat catgtttacc atccagttca  1140
tcacgaacca gctggctatt ggccagcagg ctaatcatct gatctgctgc ccacagctga  1200
cccggatgcg gtttgctgtt atggataaac ggatgaaagc tctgatttgt accattcagt  1260
gcctgaatat ccagtgcatg aacacccatt gcaattgcgg tcagaatctg gtatcataa   1320
acacaatttg ctgcaatacc ggtcataacg ctggtgccat tcatcattgc cagaccttct  1380
ttcggcagca gggtcagcgg actcagattc agctgacgca gtgcggtcgg tgcgtccatt  1440
tctttgccat taaatcaac tttaaagctc gggtccaggc caatcaggct accggtaata  1500
tagctcagcg gaaccagatc accgctggca ccaatgctac caaattcata acatacggg   1560
gtaacaccgg cattcagaaa gatttccatg cgtttaatca gttccagacg aataccgctt  1620
gcaccacgca tgtggctatt tgcacgcagc agcattgctg cacgaacatc tgccagcggc  1680
agtttattac ctgcaccggt tttcagaaac caaaccagat tggtctgcag ttcgcttgcc  1740
tgttcacggc taattgcaac atttgccata ccaccaaaac cgctggtaac accataaatc  1800
ggttcaccgc tttcaactgc attattgata taatcacagc tggcctgaat accctgcaga  1860
atatcggtat tattggtcag gctaaccagg gtgccattac gggcaacacg tgcaacatca  1920
ttgatggtca gtttctgatt accaataatc acatttgcgc tgctattgcc ggtaaagcta  1980
aactgctggc tgctggtttt gctctgtgcc tggctcaggg ttttcatatg acgaccttcg  2040
atatggccgc tgctgtgatg atgatgatga tgatgatgat gatggcccat ggtatatctc  2100
cttcttaaag ttaaacaaaa ttatttctag aggggaattg ttatccgctc acaattcccc  2160
tatagtgagt cgtattaatt tcgcgggatc gagatctcga tcctctacgc cggacgcatc  2220
gtggccggca tcaccggcgc cacaggtgcg gttgctggcg cctatatcgc cgacatcacc  2280
```

```
gatgggaag atcgggctcg ccacttcggg ctcatgagcg cttgtttcgg cgtgggtatg    2340
gtggcaggcc ccgtggccgg gggactgttg ggcgccatct ccttgcatgc accattcctt    2400
gcggcggcgg tgctcaacgg cctcaaccta ctactgggct gcttcctaat gcaggagtcg    2460
cataagggag agcgtcgaga tcccggacac catcgaatgg cgcaaaacct ttcgcggtat    2520
ggcatgatag cgcccggaag agagtcaatt cagggtggtg aatgtgaaac cagtaacgtt    2580
atacgatgtc gcagagtatg ccggtgtctc ttatcagacc gtttcccgcg tggtgaacca    2640
ggccagccac gtttctgcga aaacgcggga aaaagtggaa gcggcgatgg cggagctgaa    2700
ttacattccc aaccgcgtgg cacaacaact ggcgggcaaa cagtcgttgc tgattggcgt    2760
tgccacctcc agtctggccc tgcacgcgcc gtcgcaaatt gtcgcggcga ttaaatctcg    2820
cgccgatcaa ctgggtgcca gcgtggtggt gtcgatggta gaacgaagcg cgtcgaagc     2880 ctgtaaagcg gcggtgcaca atcttctcgc gcaacgcgtc agtgggctga tcattaacta    2940
tccgctggat gaccaggatg ccattgctgt ggaagctgcc tgcactaatg ttccggcgtt    3000
atttcttgat gtctctgacc agacacccat caacagtatt attttctccc atgaagacgg    3060
tacgcgactg ggcgtggagc atctggtcgc attgggtcac cagcaaatcg cgctgttagc    3120
gggcccatta agttctgtct cggcgcgtct gcgtctggct ggctggcata aatatctcac    3180
tcgcaatcaa attcagccga tagcggaacg ggaaggcgac tggagtgcca tgtccggttt    3240
tcaacaaacc atgcaaatgc tgaatgaggg catcgttccc actgcgatgc tggttgccaa    3300
cgatcagatg gcgctgggcg caatgcgcgc cattaccgag tccgggctgc gcgttggtgc    3360
ggatatctcg gtagtgggat acgacgtac cgaagacagc tcatgttata tcccgccgtt     3420
aaccaccatc aaacaggatt ttcgcctgct ggggcaaacc agcgtggacc gcttgctgca    3480
actctctcag ggccaggcgg tgaagggcaa tcagctgttg cccgtctcac tggtgaaaag    3540
aaaaaccacc ctggcgccca atacgcaaac cgcctctccc cgcgcgttgg ccgattcatt    3600
aatgcagctg gcacgacagg tttcccgact ggaaagcggg cagtgagcgc aacgcaatta    3660
atgtaagtta gctcactcat taggcaccgg gatctcgacc gatgcccttg agagccttca    3720
acccagtcag ctccttccgg tgggcgcggg gcatgactat cgtcgccgca cttatgactg    3780
tcttctttat catgcaactc gtaggacagg tgccggcagc gctctgggtc attttcggcg    3840
aggaccgctt tcgctggagc gcgacgatga tcggcctgtc gcttgcgta ttcggaatct      3900 tgcacgccct cgctcaagcc ttcgtcactg gtcccgccac caaacgtttc ggcgagaagc    3960
aggccattat cgccggcatg gcggccgacg cgctgggcta cgtcttgctg gcgttcgcga    4020
cgcgaggctg gatggccttc cccattatga ttcttctcgc ttccggcggc atcgggatgc    4080
ccgcgttgca ggccatgctg tccaggcagg tagatgacga ccatcaggga cagcttcaag    4140
gatcgctcgc ggctcttacc agcctaactt cgatcactgg accgctgatc gtcacggcga    4200
tttatgccgc ctcggcgagc acatggaacg ggttggcatg gattgtaggc gccgccctat    4260
accttgtctg cctccccgcg ttgcgtcgcg gtgcatggag ccgggccacc tcgacctgaa    4320
tggaagccgg cggcacctcg ctaacggatt caccactcca agaattggag ccaatcaatt    4380
cttgcggaga actgtgaatg cgcaaaccaa cccttggcag aacatatcca tcgcgtccgc    4440
catctccagc agccgcacgc ggcgcatctc gggcagcgtt gggtcctggc cacgggtgcg    4500
catgatcgtg ctcctgtcgt tgaggacccg gctaggctgg cggggttgcc ttactggtta    4560
gcagaatgaa tcaccgatac gcgagcgaac gtgaagcgac tgctgctgca aaacgtctgc    4620
gacctgagca acaacatgaa tggtcttcgg tttccgtgtt tcgtaaagtc tggaaacgcg    4680
```

```
gaagtcagcg ccctgcacca ttatgttccg gatctgcatc gcaggatgct gctggctacc    4740
ctgtggaaca cctacatctg tattaacgaa gcgctggcat tgaccctgag tgattttct     4800 ctggtcccgc cgcatccata ccgccagttg tttaccctca caacgttcca gtaaccgggc    4860
atgttcatca tcagtaaccc gtatcgtgag catcctctct cgtttcatcg gtatcattac    4920
ccccatgaac agaaatcccc cttacacgga ggcatcagtg accaaacagg aaaaaaccgc    4980
ccttaacatg gcccgcttta tcagaagcca gacattaacg cttctggaga aactcaacga    5040
gctggacgcg gatgaacagg cagacatctg tgaatcgctt cacgaccacg ctgatgagct    5100
ttaccgcagc tgcctcgcgc gtttcggtga tgacggtgaa aacctctgac acatgcagct    5160
cccggagacg gtcacagctt gtctgtaagc ggatgccggg agcagacaag cccgtcaggg    5220
cgcgtcagcg ggtgttggcg ggtgtcgggg cgcagccatg acccagtcac gtagcgatag    5280
cggagtgtat actggcttaa ctatgcggca tcagagcaga ttgtactgag agtgcaccat    5340
atatgcggtg tgaaataccg cacagatgcg taaggagaaa ataccgcatc aggcgctctt    5400
ccgcttcctc gctcactgac tcgctgcgct cggtcgttcg gctgcggcga gcggtatcag    5460
ctcactcaaa ggcggtaata cggttatcca cagaatcagg ggataacgca ggaaagaaca    5520
tgtgagcaaa aggccagcaa aaggccagga accgtaaaaa ggccgcgttg ctggcgtttt    5580
tccataggct ccgcccccct gacgagcatc acaaaaatcg acgctcaagt cagaggtggc    5640
gaaacccgac aggactataa agataccagg cgtttccccc tggaagctcc ctcgtgcgct    5700
ctcctgttcc gaccctgccg cttaccggat acctgtccgc ctttctccct tcgggaagcg    5760
tggcgctttc tcatagctca cgctgtaggt atctcagttc ggtgtaggtc gttcgctcca    5820
agctgggctg tgtgcacgaa ccccccgttc agcccgaccg ctgcgcctta tccggtaact    5880
atcgtcttga gtccaacccg gtaagacacg acttatcgcc actggcagca gccactggta    5940
acaggattag cagagcgagg tatgtaggcg gtgctacaga gttcttgaag tggtggccta    6000
actacggcta cactagaagg acagtatttg gtatctgcgc tctgctgaag ccagttacct    6060
tcggaaaaag agttggtagc tcttgatccg gcaaacaaac caccgctggt agcggtggtt    6120
tttttgtttg caagcagcag attacgcgca gaaaaaaagg atctcaagaa gatcctttga    6180
tcttttctac ggggtctgac gctcagtgga acgaaaactc acgttaaggg attttggtca    6240
tgagattatc aaaaaggatc ttcacctaga tccttttaaa ttaaaaatga agttttaaat    6300
caatctaaag tatatatgag taaacttggt ctgacagtta ccaatgctta atcagtgagg    6360
cacctatctc agcgatctgt ctatttcgtt catccatagt tgcctgactc cccgtcgtgt    6420
agataactac gatacgggag ggcttaccat ctggccccag tgctgcaatg ataccgcgag    6480
acccacgctc accggctcca gatttatcag caataaacca gccagccgga agggccgagc    6540
gcagaagtgg tcctgcaact ttatccgcct ccatccagtc tattaattgt tgccgggaag    6600
ctagagtaag tagttcgcca gttaatagtt tgcgcaacgt tgttgccatt gctgcaggca    6660
tcgtggtgtc acgctcgtcg tttggtatgg cttcattcag ctccggttcc caacgatcaa    6720
ggcgagttac atgatccccc atgttgtgca aaaaagcggt tagctccttc ggtcctccga    6780
tcgttgtcag aagtaagttg gccgcagtgt tatcactcat ggttatggca gcactgcata    6840
attctcttac tgtcatgcca tccgtaagat gcttttctgt gactggtgag tactcaacca    6900
agtcattctg agaatagtgt atgcggcgac cgagttgctc ttgcccggcg tcaacacggg    6960
ataataccgc gccacatagc agaactttaa aagtgctcat cattggaaaa cgttcttcgg    7020
```

```
ggcgaaaact ctcaaggatc ttaccgctgt tgagatccag ttcgatgtaa cccactcgtg      7080
cacccaactg atcttcagca tcttttactt tcaccagcgt ttctgggtga gcaaaaacag      7140
gaaggcaaaa tgccgcaaaa aagggaataa gggcgacacg gaaatgttga atactcatac      7200
tcttcctttt tcaatattat tgaagcattt atcagggtta ttgtctcatg agcggataca      7260
tatttgaatg tatttagaaa aataaacaaa taggggttcc gcgcacattt ccccgaaaag      7320
tgccacctga cgtctaagaa accattatta tcatgacatt aacctataaa aataggcgta      7380
tcacgaggcc ctttcgtctt caagaat                                          7407

<210> SEQ ID NO 2
<211> LENGTH: 1701
<212> TYPE: DNA
<213> ORGANISM: Anabaena variabilis

<400> SEQUENCE: 2
atgaaaaccc tgagccaggc acagagcaaa accagcagcc agcagtttag ctttaccggc        60
aatagcagcg caaatgtgat tattggtaat cagaaactga ccatcaatga tgttgcacgt       120
gttgcccgta atggcaccct ggttagcctg accaataata ccgatattct gcagggtatt       180
caggccagct gtgattatat caataatgca gttgaaagcg tgaaccgat ttatggtgtt        240 accagcggtt ttggtggtat ggcaaatgtt gcaattagcc gtgaacaggc aagcgaactg       300
cagaccaatc tggtttggtt tctgaaaacc ggtgcaggta taaactgcc gctggcagat       360 gttcgtgcag caatgctgct gcgtgcaaat agccacatgc gtggtgcaag cggtattcgt       420
ctggaactga ttaaacgcat ggaaatcttt ctgaatgccg tgttacccc gtatgtttat       480 gaatttggta gcattggtgc cagcggtgat ctggttccgc tgagctatat taccggtagc       540
ctgattggcc tggacccgag ctttaaagtt gattttaatg caaagaaat ggacgcaccg       600 accgcactgc gtcagctgaa tctgagtccg ctgaccctgc tgccgaaaga aggtctggca       660
atgatgaatg gcaccagcgt tatgaccggt attgcagcaa attgtgttta tgatacccag       720
attctgaccg caattgcaat gggtgttcat gcactggata ttcaggcact gaatggtaca       780
aatcagagct ttcatccgtt tatccataac agcaaaccgc atccgggtca gctgtgggca       840
gcagatcaga tgattagcct gctggccaat agccagctgg ttcgtgatga actggatggt       900
aaacatgatt atcgtgatca tgaactgatc caggatcgtt atagcctgcg ttgtctgccg       960
cagtatctgg gtccgattgt tgatggtatt agccagattg ccaaacaaat cgaaattgag      1020
attaacagcg ttaccgataa cccgctgatt gatgttgata tcaggcaag ctatcatggt       1080 ggtaattttc tgggtcagta tgttggtatg ggtatggatc atctgcgcta ttatatcggt      1140
ctgctggcaa acatctggga tgttcagatt gcactgctgg catcaccgga atttagcaat      1200
ggtctgcctc cgagtctgct gggtaatcgt gaacgtaaag ttaatatggg tctgaaaggt      1260
ctgcagattt gcggtaatag cattatgccg ctgctgacct tttatggtaa tagtattgca      1320
gatcgttttc cgacccatgc cgaacagttt aaccagaata ttaacagcca gggttatacc      1380
agcgcaaccc tggcacgtcg tagcgttgat atttttcaga attatgttgc cattgccctg      1440
atgtttggtg ttcaggcagt tgatctgcgt acctacaaaa aaaccggtca ttatgatgca      1500
cgtgcctgtc tgtcaccggc aaccgaacgt ctgtatagcg cagttcgtca tgttgttggt      1560
cagaaaccga cctcagatcg tccgtatatt tggaatgata tgaacaggg tctggatgaa      1620 catattgcac gtattagtgc agatattgca gccggtggtg ttattgttca ggccgttcag      1680
gacattctgc cgtgtctgca t                                                1701
```

<210> SEQ ID NO 3
<211> LENGTH: 1701
<212> TYPE: DNA
<213> ORGANISM: Anabaena variabilis

<400> SEQUENCE: 3

```
atgaaaaccc tgagccaggc acagagcaaa accagcagcc agcagtttag ctttaccggc      60
aatagcagcg caaatgtgat tattggtaat cagaaactga ccatcaatga tgttgcacgt     120
gttgcccgta atggcaccct ggttagcctg accaataata ccgatattct gcagggtatt     180
caggccagct gtgattatat caataatgca gttgaaagcg tgaaccgat ttatggtgtt      240
accagcggtt ttggtggtat ggcaaatgtt gcaattagcc gtgaacaggc aagcgaactg     300
cagaccaatc tggtttggtt tctgaaaacc ggtgcaggta taaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttacccc gtatgtttat      480
gaatttggta gcattggtgc agcggtgat ctggttccgc tgagctatat accggtagc      540
ctgattggcc tggaccccgag ctttaaagtt gattttaatg caaagaaat ggacgcaccg     600
accgcactgc gtcagctgaa tctgagtccg ctgaccctgc tgccgaaaga aggtctggca     660
atgatgaatg caccagcgt tatgaccggt attgcagcaa attgtgttta tgatacccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccaat agccagctgg ttcgtgatga actggatggt     900
aaacatgatt atcgtgatca tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080
ggtaattttc tgggtcagta tgttggtatg ggtatggatc atctgcgcta ttatatcggt    1140
ctgctggcaa acatctgga tgttcagatt gcactgctgg catcaccgga atttagcaat    1200
ggtctgcctc cgagtctgct gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat atttttcaga attatgttgc cattgccctg    1440
atgtttggtg ttcaggcagt tgatctgcgt acctacaaaa aaccggtca ttatgatgca    1500
cgtgcctgtc tgtcaccggc aaccgaacgt ctgtatagcg cagttcgtca tgttgttggt    1560
cagaaaccga cctcagatcg tccgtatatt tggaatgata tgaacaggg tctggatgaa    1620
catattgcac gtattagtgc agatattgca gccggtggtg ttattgttca ggccgttcag    1680
gacattctgc cgtgtctgca t                                              1701
```

<210> SEQ ID NO 4
<211> LENGTH: 567
<212> TYPE: PRT
<213> ORGANISM: Anabaena variabilis

<400> SEQUENCE: 4

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
```

-continued

```
             20                  25                  30
Leu Thr Ile Asn Asp Val Ala Arg Val Ala Arg Asn Gly Thr Leu Val
         35                  40                  45
Ser Leu Thr Asn Asn Thr Asp Ile Leu Gln Gly Ile Gln Ala Ser Cys
     50                  55                  60
Asp Tyr Ile Asn Asn Ala Val Glu Ser Gly Glu Pro Ile Tyr Gly Val
 65                  70                  75                  80
Thr Ser Gly Phe Gly Gly Met Ala Asn Val Ala Ile Ser Arg Glu Gln
                 85                  90                  95
Ala Ser Glu Leu Gln Thr Asn Leu Val Trp Phe Leu Lys Thr Gly Ala
             100                 105                 110
Gly Asn Lys Leu Pro Leu Ala Asp Val Arg Ala Ala Met Leu Leu Arg
         115                 120                 125
Ala Asn Ser His Met Arg Gly Ala Ser Gly Ile Arg Leu Glu Leu Ile
     130                 135                 140
Lys Arg Met Glu Ile Phe Leu Asn Ala Gly Val Thr Pro Tyr Val Tyr
145                 150                 155                 160
Glu Phe Gly Ser Ile Gly Ala Ser Gly Asp Leu Val Pro Leu Ser Tyr
                 165                 170                 175
Ile Thr Gly Ser Leu Ile Gly Leu Asp Pro Ser Phe Lys Val Asp Phe
             180                 185                 190
Asn Gly Lys Glu Met Asp Ala Pro Thr Ala Leu Arg Gln Leu Asn Leu
         195                 200                 205
Ser Pro Leu Thr Leu Leu Pro Lys Glu Gly Leu Ala Met Met Asn Gly
     210                 215                 220
Thr Ser Val Met Thr Gly Ile Ala Ala Asn Cys Val Tyr Asp Thr Gln
225                 230                 235                 240
Ile Leu Thr Ala Ile Ala Met Gly Val His Ala Leu Asp Ile Gln Ala
                 245                 250                 255
Leu Asn Gly Thr Asn Gln Ser Phe His Pro Phe Ile His Asn Ser Lys
             260                 265                 270
Pro His Pro Gly Gln Leu Trp Ala Ala Asp Gln Met Ile Ser Leu Leu
         275                 280                 285
Ala Asn Ser Gln Leu Val Arg Asp Glu Leu Asp Gly Lys His Asp Tyr
     290                 295                 300
Arg Asp His Glu Leu Ile Gln Asp Arg Tyr Ser Leu Arg Cys Leu Pro
305                 310                 315                 320
Gln Tyr Leu Gly Pro Ile Val Asp Gly Ile Ser Gln Ile Ala Lys Gln
                 325                 330                 335
Ile Glu Ile Glu Ile Asn Ser Val Thr Asp Asn Pro Leu Ile Asp Val
             340                 345                 350
Asp Asn Gln Ala Ser Tyr His Gly Gly Asn Phe Leu Gly Gln Tyr Val
         355                 360                 365
Gly Met Gly Met Asp His Leu Arg Tyr Tyr Ile Gly Leu Leu Ala Lys
     370                 375                 380
His Leu Asp Val Gln Ile Ala Leu Leu Ala Ser Pro Glu Phe Ser Asn
385                 390                 395                 400
Gly Leu Pro Pro Ser Leu Leu Gly Asn Arg Glu Arg Lys Val Asn Met
                 405                 410                 415
Gly Leu Lys Gly Leu Gln Ile Cys Gly Asn Ser Ile Met Pro Leu Leu
             420                 425                 430
Thr Phe Tyr Gly Asn Ser Ile Ala Asp Arg Phe Pro Thr His Ala Glu
         435                 440                 445
```

```
Gln Phe Asn Gln Asn Ile Asn Ser Gln Gly Tyr Thr Ser Ala Thr Leu
        450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 5
<211> LENGTH: 1701
<212> TYPE: DNA
<213> ORGANISM: Anabaena variabilis

<400> SEQUENCE: 5
atgaaaaccc tgagtcaggc acagagcaaa accagcagcc agcagtttag ctttaccggc        60
aatagcagcg caaatgtgat tattggtaat cagaaactga ccatcaatga tgttgtacgt       120
gttgcccgta atggcaccct ggttagcctg accaataata ccgatattct gcagggtatt       180
caggccagct gtgattatat caataatgca gttgaaagcg gtgaaccgat ttatggtgtt       240
accagcggtt ttggtggtat ggcaaatgtt gtaattagcc gtgaacaggc aagcgaactg       300
cagaccaatc tggtttggtt tctgaaaacc ggtgcaggta taaactgcc gctggcagat       360 gttcgtgcag caatgctgct gcgtgcaaat agccacatgc gtggtgcaag cggtattcgt       420
ctggaactga ttaaacgcat ggaaatcttt ctgaatgccg tgttaccccc gtatgtttat       480
gaatttggta gcattggtgc cagcggtgat ctggttccgc tgagctatat taccggtagc       540
ctgattggcc tggacccgag cttaaagtt gattaatg caaagaaat ggacgcaccg       600 accgcactgc gtcagctgaa tctgagtccg ctgaccctgc tgccgaaaga aggtctggca       660
atgatgaatg gcaccagcgt tatgaccggt attgcagcaa attgtgttta tgatacccag       720
attctgaccg caattgcaat gggtgttcat gcactggata ttcaggcact gaatggtaca       780
aatcagagct ttcatccgt tatccataac agcaaaccgc atccgggtca gctgtgggca       840
gcagatcaga tgattagcct gctggccggt agccagctgg ttcgtgatga actggatggt       900
aaacatgatt atcgtgatgg tgaactgatc caggatcgtt atagcctgcg ttgtctgccg       960
cagtatctgg gtccgattgt tgatggtatt agccagattg ccaaacaaat cgaaattgag      1020
attaacagcg ttaccgataa cccgctgatt gatgttgata tcaggcaag ctatcatggt      1080 ggtaatttc tgggtcagta tgttggtatg ggtatggatc atctgcgcta ttatatcggt      1140
ctgctggcaa acatctggga tgttcagatt gcactgctgg catcaccgga atttagcaat      1200
ggtctgcctc cgagtctggt gggtaatcgt gaacgtaaag ttaatatggg tctgaaaggt      1260
ctgcagattt gcggtaatag cattatgccg ctgctgacct tttatggtaa tagtattgca      1320
gatcgttttc cgacccatgc cgaacagttt aaccagaata ttaacagcca gggttatacc      1380
```

-continued

```
agcgcaaccc tggcacgtcg tagcgttgat attttcaga attatgttgc cattgccctg    1440
atgtttggtg ttcaggcagt tgatctgcgt acctacaaaa aaaccggtca ttatgatgca    1500
cgtgcctgtc tgtcaccggc aaccgaacgt ctgtatagcg cagttcgtca tgttgttggt    1560
cagaaaccga gctcagatcg tccgtatatt tggaatgata atgaacaggg tctggatgaa    1620
catattgcac gtattagtgc agatattgca gccggtggtg ttattgttca ggccgttcag    1680
gacattctgc cgtgtctgca t                                              1701
```

<210> SEQ ID NO 6
<211> LENGTH: 567
<212> TYPE: PRT
<213> ORGANISM: Anabaena variabilis

<400> SEQUENCE: 6

```
Met Lys Thr Leu Ser Gln Ala Gln Ser Lys Thr Ser Gln Gln Phe
1               5                  10                  15

Ser Phe Thr Gly Asn Ser Ala Asn Val Ile Ile Gly Asn Gln Lys
            20                  25                  30

Leu Thr Ile Asn Asp Val Val Arg Val Ala Arg Asn Gly Thr Leu Val
            35                  40                  45

Ser Leu Thr Asn Asn Thr Asp Ile Leu Gln Gly Ile Gln Ala Ser Cys
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Arg Asp Gly Glu Leu Ile Gln Asp Arg Tyr Ser Leu Arg Cys Leu Pro
305                 310                 315                 320
```

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 7
<211> LENGTH: 1701
<212> TYPE: DNA
<213> ORGANISM: Anabaena variabilis

<400> SEQUENCE: 7
atgaaaaccc tgagccaggc acagagcaaa accagcagcc agcagtttag ctttaccggc        60
aatagcagcg caaatgtgat tattggtaat cagaaactga ccatcaatga tgttgcacgt       120
gttgcccgta atggcaccct ggttagcctg accaataata ccgatattct gcagggtatt       180
caggccagct gtgattatat caataatgca gttgaaagcg tgaaccgat ttatggtgtt        240 accagcggtt ttggtggtat ggcaaatgtt gcaattagcc gtgaacaggc aagcgaactg       300
cagaccaatc tggtttggca cctgaaaacc ggtgcaggta taaaactgcc gctggcagat       360
gttcgtgcag caatgctgct gcgtgcaaat agccacatgc gtggtgcaag cggtattcgt       420
ctggaactga ttaaacgcat ggaaatcttt ctgaatgccg tgttacccc gtatgtttat        480 gaatttggta gcattggtgc cagcggtgat ctggttccgc tgagctatat taccggtagc       540
ctgattggcc tggaccccag ctttaaagtt gattttaatg caaagaaat ggacgcaccg        600 accgcactgc gtcagctgaa tctgagtccg ctgaccctgc tgccgaaaga aggtctggca       660

```
atgatgaatg gcaccagcgt tatgaccggt attgcagcaa attgtgttta tgatacccag    720
attctgaccg caattgcaat gggtgttcat gcactggata ttcaggcact gaatggtaca    780
aatcagagct ttcatccgtt tatccataac agcaaaccgc atccgggtca gctgtgggca    840
gcagatcaga tgattagcct gctggccaat agccagctgg ttcgtgatga actggatggt    900
aaacatgatt atcgtgatca tgaactgatc caggatcgtt atagcctgcg ttgtctgccg    960
cagtatctgg gtccgattgt tgatggtatt agccagattg ccaaacaaat cgaaattgag   1020
attaacagcg ttaccgataa cccgctgatt gatgttgata atcaggcaag ctatcatggt   1080
ggtaatttc tgggtcagta tgttggtatg ggtatggatc atctgcgcta ttatatcggt   1140
ctgctggcaa aacatctgga tgttcagatt gcactgctgg catcaccgga atttagcaat   1200
ggtctgcctc cgagtctgct gggtaatcgt gaacgtaaag ttaatatggg tctgaaaggt   1260
ctgcagattt gcggtaatag cattatgccg ctgctgacct tttatggtaa tagtattgca   1320
gatcgttttc cgacccatgc cgaacagttt aaccagaata ttaacagcca gggttatacc   1380
agcgcaaccc tggcacgtcg tagcgttgat attttcaga attatgttgc cattgccctg   1440
atgtttggtg ttcaggcagt tgatctgcgt acctacaaaa aaaccggtca ttatgatgca   1500
cgtgcctgtc tgtcaccggc aaccgaacgt ctgtatagcg cagttcgtca tgttgttggt   1560
cagaaaccga cctcagatcg tccgtatatt tggaatgata atgaacaggg tctggatgaa   1620
catattgcac gtattagtgc agatattgca gccggtggtg ttattgttca ggccgttcag   1680
gacattctgc cgtgtctgca t                                              1701
```

<210> SEQ ID NO 8
<211> LENGTH: 567
<212> TYPE: PRT
<213> ORGANISM: Anabaena variabilis

<400> SEQUENCE: 8

```
Met Lys Thr Leu Ser Gln Ala Gln Ser Lys Thr Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Cys
        50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp His Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190
```

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 9
<211> LENGTH: 1701
<212> TYPE: DNA
<213> ORGANISM: Anabaena variabilis

<400> SEQUENCE: 9

```
atgaaaaccc tgagtcaggc acagagcaaa accagcagcc agcagtttag ctttaccggc      60
aatagcagcg caaatgtgat tattggtaat cagaaactga ccatcaatga tgttgtacgt     120
gttgcccgta atggcaccct ggttagcctg accaataata ccgatattct gcagggtatt     180
caggccagct gtgattatat caataatgca gttgaaagcg gtgaaccgat ttatggtgtt     240
accagcggtt ttggtggtat ggcaaatgtt gtaattagcc gtaacaggc aagcgaactg     300
cagaccaatc tggtttggca cctgaaaacc ggtgcaggta taaaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttaccccc gtatgtttat     480
gaatttggta gcattggtgc cagcggtgat ctggttccgc tgagctatat taccggtagc     540
ctgattggcc tggacccgag ctttaaagtt gattttaatg caaagaaat ggacgcaccg     600
accgcactgc gtcagctgaa tctgagtccg ctgaccctgc tgccgaaaga aggtctggca     660
atgatgaatg gcaccagcgt tatgaccggt attgcagcaa attgtgttta tgatacccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccggt agccagctgg ttcgtgatga actggatggt     900
aaacatgatt atcgtgatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080
ggtaatttc tgggtcagta tgttggtatg gtatggatc atctgcgcta ttatatcggt    1140
ctgctggcaa acatctgga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat atttttcaga attatgttgc cattgccctg    1440
atgtttggtg ttcaggcagt tgatctgcgt acctacaaaa aaaccggtca ttatgatgca    1500
cgtgcctgtc tgtcaccggc aaccgaacgt ctgtatagcg cagttcgtca tgttgttggt    1560
cagaaaccga gctcagatcg tccgtatatt tggaatgata tgaacaggg tctggatgaa    1620
catattgcac gtattagtgc agatattgca gccggtggtg ttattgttca ggccgttcag    1680
gacattctgc cgtgtctgca t                                              1701
```

<210> SEQ ID NO 10
<211> LENGTH: 567
<212> TYPE: PRT
<213> ORGANISM: Anabaena variabilis

<400> SEQUENCE: 10

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60
```

```
Asp Tyr Ile Asn Asn Ala Val Glu Ser Gly Glu Pro Ile Tyr Gly Val
 65                  70                  75                  80

Thr Ser Gly Phe Gly Gly Met Ala Asn Val Val Ile Ser Arg Glu Gln
                 85                  90                  95

Ala Ser Glu Leu Gln Thr Asn Leu Val Trp His Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
450                 455                 460

Ala Arg Arg Ser Val Asp Ile Phe Gln Asn Tyr Val Ala Ile Ala Leu
465                 470                 475                 480
```

```
Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 11
<211> LENGTH: 1701
<212> TYPE: DNA
<213> ORGANISM: Anabaena variabilis

<400> SEQUENCE: 11
atgaaaaccc tgagtcaggc acagagcaaa accagcagcc agcagtttag ctttaccggc      60
aatagcagcg caaatgtgat tattggtaat cagaaactga ccatcaatga tgttgtacgt     120
gttgcccgta atggcaccct ggttagcctg accaataata ccgatattct gcagggtatt     180
caggccagct gtgattatat caataatgca gttgaaagcg tgaaccgat gtatggtgtt      240 accagcggtt ttggtggtat ggcaaatgtt gtaattagcc gtgaacaggc aagcgaactg     300
cagaccaatc tggtttggca cctgaaaacc ggtgcaggta taaactgcc gctggcagat     360 gttcgtgcag caatgctgct gcgtgcaaat agccacatgc gtggtgcaag cggtattcgt     420
ctggaactga ttaaacgcat ggaaatcttt ctgaatgccg tgttacccc gtatgtttat     480 gaatttggta gcattggtgc cagcggtgat ctggttccgc tgagctatat accggtagc     540 ctgattggcc tggaccccgag ctttaaagtt gattttaatg caaagaaat ggacgcaccg     600 accgcactgc gtcagctgaa tctgagtccg ctgaccctgc tgccgaaaga aggtctggca     660
atgatgaatg gcaccagcgt tatgaccggt attgcagcaa attgtgttta tgataccag     720 attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccggt agccagctgg ttcgtgatga actggatggt     900
aaacatgatt atcgtgatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080 ggtaattttc tgggtcagta tgttggtatg ggtatggatc atctgcgcta ttatatcggt    1140
ctgctggcaa acatctgga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat atttttcaga attatgttgc cattgccctg    1440
atgtttggtg ttcaggcagt tgatctgcgc acctacaaaa aaaccggtca ttatgatgca    1500
cgtgcctgtc tgtcaccggc aaccgaacgt ctgtatagcg cagttcgtca tgttgttggt    1560
cagaaaccga gctcagatcg tccgtatatt tggaatgata atgaacaggg tctggatgaa    1620
```

```
catattgcac gtattagtgc agatattgca gccggtggtg ttattgttca ggccgttcag    1680
gacattctgc cgtgtctgca t                                              1701
```

<210> SEQ ID NO 12
<211> LENGTH: 567
<212> TYPE: PRT
<213> ORGANISM: Anabaena variabilis

<400> SEQUENCE: 12

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Met Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp His Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350
```

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 13
<211> LENGTH: 1701
<212> TYPE: DNA
<213> ORGANISM: Anabaena variabilis

<400> SEQUENCE: 13
atgaaaaccc tgagtcaggc acagagcaaa accagcagcc agcagtttag ctttaccggc    60
aatagcagcg caaatgtgat tattggtaat cagaaactga ccatcaatga tgttgtacgt   120
gttgcccgta atggcaccct ggttagcctg accaataata ccgatattct gcagggtatt   180
caggccagct gtgattatat caataatgca gttgaaagcg tgaaccgat gtatggtgtt   240 accagcggtt ttggtggtat ggcaaatgtt gtaattagcc gtgaacaggc cagcgaactg   300
cagaccaatc tggtttggca cctgaaaacc ggtgcaggta taaaactgcc gctggcagat   360
gttcgtgcag caatgctgct gcgtgcaaat agccacatgc gtggtgcaag cggtattcgt   420
ctggaactga ttaaacgcat ggaaatctttc tgaatgccg tgttacccc gtatgtttat   480 gaatttggta gcattggtgc cagcggtgat ctggttccgc tgagctatat taccggtagc   540
ctgattggcc tggacccgag ctttaaagtt gattttaatg caaagaaat ggacgcaccg   600 accgcactgc gtcagctgaa tctgagtccg ctgaccctgc tgccgaaaga aggtctggca   660
atgatgaatg gcaccagcgt tatgaccggt attgcagcaa ttgtgtttta tgatacccag   720
attctgaccg caattgcaat gggtgttcat gcactggata ttcaggcact gaatggtaca   780
aatcagagct ttcatccgtt tatccataac agcaaaccgc atccgggtca gctgtgggca   840
gcagatcaga tgattagcct gctggccggt agccagctgg ttcgtgatga actggatggt   900

```
aaacatgatt atcgtgatgg tgaactgatc caggatcgtt atgcgctgcg ttgtctgccg    960
cagtatctgg gtccgattgt tgatggtatt agccagattg ccaaacaaat cgaaattgag   1020
attaacagcg ttaccgataa cccgctgatt gatgttgata atcaggcaag ctatcatggt   1080
ggtaatttta tgggtcagta tgttggtatg ggtatggatc atctgcgcta ttatatcggt   1140
ctgctggcaa aacatctgga tgttaccatt gcactgctgg catcaccgga atttagcatg   1200
ggtctgcctc cgagtctggt gggtaatcgt gaacgtaaag ttaatatggg tctgaaaggt   1260
ctgcagattt gcggtaatag cattatgccg ctgctgacct tttatggtaa tagtattgca   1320
gatcgttttc cgacccatgc cgaacagttt aaccagtgca ttaacagcca gggttatacc   1380
agcgcaaccc tggcacgtcg tagcgttgat atttttcaga attatgttgc cattgccctg   1440
atgtttggtg ttcaggcagt tgatctgagg acctacaaaa aaaccggtca ttatgatgca   1500
cgtgcctgtc tgtcaccggc aaccgaacgt ctgtatagcg cagttcgtca tgttgttggt   1560
cagaaaccga gctcagatcg tccgtatatt tggaatgata atgaacaggg tctggatgaa   1620
catattgcac gtattagtgc agatattgca gccggtggtg ttattgttca ggccgttcag   1680
gacattctgc cgtgtctgca t                                             1701
```

<210> SEQ ID NO 14
<211> LENGTH: 567
<212> TYPE: PRT
<213> ORGANISM: Anabaena variabilis

<400> SEQUENCE: 14

```
Met Lys Thr Leu Ser Gln Ala Gln Ser Lys Thr Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Val Arg Val Ala Arg Asn Gly Thr Leu Val
            35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Met Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp His Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220
```

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
            245                 250                 255

Leu Asn Gly Thr Asn Gln Ser Phe His Pro Phe Ile His Asn Ser Lys
        260                 265                 270

Pro His Pro Gly Gln Leu Trp Ala Ala Asp Gln Met Ile Ser Leu Leu
    275                 280                 285

Ala Gly Ser Gln Leu Val Arg Asp Glu Leu Asp Gly Lys His Asp Tyr
290                 295                 300

Arg Asp Gly Glu Leu Ile Gln Asp Arg Tyr Ala Leu Arg Cys Leu Pro
305                 310                 315                 320

Gln Tyr Leu Gly Pro Ile Val Asp Gly Ile Ser Gln Ile Ala Lys Gln
            325                 330                 335

Ile Glu Ile Glu Ile Asn Ser Val Thr Asp Asn Pro Leu Ile Asp Val
        340                 345                 350

Asp Asn Gln Ala Ser Tyr His Gly Gly Asn Phe Met Gly Gln Tyr Val
    355                 360                 365

Gly Met Gly Met Asp His Leu Arg Tyr Tyr Ile Gly Leu Leu Ala Lys
370                 375                 380

His Leu Asp Val Thr Ile Ala Leu Leu Ala Ser Pro Glu Phe Ser Met
385                 390                 395                 400

Gly Leu Pro Pro Ser Leu Val Gly Asn Arg Glu Arg Lys Val Asn Met
            405                 410                 415

Gly Leu Lys Gly Leu Gln Ile Cys Gly Asn Ser Ile Met Pro Leu Leu
        420                 425                 430

Thr Phe Tyr Gly Asn Ser Ile Ala Asp Arg Phe Pro Thr His Ala Glu
    435                 440                 445

Gln Phe Asn Gln Cys Ile Asn Ser Gln Gly Tyr Thr Ser Ala Thr Leu
450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
            485                 490                 495

His Tyr Asp Ala Arg Ala Cys Leu Ser Pro Ala Thr Glu Arg Leu Tyr
        500                 505                 510

Ser Ala Val Arg His Val Val Gly Gln Lys Pro Ser Ser Asp Arg Pro
    515                 520                 525

Tyr Ile Trp Asn Asp Asn Glu Gln Gly Leu Asp Glu His Ile Ala Arg
530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 15
<211> LENGTH: 4945
<212> TYPE: DNA
<213> ORGANISM: Anabaena variabilis
<220> FEATURE:
<221> NAME/KEY: misc_feature
<222> LOCATION: (140)..(142)
<223> OTHER INFORMATION: n is a, c, g, or t
<220> FEATURE:
<221> NAME/KEY: misc_feature
<222> LOCATION: (1758)..(1758)
<223> OTHER INFORMATION: n is a, c, g, or t

```
<220> FEATURE:
<221> NAME/KEY: misc_feature
<222> LOCATION: (1761)..(1762)
<223> OTHER INFORMATION: n is a, c, g, or t
<220> FEATURE:
<221> NAME/KEY: misc_feature
<222> LOCATION: (1781)..(1781)
<223> OTHER INFORMATION: n is a, c, g, or t
<220> FEATURE:
<221> NAME/KEY: misc_feature
<222> LOCATION: (1784)..(1784)
<223> OTHER INFORMATION: n is a, c, g, or t
<220> FEATURE:
<221> NAME/KEY: misc_feature
<222> LOCATION: (1786)..(1786)
<223> OTHER INFORMATION: n is a, c, g, or t

<400> SEQUENCE: 15
tggccaccat caccatcacc attagggaag agcagatggg caagcttgac ctgtgaagtg      60
aaaaatggcg cacattgtgc gacattttttt tttgaattct acgtaaaaag cagccgatac    120
atcggctgct ttttttttgn nngaggttcc aacttgtggt ataatgaaat aagatcactc    180
cggagcgtat tttttgagtt atcgagattt tcaggagcta aggaggaact aaaatggaga    240
aaaaaatcac tggatatacc accgttgata tatcccaatg gcatcgtaaa gaacattttg    300
aggcatttca gtcagttgct caatgtacct ataaccagac cgttcagctg gatattacgg    360 ccttttttaaa gaccgtaaag aaaaataagc acaagtttta tccggccttt attcacattc    420
ttgcccgcct gatgaatgct catccggagt tccgtatggc aatgaaagac ggtgagctgg    480
tgatatggga tagtgttcac ccttgttaca ccgttttcca tgagcaaact gaaacgtttt    540
catcgctctg gagtgaatac cacgacgatt tccggcagtt tctacacata tattcgcaag    600
atgtggcgtg ttacggtgaa aacctggcct atttccctaa agggtttatt gagaatatgt    660
ttttcgtctc agccaatccc tgggtgagtt tcaccagttt tgatttaaac gtggccaata    720
tggacaactt cttcgccccc gttttcacca tgggcaaata ttatacgcaa ggcgacaagg    780
tgctgatgcc gctggcgatt caggttcatc atgccgtctg tgatggcttc catgtcggca    840
gaatgcttaa tgaattacaa cagtactgcg atgagtggca gggcggggcg taactgcagg    900
agctcaaaca gcagcctgta ttcaggctgc ttttttcgtt ttggtctgcg cgtaatctct    960
tgctctgaaa acgaaaaaac cgccttgcag ggcggttttt cgaaggttct ctgagctacc   1020
aactctttga accgaggtaa ctggcttgga ggagcgcagt caccaaaact tgtcctttca   1080
gtttagcctt aaccggcgca tgacttcaag actaactcct ctaaatcaat taccagtggc   1140
tgctgccagt ggtgcttttg catgtctttc cgggttggac tcaagacgat agttaccgga   1200
taaggcgcag cggtcggact gaacgggggg ttcgtgcata cagtccagct tggagcgaac   1260
tgcctacccg gaactgagtg tcaggcgtgg aatgagacaa acgcggccat aacagcggaa   1320
tgacaccggt aaaccgaaag gcaggaacag gagagcgcac gagggagccg ccaggggggaa   1380 acgcctggta tctttatagt cctgtcgggt ttcgccacca ctgatttgag cgtcagattt   1440
cgtgatgctt gtcagggggg cggagcctat ggaaaaacgg ctttgccgcg ccctctcac   1500 ttccctgtta agtatcttcc tggcatcttc caggaaatct ccgccccgtt cgtaagccat   1560
ttccgctcgc cgcagtcgaa cgaccgagcg tagcgagtca gtgagcgagg aagcggaata   1620
tatcctgtat cacatattct gctgacgcac cggtgcagcc ttttttctcc tgccacatga   1680
agcacttcac tgcacccctc atcagtgaac caccgctggt agcggtggtt tttttaggcc   1740
tatggccttt ttttttttntg nnaaacccttt cgcggtatgg natnanagcg cccggaagag   1800
```

```
agtcaattaa gagggtggtg aatgtgaaac cagtaacgtt atacgatgtc gcagagtatg    1860
ccggtgtctc ttatcagacc gtttcccgcg tggtgaacca ggccagccac gtttctgcga    1920
aaacgcggga aaaagtggaa gcggcgatgg cggagctgaa ttacattccc aaccgcgtgg    1980
cacaacaact ggcgggcaaa cagtcgttgc tgattggcgt tgccacctcc agtctggccc    2040
tgcacgcgcc gtcgcaaatt gtcgcggcga ttaaatctcg cgccgatcaa ctgggtgcca    2100
gcgtggtggt gtcgatggta gaacgaagcg cgtcgaagc ctgtaaagcg gcggtgcaca    2160
atcttctcgc gcaacgcgtc agtgggctga tcattaacta tccgctggat gaccaggatg    2220
ccattgctgt ggaagctgcc tgcactaatg ttccggcgtt atttcttgat gtctctgacc    2280
agacacccat caacagtatt attttctccc atgaagacgg tacgcgactg ggcgtggagc    2340
atctggtcgc attgggtcac cagcaaatcg cgctgttagc gggcccatta agttctgtct    2400
cggcgcgtct gcgtctggct ggctggcata aatatctcac tcgcaatcaa attcagccga    2460
tagcggaacg ggaaggcgac tggagtgcca tgtccggttt tcaacaaacc atgcaaatgc    2520
tgaatgaggg catcgttccc actgcgatgc tggttgccaa cgatcagatg gcgctgggcg    2580
caatgcgcgc cattaccgag tccgggctgc gcgttggtgc ggacatctcg gtagtgggat    2640
acgacgatac cgaagacagc tcatgttata tcccgccgtt aaccaccatc aaacaggatt    2700
ttcgcctgct ggggcaaacc agcgtggacc gcttgctgca actctctcag ggccaggcgg    2760
tgaagggcaa tcagctgttg cccgtctcac tggtgaaaag aaaaaccacc ctggcgccca    2820
atacgcaaac cgcctctccc cgcgcgttgg ccgattcatt aatgcagctg gcacgacagg    2880
tttcccgact ggaaagcggg cagtgagcgg tacccgataa aagcggcttc ctgacaggag    2940
gccgttttgt ttctcgagtt aattaaggca gtgagcgcaa cgcaattaat gtgagttagc    3000
tcactcatta ggcaccccag gctttacact ttatgcttcc ggctcgtatg ttgtgtggaa    3060
ttgtgagcgg ataacaattt cacacaggaa acagctatga ccatgattac ggattcactg    3120
gccgtcgttt tacaatctag aggccagcct ggccataagg agatatacat atgggccatc    3180
atcatcatca tcatcatcat catcacagca gcggccatat cgaaggtcgt catatgaaaa    3240
ccctgagcca ggcacagagc aaaaccagca gccagcagtt tagctttacc ggcaatagca    3300
gcgcaaatgt gattattggt aatcagaaac tgaccatcaa tgatgttgca cgtgttgccc    3360 gtaatgcac cctggttagc ctgaccaata ataccgatat tctgcagggt attcaggcca    3420
gctgtgatta tatcaataat gcagttgaaa gcggtgaacc gatttatggt gttaccagcg    3480
gttttggtgg tatggcaaat gttgcaatta gccgtgaaca ggcaagcgaa ctgcagacca    3540
atctggtttg gtttctgaaa accggtgcag gtaataaact gccgctggca gatgttcgtg    3600
cagcaatgct gctgcgtgca aatagccaca tgcgtggtgc aagcggtatt cgtctggaac    3660
tgattaaacg catggaaatc tttctgaatg ccggtgttac cccgtatgtt tatgaatttg    3720
gtagcattgg tgccagcggt gatctggttc cgctgagcta tattaccggt agcctgattg    3780
gcctggaccc gagctttaaa gttgattta atggcaaaga aatggacgca ccgaccgcac    3840
tgcgtcagct gaatctgagt ccgctgaccc tgctgccgaa agaaggtctg gcaatgatga    3900
atggcaccag cgttatgacc ggtattgcag caaattgtgt ttatgatacc cagattctga    3960
ccgcaattgc aatgggtgtt catgcactgg atattcaggc actgaatggt acaaatcaga    4020
gctttcatcc gtttatccat aacagcaaac cgcatccggg tcagctgtgg gcagcagatc    4080
agatgattag cctgctggcc aatagccagc tggttcgtga tgaactggat ggtaaacatg    4140
attatcgtga tcatgaactg atccaggatc gttatagcct gcgttgtctg ccgcagtatc    4200
```

```
tgggtccgat tgttgatggt attagccaga ttgccaaaca aatcgaaatt gagattaaca    4260
gcgttaccga taacccgctg attgatgttg ataatcaggc aagctatcat ggtggtaatt    4320
ttctgggtca gtatgttggt atgggtatgg atcatctgcg ctattatatc ggtctgctgg    4380
caaaacatct ggatgttcag attgcactgc tggcatcacc ggaatttagc aatggtctgc    4440
ctccgagtct gctgggtaat cgtgaacgta aagttaatat gggtctgaaa ggtctgcaga    4500
tttgcggtaa tagcattatg ccgctgctga cctttatgg taatagtatt gcagatcgtt     4560
ttccgaccca tgccgaacag tttaaccaga atattaacag ccagggttat accagcgcaa    4620
ccctggcacg tcgtagcgtt gatattttc agaattatgt tgccattgcc ctgatgtttg     4680
gtgttcaggc agttgatctg cgtacctaca aaaaaccgg tcattatgat gcacgtgcct     4740
gtctgtcacc ggcaaccgaa cgtctgtata gcgcagttcg tcatgttgtt ggtcagaaac    4800
cgacctcaga tcgtccgtat atttggaatg ataatgaaca gggtctggat gaacatattg    4860
cacgtattag tgcagatatt gcagccggtg gtgttattgt tcaggccgtt caggacattc    4920
tgccgtgtct gcattaaggc caaac                                          4945

<210> SEQ ID NO 16
<211> LENGTH: 56
<212> TYPE: DNA
<213> ORGANISM: Artificial Sequence
<220> FEATURE:
<223> OTHER INFORMATION: Synthetic

<400> SEQUENCE: 16
ctagaggcca gcctggccat aaggagatat acatatgaaa accctgagcc aggcac       56

<210> SEQ ID NO 17
<211> LENGTH: 47
<212> TYPE: DNA
<213> ORGANISM: Artificial Sequence
<220> FEATURE:
<223> OTHER INFORMATION: Synthetic

<400> SEQUENCE: 17
gatggtgatg gtggccagtt tggccttaat gcagacacgg cagaatg                 47
```

POLYNUCLEOTIDES ENCODING ENGINEERED TYROSINE AMMONIA LYASE VARIANTS

The present application is a Divisional of U.S. patent application Ser. No. 16/367,640, filed Mar. 28, 2019, now U.S. Pat. No. 10,533,168, which is a Divisional of U.S. patent application Ser. No. 15/432,429, filed Feb. 14, 2017, now U.S. Pat. No. 10,287,567, which is a Divisional of U.S. patent application Ser. No. 14/688,126, filed Apr. 16, 2015, now U.S. Pat. No. 9,605,252, which claims priority to U.S. Prov. Appln. Ser. No. 61/980,167, filed Apr. 16, 2014, each of which is hereby incorporated by reference in their entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX7-143US2_ST25.TXT, created on Apr. 15, 2015, 65,536 bytes, machine format IBM-PC, MS-Windows operating system, is hereby incorporated by reference.

FIELD OF THE INVENTION

The present invention provides engineered tyrosine ammonia-lyase (TAL) polypeptides and compositions thereof. In some embodiments, the engineered TAL polypeptides have been optimized to provide enhanced catalytic activity while reducing sensitivity to proteolysis and increasing tolerance to acidic pH levels. The invention also provides methods for utilization of the compositions comprising the engineered TAL polypeptides for therapeutic and industrial purposes.

BACKGROUND OF THE INVENTION

Tyrosine ammonia lyase (TAL; also referred to as tyrase, L-tyrosine ammonia lyase, and "L-tyrosine ammonia lyase [trans-p-hyroxycinnamate forming]"), along with histidine ammonia lyase (HAL) and phenylalanine ammonia-lyase (PAL) are members of the aromatic amino acid lyase family (EC 4.3.1.23-1.25 and 4.3.1.3). The enzymes having TAL activity are currently classified in EC4.3.1.23 (previously classified as EC 4.3.1.5). TAL catalyzes the formation of p-coumaric acid from L-tyrosine.

Tyrosinemia (also referred to as "hereditary tyrosinemia," and "hypertyrosinemia") is a genetic disorder characterized by elevated blood levels of tyrosine, due to the deficiency of an enzyme required for the catabolism of tyrosine in the liver. If untreated, tyrosine and other metabolites accumulate in the tissues and organs of affected individuals, resulting in serious medical issues. Tyrosinemia is an inborn error of metabolism inherited in an autosomal recessive pattern. There are three types of tyrosinemia, each caused by the deficiency of a different enzyme. Currently used treatment methods depend upon the type of tyrosinemia involved. A low protein diet is often used.

Type I tyrosinemia (also referred to as "FAH deficiency," "fumaryl acetoacetase deficiency," "fumaryl aceotacetate hydrolase deficiency," "hereditary infantile tyrosinemia," and "hepatorenal tyrosinemia") is caused by a deficiency of fumarylacetoacetate hydrolase, due to mutations in the fah gene. This is the most severe form of the disease, with symptoms usually appearing in the first few months of life, commonly including failure to thrive, diarrhea, bloody stools, vomiting, jaundice, enlarged liver, the tendency to easily bruise, lethargy, irritability, fever, and other symptoms, such as a distinctive cabbage-like odor of the skin and urine. Some affected infants have repeated neurologic episodes of acute polyneuropathy, characterized by severe leg pain, as well as altered mental status, abdominal pain, and respiratory failure. Infants with the acute form are typically affected at birth and there is a rapid onset of symptoms that can lead to developmental delays, enlarged spleen, ascites, kidney disease, and blood clotting abnormalities. Untreated, it can lead to hepatic and renal failure, nervous system problems, and an increased risk of liver cancer (e.g., hepatocellular carcinoma). In some cases, hypertension and hypertrophic cardiomyopathy are present. If untreated, this disease can be fatal. In the less-common chronic form, the symptoms exhibit a more gradual onset and tend to be less severe. Affected infants initially exhibit vomiting, diarrhea, enlarged liver and spleen, and failure to thrive. Eventually, progressive liver cirrhosis occurs, leading to chronic liver failure, developmental delays, and renal Fanconi syndrome (a rare kidney disorder characterized by weakening and softening of the bones [rickets], vomiting, dehydration, weakness, and fever). In some cases, the most effective treatment has been full or partial liver transplant. Worldwide, this form affects approximately 1 in 100,000 human births (Genetics Home Reference, U.S. National Library of Medicine).

Type II tyrosinemia (also referred to as "keratosis palmoplantaris-corneal dystrophy," oculocutaneous tyrosinemia," "Richner-Hanhart syndrome," "tyrosinemia due to TAT deficiency," and "tyrosinema due to tyrosine aminotransferase deficiency,") is caused by a deficiency of tyrosine aminotransferase, due to mutations in the tat gene. It affects the eyes, skin, and mental development. As with Type 1 tyrosinemia, symptoms usually begin in early life, and include excessive tearing, photophobia, eye pain and redness, and painful skin lesions on the palms and soles. About half of affected individuals have some level of intellectual disability. This form occurs in less than 1 in 250,000 persons (Genetics Home Reference, supra).

Type III tyrosinemia (also referred to as "tyrosinemia due to 4-hydroxyphenylpyruvate dioxygenase deficiency," "tyrosinemia due to 4-hydroxyphenylpyuriv acid oxidase deficiency," and "tyrosinemia due to HPD deficiency") is a rare disorder, caused by a deficiency of 4-hydroxyphenylpyruvate dioxygenase, due to mutations in the hpd gene. Symptoms of this form include intellectual disability, seizures, and intermittent ataxia. This form is very rare, only a few cases have been reported (Genetics Home Reference, supra).

There are additional cases in which there are temporary elevated tyrosine levels, due to non-genetic factors such as vitamin C deficiency or premature birth, which results in immature liver enzymes. Differential diagnoses are used to differentiate these transient cases from tyrosinema I, II, or III.

In addition to tyrosinema, there are other diseases associated with insufficient or absent tyrosine metabolism. For example, alkaptonuria also referred to as alcaptonuria, is a disease caused by deficiency of homogentisate 1,2-dioxygenase, which is an enzyme involved in tyrosine degradation. This enzyme is encoded by the HGD gene. Insufficient activity of this enzyme results in the accumulation of homogentisic acid. Excess homogentisic acid and related compounds are deposited in connective tissues, causing the cartilage and skin to darken. Over time, arthritis may result due to the accumulation of homogentisic acid and related metabolites in the joints of affected individuals. Homogentisic acid is also excreted in urine, making the urine turn black. Alkaptonuria is a rare disease that affects 1 in 250,000 to 1,000,000 people worldwide (See, Genetics Home Reference, supra).

Treatment of these diseases has largely been the life-long use of a methionine-, phenylalanine-, and tyrosine-restricted diet. Treatment with nitisinone (NTBC; 2-(2-nitro-4-trifluoromethylbenzol)-1,3-cyclohexane dione; Orfadin®) has been reported to be helpful for type I tyrosinemia and alkaptonuria, due to its inhibition of the 4-hydroxyphenylpyruvate oxidase pathway. However, NTBC must be used in combination with a challenging and costly methionine-, phenylalanine-, and tyrosine-restricted diet to prevent both liver failure and carcinogenesis. There remains a need in the art for easy to administer, effective treatment(s) to ameliorate the symptoms of these diseases and allow patients to utilize normal diets.

SUMMARY OF THE INVENTION

The present invention provides engineered tyrosine ammonia-lyase (TAL) polypeptides and compositions thereof. In some embodiments, the engineered TAL polypeptides have been optimized to provide enhanced catalytic activity while reducing sensitivity to proteolysis and increasing tolerance to acidic pH levels. The invention also provides methods for utilization of the compositions comprising the engineered TAL polypeptides for therapeutic and industrial purposes.

In some embodiments, the present invention provides engineered TAL polypeptides (also referred to herein as "recombinant TAL polypeptides") and biologically active fragments and analogs thereof having improved properties when compared to a wild-type TAL enzyme and/or a reference TAL polypeptide under essentially the same conditions. The invention is further directed to methods of using the engineered TAL polypeptides and biologically active fragments and analogs thereof in therapeutic and/or industrial compositions.

The present invention provides recombinant tyrosine ammonia lyases and/or biologically active recombinant tyrosine ammonia lyase fragments comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:4, 6, 8 10, 12, and/or 14.

In some embodiments, the present invention provides recombinant tyrosine ammonia lyases comprising at least one mutation at position 18, 47, 54, 59, 64, 73, 77, 88, 91, 93, 95, 97, 107, 108, 214, 219, 222, 253, 304, 307, 315, 364, 367, 389, 394, 396, 400, 401, 423, 447, 453, 462, 490, 500, 503, 521, 550, 554, 564, and/or 565, wherein the positions are numbered with reference to SEQ ID NO:4, 6, 8 10, 12, and/or 14. In some additional embodiments, the recombinant tyrosine ammonia lyase comprises at least one mutation in at least one position selected from S73, I77, A88, V91, S93, E95, A97, L108, L219, M222, D253, Y304, G307, S315, L364, Y367, Q389, A394, P396, N400, G401, I423, A447, N453, A462, R490, A500, A550, and/or P564, wherein the positions are numbered with reference to SEQ ID NO:10. In some further embodiments, the recombinant tyrosine ammonia lyase comprises at least one mutation selected from S73I, I77M, A88S, V91R, S93L/P/R/T/W, E95D, A97T, L108C, L219M, M222T, D253G, Y304F, G307P/H, S315A, L364H/M/Y, Y367F, Q389T, A394V, P396Q, N400M/T, G401C/L, I423F, A447T, N453C, A462T, R490T, A500S, A550V, P564S, wherein the positions are numbered with reference to SEQ ID NO:10. In some yet additional embodiments, the recombinant tyrosine ammonia lyase comprises a substitution set selected from I77M/V91R/S93R/A97T/Q389T/N400M; I77M/A88S/S93L/E95D/A97T/M222T/R490T; I77M/S315A/L364M/Q389T; I77M/S315A/N453C/A462T; I77M/Q389T; I77M/L364M/N453C; I77M/Q389T/N400M; I77M/A88S/V91R/S93P/M222T/S315A/L364Y/Q389T/N400T/N453C; I77M/M222T/S315A/L364Y/N400M; I77M/S93W/E95D/A97T/L364M/N453C; I77M/M222T/S315A/Q389T/N400M; I77M/E95D; I77M/S93L/E95D/M222T/N400T; I77M/S315A/Q389T/N400M; I77M/S315A/N400T; I77M/M222T/Q389T; I77M/S315A/L364M; I77M/S93W/S315A/L364M; I77M/S93R/E95D/M222T/S315A/N400M; I77M/Q389T/N400T; I77M/S315A/Y367F/N400M/N453C; I77M/V91R/S93R/E95D/A97T/M222T/N453C; I77M/L364M/Q389T/N400M; I77M/S93L/A97T/N400M/N453C/R490T; I77M/M222T/L364H; I77M/S315A/L364M/R490T; I77M/S93W/S315A/Q389T; I77M/S93W/A97T/S315A; I77M/S93R/E95D/A97T/R490T/P564S; I77M/S93R/E95D/S315A/L364Y/N453C; I77M/M222T/L364M/N400T/N453C; I77M/M222T/N400T; I77M/S315A/R490T; I77M/L364H/N400M/R490T; I77M/S315A/L364M/Q389T/N453C; I77M/V91R/S93P/E95D/A97T; I77M/E95D/Q389T/N400M/N453C; I77M/S93W/S315A/Q389T/N400T; I77M/S315A/N400M/N453C; I77M/L364M/N400T; I77M/L364M/N400T/R490T; I77M/M222T/S315A; I77M/L108C/S315A/L364M/N400M; I77M/V91R/S93W/E95D/R490T; I77M/S93R/E95D/M222T/L364M/A550V; V91R/S93R/L108C/M222T/S315A/L364Y/N400M; I77M/V91R/S93W/E95D/A97T/L108C/M222T/L364M/Q389T; I77M/V91R/S93L/S315A; I77M/A88S/S93R/S315A/N400T; I77M/S315A/Q389T/N400T/N453C; I77M/S93L/S315A/N400M; I77M/L364H; I77M/V91R/S93P/E95D/A97T/S315A/Q389T; I77M/V91R/S93L/E95D/S315A/L364M/N453C/R490T; I77M/L364M/Q389T; I77M/S315A/Q389T; I77M/S93L/E95D/S315A; I77M/L108C/L219M/S315A/Q389T/N400M; I77M/L364M/R490T; I77M/V91R/S93L/E95D/S315A/Q389T; I77M/S93L/E95D/M222T/N400M; I77M/L108C/M222T/S315A/N400M; I77M/N400M/N453C; I77M/S93P/E95D/S315A/N400M; I77M/V91R/S93W/L108C/L364M/Q389T/N400T/N453C; I77M/L364M; I77M/V91R/S93L/M222T/N400M; I77M/S93L/S315A/L364M/Q389T/N400T; I77M/S93P/E95D/L108C/S315A/R490T; I77M/L108C/M222T/S315A/R490T; I77M/A88S/S93L/E95D/M222T/S315A/L364H/N400M; I77M/M222T; I77M/S315A/Q389T/N400T; I77M/S315A/L364M/N453C; I77M/V91R/S93L/E95D/A97T; I77M/M222T/S315A/N400T/I423F; I77M/L108C/S315A/N400M/R490T; I77M/S93R/A97T/S315A; I77M/V91R/S93R/E95D/S315A/N400M; I77M/L364M/Q389T/A394V/N400M; I77M/S315A/L364M/N400T/A447T; I77M/S93W/N400T; I77M/M222T/S315A/R490T; I77M/A88S/S93L/E95D/A97T/M222T/S315A/L364M/N400T; I77M/L364H/N400M/R490T; I77M/Q389T/N453C; I77M/N400T; I77M/S315A/L364M/Q389T/N400M/N453C; I77M/S315A/L364H/N453C; I77M/L364H/N400M; I77M/S315A/L364M/N400M; I77M/L364M/N400M/N453C/R490T; I77M/S315A; I77M/L108C/S315A/L364Y/Q389T; I77M/A88S/S93W/A97T/L108C/S315A/L364Y/N400T; I77M/S315A/N453C/R490T; I77M/E95D/L364M; I77M/V91R/S93W/E95D/L108C/M222T/R490T; I77M/L364H/Q389T/

N400M/N453C; I77M/S93L/A97T/S315A/N400M; I77M/ S93W/E95D/A97T/M222T/S315A/L364M/Q389T/N453C; I77M/E95D/A97T/S315A/L364M/Q389T/N400T/R490T; I77M/E95D/S315A/Q389T/A500S; I77M/A97T; I77M/L108C/S315A/L364M; I77M/M222T/L364M; I77M/R490T; I77M/M222T/S315A/N400M; I77M/M222T/Q389T/N453C; I77M/V91R/S93R/Q389T; I77M/V91R/S93W/A97T/S315A/N453C; I77M/N400M; I77M/N453C; I77M/S315A/L364M/Q389T/N400M; I77M/V91R/S93P/E95D/S315A/N400M; I77M/E95D/L364H/N400M; I77M/S93R/L364M/Q389T/N453C; I77M/E95D/A97T/S315A/Q389T/N400M; I77M/V91R/S93L/L364M/Q389T/N400M/N453C; I77M/S315A/N400M; I77M/S93W/E95D/A97T/N400M; I77M/A88S/E95D/A153V/S315A/P396Q/N400T/N453C; I77M/V91R/S93L/A97T/S315A/N400M/N453C; I77M/L108C/L364M/Q389T/N400T, F18H/L47A/T54K/G59R/I77M/L214Q/S315A/L364M/Q389T/N400M/N453C/Q521K; F18H/L47A/G59R/I77M/A97T/L214Q/S315A/Q389T/N400M/N453C/C503Q/Q521K; F18H/T54K/S73K/I77M/S315A/L364M/Q389T/N400M/N453C/C503Q/Q521K/V554I; F18H/L47A/T54K/G59R/S73K/I77M/S315A/L364M/Q389T/N400M/N453C/Q521K/C565P; F18H/L47A/T54K/I77M/L214Q/S315A/L364M/Q389T/N400M/N453C/C565P; F18H/L47A/G59R/I77M/L214Q/S315A/L364M/Q389T/N400M/N453C; F18H/L47A/S73K/I77M/L214Q/S315A/N400M/N453C/Q521K; F18H/L47A/S73K/I77M/L214Q/S315A/L364M/N400M/N453C/C503Q; F18H/G59R/I77M/S315A/L364M/Q389T/N400M/N453C/Q521K; F18H/I77M/S315A/L364M/Q389T/N400M/N453C/C503Q/C565P; L47A/G59R/I77M/L214Q/S315A/N400M/N453C/C503Q; F18H/G59R/I77M/L214Q/S315A/L364M/Q389T/N400M/N453C/C503Q; F18H/L47A/I77M/L214Q/S315A/N400M/N453C/C503Q/Q521K; F18H/G59R/S73K/I77M/L214Q/S315A/N400M/N453C; F18H/L47A/G59R/S73K/I77M/A97T/L214Q/S315A/Q389T/N400M/N453C/C503Q; F18H/L47A/S49I/T54K/S73K/I77M/A97T/L214Q/S315A/Q389T/N400M/N453C; F18H/S73K/I77M/S315A/L364M/Q389T/N400M/N453C; F18H/T54K/G59R/I77M/L214Q/S315A/L364M/Q389T/N400M/N453C/C503Q/Q521K; F18H/L47A/S73K/I77M/L214Q/S315A/L364M/Q389T/N400M/N453C/Q521K; F18H/S73K/I77M/N193D/R305M/S315A/L364M/Q389T/N400M/N453C/C503Q/Q521K; F18H/L47A/I77M/L214Q/S315A/L364M/N400M/N453C/Q521K; F18H/L47A/I77M/S315A/N400M/N453C/Q521K; F18H/I77M/L214Q/S315A/L364M/N400M/N453C/C503Q; F18H/I77M/S315A/L364M/Q389T/N400M/N453C/C503Q; F18H/L47A/S73K/I77M/L214Q/S315A/L364M/Q389T/N400M/N453C/C565P; F18H/L47A/T54K/S73K/I77M/L214Q/S315A/L364M/N400M/N453C/C503Q; F18H/L47A/S73K/I77M/L214Q/R305M/S315A/L364M/N400M/N453C; F18H/L47A/G59R/I77M/L214Q/S315A/L364M/Q389T/N400M/N453C/C565P; F18H/L47A/T54K/G59R/C64S/S73K/I77M/L214Q/S315A/L364M/N400M/N453C/C503Q; F18H/L47A/S73K/I77M/L214Q/S315A/L364M/Q389T/N400M/N453C/C503Q/Q521K/C565P; F18H/L47A/T54K/G59R/S73K/I77M/L214Q/S315A/L364M/Q389T/N400M/N453C/C565P; F18H/S73K/I77M/S315A/L364M/Q389T/N400M/N453C/C503Q/C565P; F18H/S73K/I77M/L214Q/S315A/L364M/N400M/N453C/C503Q/Q521K; F18H/L47A/I77M/L214Q/S315A/N400M/N453C/C503Q; F18H/I77M/S315A/L364M/Q389T/N400M/N453C; F18H/L47A/G59R/S73K/I77M/L214Q/S315A/L364M/Q389T/N400M/N453C/C503Q/C565P; F18H/L47A/S73K/I77M/L214Q/S315A/Q389T/N400M/N453C/Q521K/C565P; F18H/L47A/G59R/S73K/I77M/S315A/Q389T/N400M/N453C; F18H/S73K/I77M/L214Q/S315A/L364M/Q389T/N400M/N453C/C503Q/Q521K; F18H/L47A/I77M/L214Q/S315A/L364M/Q389T/N400M/N453C/C503Q; F18H/L47A/T54K/G59R/S73K/I77M/L214Q/S315A/L364M/Q389T/N400M/N453C/C503Q; F18H/I77M/S315A/L364M/N400M/N453C/Q521K; F18H/T54K/I77M/L214Q/S315A/L364M/Q389T/N400M/N453C/C503Q; F18H/L47A/I77M/A97T/L214Q/S315A/Q389T/N400M/N453C/C503Q/Q521K/C565P; F18H/L47A/S73K/I77M/R305M/S315A/L364M/N400M/N453C/C503Q; F18H/L47A/I77M/S315A/Q389T/N400M/N453C/Q521K; F18H/I77M/L214Q/S315A/L364M/Q389T/N400M/N453C; F18H/G59R/I77M/S315A/Q389T/N400M/N453C/Q521K; F18H/L47A/T54K/G59R/S73K/I77M/L214Q/H250N/S315A/L364M/N400M/N453C; F18H/I77M/L214Q/S315A/L364M/Q389T/N400M/N453C/C503Q/Q521K; F18H/L47A/G59R/S73K/I77M/A97T/L214Q/S315A/Q389T/N400M/N453C/C503Q/Q521K/C565P; F18H/T54K/G59R/S73K/I77M/S315A/L364M/Q389T/N400M/N453C; F18H/L47A/I77M/A97T/L214Q/S315A/Q389T/N400M/N453C/Q521K; F18H/L47A/S73K/I77M/R305M/S315A/L364M/Q389T/N400M/N453C/Q521K/C565P; F18H/L47A/S73K/I77M/L214Q/S315A/Q389T/N400M/N453C/C503Q/Q521K; F18H/S73K/I77M/L214Q/S315A/L364M/N400M/N453C/C503Q; F18H/L47A/T54K/I77M/S315A/L364M/Q389T/N400M/N453C; F18H/T54K/I77M/S315A/L364M/Q389T/N400M/N453C/C503Q/C565P; F18H/L47A/C64S/S73K/I77M/A97T/L214Q/S315A/Q389T/N400M/N453C/C503Q; F18H/S73K/I77M/S315A/L364M/Q389T/N400M/N453C/C503Q/Q521K; F18H/L47A/I77M/S315A/L364M/Q389T/N400M/N453C/Q521K/C565P; F18H/L47A/G59R/I77M/L214Q/S315A/Q389T/N400M/N453C/C503Q/Q521K; F18H/L47A/I77M/S315A/L364M/Q389T/N400M/N453C/C503Q/Q521K/C565P; F18H/L47A/G59R/I77M/L214Q/R305M/S315A/L364M/N400M/N453C/C503Q/Q521K; F18H/L47A/G59R/S73K/I77M/L214Q/S315A/L364M/N400M/N453C/C503Q; F18H/L47A/G59R/I77M/S315A/Q389T/N400M/N453C/C503Q/Q521K/C565P; F18H/L47A/G59R/I77M/S315A/Q389T/N400M/N453C/C503Q/Q521K; F18H/L47A/T54K/G59R/S73K/I77M/L214Q/S315A/L364M/Q389T/N400M/N453C/C503Q/Q521K/C565P; F18H/L47A/S73K/I77M/A97T/L214Q/R305M/S315A/Q389T/N400M/N453C/Q521K/C565P; F18H/S73K/I77M/S315A/Q389T/N400M/N453C/C565P; F18H/L47A/I77M/S315A/L364M/Q389T/N400M/N453C; F18H/L47A/C64S/S73K/I77M/L214Q/S315A/Q389T/N400M/N453C/C503Q/C565P; F18H/S73K/I77M/L214Q/S315A/L364M/Q389T/N400M/N453C/Q521K/C565P; F18H/L47A/T54K/S73K/I77M/L214Q/S315A/L364M/Q389T/L392Q/N400M/N453C/C503Q/Q521K; F18H/L47A/T54K/G59R/S73K/I77M/L214Q/S315A/N400M/N453C/C503Q/Q521K; F18H/L47A/T54K/G59R/I77M/L214Q/S315A/Q389T/N400M/N453C/C503Q/C565P; F18H/L47A/S73K/I77M/L214Q/S315A/L364M/Q389T/N400M/N453C/C503Q/Q521K; F18H/L47A/T54K/S73K/I77M/A97T/L214Q/S315A/N400M/N453C/C503Q; F18H/L47A/I77M/L214Q/S315A/L364M/Q389T/N400M/N453C/C503Q/Q521K; F18H/L47A/T54K/I77M/S315A/L364M/N400M/N453C; F18H/L47A/T54K/I77M/L214Q/S315A/L364M/Q389T/N400M/N453C/C503Q/Q521K; F18H/T54K/G59R/I77M/S315A/L364M/Q389T/N400M/N453C; F18H/L47A/G59R/I77M/L214Q/S315A/Q389T/N400M/N453C/C503Q/C565P; F18H/L47A/I77M/S315A/N400M/N453C/C565P; F18H/T54K/G59R/I77M/L214Q/S315A/L364M/N400M/N453C/Q521K; F18H/L47A/S73K/I77M/L214Q/S315A/L364M/N400M/N453C; F18H/

L47A/T54K/I77M/L214Q/S315A/L364M/Q389T/N400M/N453C; F18H/L47A/T54K/G59R/S73K/I77M/A97T/L214Q/S315A/Q389T/N400M/N453C/C503Q; F18H/L47A/G59R/I77M/L214Q/S315A/L364M/N400M/N453C/C503Q/Q521K/C565P; F18H/L47A/I77M/L214Q/S315A/L364M/Q389T/N400M/N453C/C503Q/Q521K/C565P; F18H/L47A/G59R/I77M/L214Q/S315A/L364M/Q389T/N400M/N453C/C503Q/Q521K/C565P; F18H/L47A/G59R/S73K/I77M/L214Q/S315A/L364M/Q389T/N400M/N453C/C503Q; G59R/I77M/S315A/L364M/Q389T/N400M/N453C; F18H/S73K/I77M/S315A/L364M/Q389T/N400M/N453C/Q521K/C565P; F18H/L47A/T54K/I77M/A97T/L214Q/S315A/N400M/N453C/C503Q; F18H/L47A/I77M/A97T/L214Q/S315A/N400M/N453C/Q521K/C565P; F18H/L47A/G59R/S73K/I77M/S315A/L364M/N400M/N453C/C565P; F18H/I77M/L214Q/S315A/L364M/Q389T/N400M/N453C/Q521K; F18H/L47A/G59R/S73K/I77M/L214Q/S315A/N400M/N453C/C503Q/Q521K/C565P; F18H/L47A/C64S/S73K/I77M/L214Q/S315A/L364M/Q389T/N400M/N453C/Q521K; F18H/L47A/G59R/S73K/I77M/S315A/L364M/Q389T/N400M/N453C/C503Q; F18H/G59R/S73K/I77M/L214Q/S315A/L364M/N400M/N453C/C503Q; F18H/L47A/I77M/S315A/L364M/N400M/N453C/C503Q; F18H/T54K/G59R/S73K/I77M/L214Q/S315A/Q389T/N400M/N453C/C503Q/Q521K; F18H/L47A/S73K/I77M/L214Q/S315A/L364M/N400M/N453C/C503Q/Q521K; I77M/L214Q/S315A/L364M/Q389T/N400M/N453C/Q521K/C565P; F18H/I77M/L214Q/S315A/Q389T/N400M/N453C/C503Q/Q521K; F18H/L47A/G59R/I77M/A97T/L214Q/S315A/L364M/N400M/N453C/C503Q/Q521K/C565P; F18H/L47A/I77M/S315A/N400M/N453C/C503Q/Q521K/C565P; F18H/G59R/I77M/L214Q/S315A/L364M/Q389T/N400M/N453C/Q521K; F18H/L47A/T54K/S73K/I77M/L214Q/S315A/Q389T/N400M/N453C/C503Q/C565P; L47A/I77M/L214Q/S315A/Q389T/N400M/N453C; F18H/G59R/S73K/I77M/S315A/L364M/Q389T/N400M/N453C/C503Q; F18H/T46N/L47A/S73K/I77M/L214Q/S315A/L364M/M370Q/Q389T/N400M/N453C/C503Q/Q521K; F18H/L47A/I77M/L214Q/S315A/L364M/N400M/N453C/C503Q/Q521K; F18H/L47A/I77M/S315A/L364M/Q389T/N400M/N453C/C503Q; F18H/L47A/T54K/S73K/I77M/L214Q/S315A/L364M/Q389T/N400M/N453C/C503Q/Q521K/C565P; F18H/L47A/I77M/A97T/S315A/Q389T/N400M/N453C/Q521K; F18H/L47A/S73K/I77M/A97T/L214Q/S315A/L364M/N400M/N453C/C503Q/Q521K; L47A/G59R/I77M/S315A/L364M/N400M/N453C/C503Q/Q521K/C565P; F18H/G59R/S73K/I77M/L214Q/S315A/Q389T/N400M/N453C; S73K/I77M/L214Q/S315A/L364M/N400M/N453C/C503Q/Q521K/C565P; F18H/L47A/C64S/S73K/I77M/S315A/L364M/Q389T/N400M/N453C/C503Q/C565P; F18H/L47A/G59R/I77M/L214Q/S315A/Q389T/N400M/N453C; F18H/L47A/I77M/L214Q/S315A/Q389T/N400M/N453C/Q521K/C565P; F18H/G59R/S73K/I77M/S315A/Q389T/N400M/N453C/C565P; L47A/I77M/L214Q/S315A/L364M/Q389T/N400M/N453C/C503Q; F18H/S73K/I77M/L214Q/S315A/L364M/Q389T/N400M/N453C/Q521K; F18H/L47A/C64S/S73K/I77M/L214Q/S315A/L364M/N400M/N453C/C503Q/Q521K/C565P; F18H/L47A/T54K/I77M/A97T/S315A/Q389T/N400M/N453C/C503Q; F18H/L47A/G59R/I77M/L214Q/S315A/N400M/N453C/C503Q/Q521K/C565P; F18H/L47A/S73K/I77M/A97T/S315A/Q389T/N400M/N453C/C503Q/Q521K; F18H/L47A/S73K/I77M/A97T/L214Q/S315A/Q389T/N400M/N453C/C503Q; F18H/L47A/T54K/G59R/I77M/L214Q/S315A/Q389T/N400M/N453C/C503Q; F18H/L47A/I77M/A97T/L214Q/S315A/Q389T/N400M/N453C/C503Q; I77M/Y160P/S315A/L364M/M372S/Q389T/N400M/N453C; I77M/S175A/S315A/L364M/Q389T/N400M/N453C; I77M/Y160P/S315A/Q336V/L364M/Q389T/N400M/N453C; I77M/Y160P/S315A/L364M/Q389T/N400M/N453C; I77M/S315A/L364M/Q389T/N400M/N453C/V484A, wherein the positions are numbered with reference to SEQ ID NO:10.

In some embodiments, the recombinant tyrosine lyase variant comprises at least one variant selected from Variant No. 1 through Variant No. 294. In some embodiments, the recombinant tyrosine lyase variant consists of a recombinant tyrosine lyase variant selected from Variant No. 1 through Variant No. 294. In some embodiments, the recombinant tyrosine lyase is selected from Variant No. 4 through Variant No. 294.

In some embodiments, the recombinant tyrosine ammonia lyases are *Anabaena variabilis* enzymes. In some additional embodiments, the recombinant tyrosine ammonia lyases comprise the polypeptide sequence of SEQ ID NO:8, 12, and/or 14.

In some additional embodiments, the recombinant tyrosine ammonia lyase is thermostable. In some further embodiments, the recombinant tyrosine ammonia lyase is resistant to proteolysis. In some embodiments, the recombinant tyrosine ammonia lyase is resistant to at least one digestive tract protease. In some additional embodiments, the recombinant tyrosine ammonia lyase is resistant to chymotrypsin, trypsin, carboxypeptidases, and/or elastases. In some further embodiments, the recombinant tyrosine ammonia lyase is acid stable. In some embodiments, the recombinant tyrosine ammonia lyase is a deimmunized tyrosine ammonia lyase. In some additional embodiments, the recombinant tyrosine ammonia lyase is purified.

In still some further embodiments, the recombinant tyrosine ammonia lyase exhibits at least one improved property selected from: i) enhanced catalytic activity; ii) reduced sensitivity to proteolysis; iii) increased tolerance to acidic pH; iv) reduced aggregation; v) decreased Km for tyrosine; vi) reduced immunogenicity; or a combination of any of i), ii), iii), iv), v) and/or vi), as compared to a reference sequence. In some embodiments, the reference sequence is SEQ ID NO:8, 10, 12, or 14.

The present invention also provides compositions comprising at least one recombinant tyrosine ammonia lyase provided herein.

The present invention also provides recombinant polynucleotide sequences encoding at least one recombinant tyrosine ammonia lyase, as provided herein. In some embodiments, the polynucleotide sequence is codon-optimized. In some embodiments, the recombinant polynucleotide sequence is operably linked to a control sequence. In some embodiments, the control sequence is a promoter. In some additional embodiments, the promoter is a heterologous promoter.

The present invention also provides vectors comprising at least one recombinant polynucleotide sequence, as provided herein. In some embodiments, vector is an expression vector wherein the recombinant polynucleotide sequence encoding at least one recombinant tyrosine ammonia lyase is operably linked to a control sequence. In some additional embodiments, the control sequence is a promoter. In some additional embodiments, the promoter is a heterologous promoter.

The present invention also provides host cells comprising at least one expression vector comprising at least one polynucleotide sequence encoding at least one recombinant tyrosine ammonia lyase. In some embodiments, the host cell is prokaryotic, wherein is some alternative embodiments, the host cell is eukaryotic.

The present invention also provides methods of producing a tyrosine ammonia lyase variant, comprising culturing the host cell under conditions that said tyrosine ammonia lyase encoded by the recombinant polynucleotide is produced. In some embodiments, the methods further comprise the step of recovering the tyrosine ammonia lyase. In some further embodiments, the methods further comprise the step of purifying the tyrosine ammonia lyase.

The present invention also provides pharmaceutical compositions for the treatment of tyrosinemia, comprising an enzyme composition comprising at least one recombinant tyrosine ammonia lyase. In some embodiments, the pharmaceutical compositions further comprise at least one pharmaceutically acceptable carrier and/or excipient. In some additional embodiments, the pharmaceutical composition is suitable for oral administration to a human. In some further embodiments, the pharmaceutical composition is in the form of a pill, tablet, capsule, gelcap, liquid, or emulsion. In some still additional embodiments, the pill, tablet, capsule, or gelcap further comprises an enteric coating. In some additional embodiments, the pharmaceutical composition is coadministered with nitisone. In some further embodiments, the pharmaceutical composition comprises nitisinone. In some embodiments, the pharmaceutical composition is suitable for parenteral injection into a human.

The present invention also provides methods for treating and/or preventing the symptoms of tyrosinemia or alkaptonuria in a subject, comprising providing a subject having tyrosinemia or alkaptonuria, and providing at least one pharmaceutical composition as provided herein to said subject. In some embodiments, the symptoms of tyrosinemia or alkaptonuria are ameliorated. In some further embodiments, the treated subject is able to eat a diet that is less restricted in its methionine, phenylalanine and/or tyrosine content than diets required by subjects exhibiting the symptoms of tyrosinemia or alkaptonuria. In some embodiments, the subject is an infant or child, while in some alternative embodiments, the subject is an adult or young adult.

The present invention also provides methods for the production of L-tyrosine and/or L-tyrosine derivatives comprising the steps of providing at least one recombinant TAL variant and a suitable substrate, and combining the TAL variant(s) and said substrate under conditions such that L-tyrosine and/or at least one L-tyrosine derivative is produced.

The present invention also provides methods for the production of coumaric acid, comprising the steps of providing at least one recombinant TAL variant and a suitable substrate, and combining said TAL variant(s) and said substrate under conditions such that coumaric acid is produced.

The present invention also provides methods for the resolution of racemic tyrosine and/or tyrosine derivatives to synthesize D-tyrosine and/or at least one D-tyrosine derivative, comprising the steps of providing at least one recombinant TAL variant and a racemic mixture of tyrosine and/or tyrosine derivatives, combining the TAL variant(s) and said racemic tyrosine and/or racemic tyrosine derivatives under conditions such that D-tyrosine and/or D-tyrosine derivative is produced.

The present invention also provides methods for the conversion of alpha tyrosine and/or its derivatives to beta tyrosine and/or its derivatives, comprising the steps of providing at least one recombinant TAL variant and a composition comprising alpha tyrosine and/or its derivatives, combining the TAL variant(s) and alpha tyrosine and/or its derivatives under conditions such that beta tyrosine and/or beta tyrosine derivative is/are produced.

The present invention also provides use of the enzyme compositions and pharmaceutical compositions.

DESCRIPTION OF THE INVENTION

Figure 1:
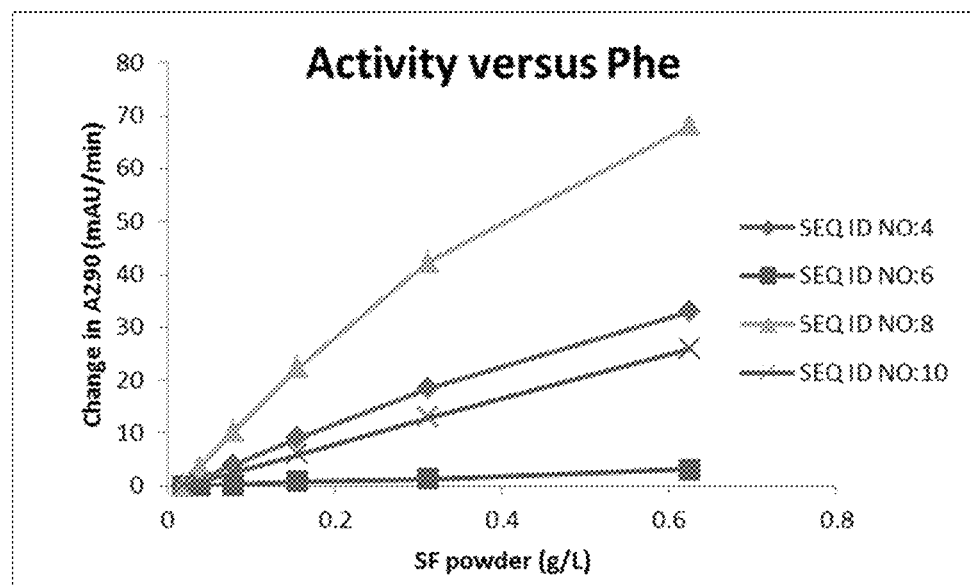
FIG. 1 provides a graph showing the activity of WT AvPAL and AvPAL variants (i.e., TAL variants) on phenylalanine.

The present invention provides engineered tyrosine ammonia-lyase (TAL) polypeptides and compositions thereof. In some embodiments, the engineered TAL polypeptides have been optimized to provide enhanced catalytic activity while reducing sensitivity to proteolysis. The invention also provides methods for utilization of the compositions comprising the engineered TAL polypeptides for therapeutic and industrial purposes.

Abbreviations and Definitions

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value. In some instances, "about" encompasses values that are within 2.5%, 3%, 3.5%, 4%, 4.5%, 5%, 5.5%, 6%, 6.5%, 7%, 7.5%, 8%, 8.5%, 9%, 9.5%, or 10% of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein, the terms "tyrosine ammonia-lyase" "tyrosine ammonia lyase," "tyrosine ammonia lyase polypeptide" and "TAL" refer to a class of enzymes within the aromatic amino acid lyase family (EC 4.3.1.23, EC 4.3.1.24 and EC4.3.1.25) which also includes histidine ammonia-lyase, and phenylalanine ammonia-lyase.

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The term "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example a wild-type polypeptide or polynucleotide sequence is a sequence present in an organism that can be isolated from a source in nature and which has not been intentionally modified by human manipulation.

"Deimmunized" as used herein, refers to the manipulation of a protein to create a variant that is not as immunogenic as the wild-type or reference protein. In some embodiments, the deimmunization is complete, in that the variant protein does not stimulate an immune response in patients to whom the variant protein is administered. This response can be measured by various methods including but not limited to, the presence or abundance of anti-drug antibodies, the presence or abundance of neutralizing antibodies, the presence of an anaphylactic response, or the prevalence or intensity of cytokine release upon administration of the protein. In some embodiments, the variant protein is less immunogenic than the wild-type or reference protein. In some embodiments, deimmunization involves modifications to proteins (e.g., epitopes) that are recognized by T-cell receptors. In some embodiments, the T-cell epitopes are removed from a wild-type or reference protein in order to produce a deimmunized variant protein. In some embodiments, the deimmunized protein shows lower levels of response in biochemical and cell-biological predictors of human immunological responses including dendritic-cell T-cell activation assays, or human leukocyte antigen (HLA) peptide binding assays.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970], by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See, Altschul et al., J. Mol. Biol., 215: 403-410 [1990]; and Altschul et al., 1977, Nucleic Acids Res., 3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered TAL, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X93 as compared to SEQ ID NO:10" refers to a difference of the amino acid residue at the polypeptide position corresponding to position 93 of SEQ ID NO:10. Thus, if the reference polypeptide of SEQ ID NO:10 has a serine at position 93, then a "residue difference at position X93 as compared to SEQ ID NO:10" an amino acid substitution of any residue other than serine at the position of the polypeptide corresponding to position 93 of SEQ ID NO:10. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in Table 4-1), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "I" (e.g., X307H/X307P or X307H/P). The present application includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

A "functional fragment" or a "biologically active fragment" used interchangeably herein refers to a polypeptide that has an amino-terminal and/or carboxy-terminal deletion (s) and/or internal deletions, but where the remaining amino acid sequence is identical to the corresponding positions in the sequence to which it is being compared (e.g., a full-length engineered TAL of the present invention) and that retains substantially all of the activity of the full-length polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The recombinant TAL polypeptides may be present within a cell, present in the cellular medium, or prepared in various forms, such as lysates or isolated preparations. As such, in some embodiments, the recombinant TAL polypeptides can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure TAL composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant TAL polypeptides are substantially pure polypeptide compositions.

"Improved enzyme property" refers to an engineered TAL polypeptide that exhibits an improvement in any enzyme property as compared to a reference TAL polypeptide and/or as a wild-type PAL polypeptide (e.g., the wild-type AvPAL of SEQ ID NO:4) or another engineered TAL polypeptide. Improved properties include but are not limited to such properties as increased protein expression, increased thermoactivity, increased thermostability, increased pH activity, increased stability, increased enzymatic activity, increased substrate specificity or affinity, increased specific activity, increased resistance to substrate or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, reduced immunogenicity, and altered temperature profile.

"Increased enzymatic activity" or "enhanced catalytic activity" refers to an improved property of the engineered TAL polypeptides, which can be represented by an increase in specific activity (e.g., product produced/time/weight protein) or an increase in percent conversion of the substrate to the product (e.g., percent conversion of starting amount of substrate to product in a specified time period using a specified amount of TAL) as compared to the reference TAL enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring TAL or another engineered TAL from which the TAL polypeptides were derived.

In some embodiments, the engineered TAL polypeptides have a $k_{cat}$ of at least 0.1/sec, at least 0.2/sec, at least 0.3/sec, at least 0.5/sec, at least 1.0/sec and in some preferred embodiments greater than 1.0/sec. In some embodiments, the $K_m$ is in the range of about 1 μm to about 5 mM; in the range of about 5 μm to about 2 mM; in the range of about 10 μm to about 2 mM; or in the range of about 10 μm to about 1 mM. In some specific embodiments, the engineered TAL enzyme exhibits improved enzymatic activity in the range of 1.5 to 10 fold, 1.5 to 25 fold, 1.5 to 50 fold, 1.5 to 100 fold or greater than that of a reference TAL enzyme (e.g., a wild-type TAL or any other reference TAL). TAL activity can be measured by any suitable method known in the art (e.g., standard assays, such as monitoring changes in spectrophotometric properties of reactants or products). In some embodiments, the amount of products produced can be measured by High-Performance Liquid Chromatography (HPLC) separation combined with UV absorbance or fluorescent detection directly or following o-phthaldialdehyde (OPA) derivatization. In some embodiments, other methods are used, such as tracking the coumarate product (e.g., use UV absorbance to track its production at 290 nm or 310 nm). In some other embodiments, the production of ammonia is assayed using commercially available kits (e.g., the Megazyme rapid ammonia assay kit [Megazyme International, Wicklow, Ireland]). Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

The terms "thermally stable" and "thermostable" refer to enzymes of the present invention that retain a specified amount of enzymatic activity, primary, secondary, tertiary and quaternary structure after exposure to an identified temperatures over a given period of time under conditions prevailing during the use of the enzyme, for example, when exposed to altered temperatures. "Altered temperatures" include increased or decreased temperatures. In some embodiments, the enzymes retain at least about 50%, about 60%, about 70%, about 75%, about 80%, about 85%, about 90%, about 92%, about 95%, about 96%, about 97%, about 98%, or about 99% enzymatic activity after exposure to altered temperatures over a given time period, for example, at least about 60 minutes, about 120 minutes, about 180 minutes, about 240 minutes, about 300 minutes, etc.

The term "improved tolerance to acidic pH" means that a recombinant TAL according to the invention will have increased stability (higher retained activity at about pH 7.0 after exposure to acidic pH for a specified period of time (1 hour, up to 24 hours)) as compared to a reference TAL or another enzyme.

"Physiological pH" as used herein means the pH range generally found in a subject's (e.g., human) small intestine. There normally is a pH gradient from the pyloric sphincter to the large intestine from about 5.0 to 7.5.

The term "acidic pH" (e.g., used with reference to improved stability to acidic pH conditions or increased tolerance to acidic pH) means a pH range of about 1.5 to 6.8.

The terms "proteolytic activity" and "proteolysis" used interchangeably herein refer to the breakdown of proteins into smaller polypeptides or amino acids. The breakdown of proteins is generally the result of hydrolysis of the peptide bond by protease (proteinase) enzymes. Protease enzymes include but are not limited to pepsin, trypsin, chymotrypsin, elastase, carboxypeptidase A and B, peptidases (e.g., amino peptidase, dipeptidase and enteropeptidase).

The phrases "reducing sensitivity to proteolysis" and "reducing proteolytic sensitivity" used interchangeably herein mean that an engineered TAL polypeptide according to the invention will have a higher enzyme activity compared to a reference TAL and/or another enzyme in a standard assay after treatment with one or more proteases. Exemplary assays are provided in the Examples.

"Aggregation" means clumping or precipitation of a TAL polypeptide. Aggregation can lead to inactivation, and/or increased immunogenicity of the enzyme. The term "reduced aggregation" means an engineered TAL polypeptide will be less prone to aggregation or to aggregate than a reference TAL and/or another enzyme. Methods for determining Aggregation can be determined by one of general skill in the art by using any number of assays including but not limited to fluorescent microscopy with appropriate dyes (e.g., thioflavin T or Nile Red), dynamic light scattering, flow cytometry with appropriate dyes (e.g. Bodipy), filtration and analysis by SDS-PAGE or Western blotting, fluorescent correlation spectroscopy, and electron microscopy. There are commercially available kits to assess aggregation (e.g., the ProteoStat® Protein Aggregation Assay kit [Enzo]).

"Conversion" refers to the enzymatic conversion (or biotransformation) of a substrate(s) to the corresponding product(s). "Percent conversion" refers to the percent of the substrate that is converted to the product within a period of time under specified conditions. Thus, the "enzymatic activity" or "activity" of a TAL polypeptide can be expressed as "percent conversion" of the substrate to the product in a specific period of time.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the TAL enzymes may be codon optimized for optimal production from the host organism selected for expression.

"Control sequence" refers herein to include all components, which are necessary or advantageous for the expression of a polynucleotide and/or polypeptide of the present application. Each control sequence may be native or foreign to the nucleic acid sequence encoding the polypeptide. Such control sequences include, but are not limited to, a leader, polyadenylation sequence, propeptide sequence, promoter sequence, signal peptide sequence, initiation sequence and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refers to those conditions in the enzymatic conversion reaction solution (e.g., ranges of enzyme loading, substrate loading, temperature, pH, buffers, co-solvents, etc.) under which a TAL polypeptide of the present application is capable of converting a substrate to the desired product compound, Exemplary "suitable reaction conditions" are provided in the present application and illustrated by the Examples. "Loading", such as in "compound loading" or "enzyme loading" refers to the concentration or amount of a component in a reaction mixture at the start of the reaction. "Substrate" in the context of an enzymatic conversion reaction process refers to the compound or molecule acted on by the TAL polypeptide. "Product" in the context of an enzymatic conversion process refers to the compound or molecule resulting from the action of the TAL polypeptide on a substrate.

As used herein the term "culturing" refers to the growing of a population of microbial cells under any suitable conditions (e.g., using a liquid, gel or solid medium).

Recombinant polypeptides can be produced using any suitable methods known the art. Genes encoding the wild-type polypeptide of interest can be cloned in vectors, such as plasmids, and expressed in desired hosts, such as E. coli, etc. Variants of recombinant polypeptides can be generated by various methods known in the art. Indeed, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant TAL polypeptides" (also referred to herein as "engineered TAL polypeptides," "variant TAL enzymes," and "TAL variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., the polynucleotides encoding the TAL variants). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues means polypeptides that contain one or more non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "therapeutic" refers to a compound administered to a subject who shows signs or symptoms of pathology having beneficial or desirable medical effects.

The term "pharmaceutical composition" refers to a composition suitable for pharmaceutical use in a mammalian subject (e.g., human) comprising a pharmaceutically effective amount of an engineered TAL polypeptide encompassed by the invention and an acceptable carrier.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

The term "subject" encompasses mammals such as humans, non-human primates, livestock, companion animals, and laboratory animals (e.g., rodents and lagamorphs). It is intended that the term encompass females as well as males.

As used herein, the term "patient" means any subject that is being assessed for, treated for, or is experiencing disease.

The term "infant" refers to a child in the period of the first month after birth to approximately one (1) year of age. As used herein, the term "newborn" refers to child in the period from birth to the 28$^{th}$ day of life. The term "premature infant" refers to an infant born after the twentieth completed week of gestation, yet before full term, generally weighing ~500 to ~2499 grams at birth. A "very low birth weight infant" is an infant weighing less than 1500 g at birth.

As used herein, the term "child" refers to a person who has not attained the legal age for consent to treatment or research procedures. In some embodiments, the term refers to a person between the time of birth and adolescence.

As used herein, the term "adult" refers to a person who has attained legal age for the relevant jurisdiction (e.g., 18 years of age in the United States). In some embodiments, the term refers to any fully grown, mature organism. In some embodiments, the term "young adult" refers to a person less than 18 years of age, but who has reached sexual maturity.

As used herein, "composition" and "formulation" encompass products comprising at least one engineered TAL of the present invention, intended for any suitable use (e.g., pharmaceutical compositions, dietary/nutritional supplements, feed, etc.).

The terms "administration" and "administering" a composition mean providing a composition of the present invention to a subject (e.g., to a person suffering from the effects of tyrosinemia or alkaptonuria).

The term "carrier" when used in reference to a pharmaceutical composition means any of the standard pharmaceutical carrier, buffers, and excipients, such as stabilizers, preservatives, and adjuvants.

The term "pharmaceutically acceptable" means a material that can be administered to a subject without causing any undesirable biological effects or interacting in a deleterious manner with any of the components in which it is contained and that possesses the desired biological activity.

As used herein, the term "excipient" refers to any pharmaceutically acceptable additive, carrier, diluent, adjuvant, or other ingredient, other than the active pharmaceutical ingredient (API; e.g., the engineered TAL polypeptides of the present invention). Excipients are typically included for formulation and/or administration purposes.

The term "therapeutically effective amount" when used in reference to symptoms of disease/condition refers to the amount and/or concentration of a compound (e.g., engineered TAL polypeptides) that ameliorates, attenuates, or eliminates one or more symptom of a disease/condition or prevents or delays the onset of symptom(s).

The term "therapeutically effective amount" when used in reference to a disease/condition refers to the amount and/or concentration of a composition (e.g., engineered TAL polypeptides) that ameliorates, attenuates, or eliminates the disease/condition. In some embodiments, the term is use in reference to the amount of a composition that elicits the biological (e.g., medical) response by a tissue, system, or animal subject that is sought by the researcher, physician, veterinarian, or other clinician.

It is intended that the terms "treating," "treat" and "treatment" encompass preventative (e.g., prophylactic), as well as palliative treatment.

Engineered TAL Polypeptides:

The parent enzyme used to generate the engineered TAL polypeptides is a PAL obtained from *Anabaena variabilis*. In some embodiments, alternative enzymes find use as parent enzymes to generate engineered TAL polypeptides (e.g., *Nostoc punctiforme* phenylalanine/histidine ammonia lyase "NpPHAL" (NCBI YP_001865631.1; *Rivularia* sp. histidine ammonia-lyase "RspHAL" (NCBI YP_007056096.1; *Oscillatoria* sp. histidine ammonia-lyase "Osp HAL" (NCBI YP_07108482.1; and *Gloeocapsa* sp. histidine ammonialyase "GspHAL" (NCBI YP_007127054.1). Furthermore, when a particular TAL variant (engineered TAL polypeptide) is referred to by reference to modification of particular amino acids residues in the sequence of a wild-type TAL, wild-type PAL, wild-type HAL or another TAL, it is to be understood that variants of another TAL modified in the equivalent position(s) (as determined from the optional amino acid sequence alignment between the respective amino acid sequences) are encompassed herein. In some embodiments the engineered TAL polypeptide will comprise the conserved active site Ala167-Ser168-Gly169 and comprise at least 70% (at least 75%, at least 80%, at least 85%, at least 90%, at least 93%, at least 95%, at least 97%) sequence identity to SEQ ID NO:4. In some embodiments the engineered TAL polypeptides will comprise not only TAL activity but also may be active on phenylalanine and/or histidine substrates. In some embodiments, TAL variants are developed that comprise at least one mutation in at least one key residue (e.g., position 107; See e.g., WO 2008/069958; US Appln. Ser. No. 2009/011140; and Watts et al. Chem. Biol., 13:1317-26 [2006])

In some embodiments, engineered TAL polypeptides are produced by cultivating a microorganism comprising at least one polynucleotide sequence encoding at least one engineered TAL polypeptide under conditions which are conducive for producing the engineered TAL polypeptide(s). In some embodiments, the engineered TAL polypeptide is recovered from the resulting culture medium and/or cells.

The present invention provides exemplary engineered TAL polypeptides having TAL activity. The Examples provide Tables showing sequence structural information correlating specific amino acid sequence features with the functional activity of the engineered TAL polypeptides. This structure-function correlation information is provided in the form of specific amino acid residues differences relative to a reference engineered polypeptide, as indicated in the Examples. The Examples further provide experimentally determined activity data for the exemplary engineered TAL polypeptides.

In some embodiments, the engineered TAL polypeptides of the invention having TAL activity comprise a) an amino acid sequence having at least 85% sequence identity to reference sequence SEQ ID NO:6; b) an amino acid residue difference as compared to SEQ ID NO:6 at one or more amino acid positions; and c) which exhibits an improved property selected from i) enhanced catalytic activity, ii) reduced proteolytic sensitivity, iii) increased tolerance to acidic pH, iv) reduced aggregation or a combination of any of i), ii), iii) or iv), as compared to the reference sequence.

In some embodiments the engineered TAL which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:6, and an amino acid residue difference as compared to SEQ ID NO:6, at one or more amino acid positions (e.g., at 1, 2, 3, 4, 5, 6, 7, 8, 9, 10, 11, 12, 14, 15, 20 or more amino acid positions compared to SEQ ID NO:6, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6). In some embodiment the residue difference as compared to SEQ ID NO:6, at one or more positions will include at least 1, 2, 3, 4, 5, 6, 7, 8, 9, 10 or more conservative amino acid substitutions. In some embodiments the engineered TAL which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:6.

In some embodiments, the engineered TAL polypeptides of the invention having TAL activity comprise a) an amino acid sequence having at least 85% sequence identity to reference sequence SEQ ID NO:8; b) an amino acid residue difference as compared to SEQ ID NO:8 at one or more amino acid positions; and c) which exhibits an improved property selected from i) enhanced catalytic activity, ii) reduced proteolytic sensitivity, iii) increased tolerance to acidic pH, iv) reduced aggregation or a combination of any of i), ii), iii) or iv), as compared to the reference sequence.

In some embodiments the engineered TAL which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:8, and an amino acid residue difference as compared to SEQ ID NO:8, at one or more amino acid positions (e.g., at 1, 2, 3, 4, 5, 6, 7, 8, 9, 10, 11, 12, 14, 15, 20 or more amino acid positions compared to SEQ ID NO:8, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8). In some embodiment the residue difference as compared to SEQ ID NO:8, at one or more positions will include at least 1, 2, 3, 4, 5, 6, 7, 8, 9, 10 or more conservative amino acid substitutions. In some embodiments the engineered TAL which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:8.

In some embodiments, the engineered TAL polypeptides of the invention having TAL activity comprise a) an amino acid sequence having at least 85% sequence identity to reference sequence SEQ ID NO:10; b) an amino acid residue difference as compared to SEQ ID NO:10 at one or more amino acid positions; and c) which exhibits an improved property selected from i) enhanced catalytic activity, ii) reduced proteolytic sensitivity, iii) increased tolerance to acidic pH, iv) reduced aggregation or a combination of any of i), ii), iii) or iv), as compared to the reference sequence.

In some embodiments the engineered TAL which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:10, and an amino acid residue difference as compared to SEQ ID NO:10, at one or more amino acid positions (e.g., at 1, 2, 3, 4, 5, 6, 7, 8, 9, 10, 11, 12, 14, 15, 20 or more amino acid positions compared to SEQ ID NO:10, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10). In some embodiment the residue difference as compared to SEQ ID NO:10, at one or more positions will include at least 1, 2, 3, 4, 5, 6, 7, 8, 9, 10 or more conservative amino acid substitutions. In some embodiments, the engineered TAL polypeptide is a polypeptide listed in Table 4-1, 4-2, 4-3, 4-4, 4-5, 4-6, and/or 4-7. In some embodiments the engineered TAL which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:10.

In some embodiments, the engineered TAL polypeptides of the invention having TAL activity comprise a) an amino acid sequence having at least 85% sequence identity to reference sequence SEQ ID NO:12; b) an amino acid residue difference as compared to SEQ ID NO:12 at one or more amino acid positions; and c) which exhibits an improved property selected from i) enhanced catalytic activity, ii) reduced proteolytic sensitivity, iii) increased tolerance to acidic pH, iv) reduced aggregation or a combination of any of i), ii), iii) or iv), as compared to the reference sequence.

In some embodiments the engineered TAL which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:12, and an amino acid residue difference as compared to SEQ ID NO:12, at one or more amino acid positions (e.g., at 1, 2, 3, 4, 5, 6, 7, 8, 9, 10, 11, 12, 14, 15, 20 or more amino acid positions compared to SEQ ID NO:12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12). In some embodiment the residue difference as compared to SEQ ID NO:12, at one or more positions will include at least 1, 2, 3, 4, 5, 6, 7, 8, 9, 10 or more conservative amino acid substitutions. In some embodiments the engineered TAL which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:12.

In some embodiments, the engineered TAL polypeptides of the invention having TAL activity comprise a) an amino acid sequence having at least 85% sequence identity to reference sequence SEQ ID NO:14; b) an amino acid residue difference as compared to SEQ ID NO:14 at one or more amino acid positions; and c) which exhibits an improved property selected from i) enhanced catalytic activity, ii) reduced proteolytic sensitivity, iii) increased tolerance to acidic pH, iv) reduced aggregation or a combination of any of i), ii), iii) or iv), as compared to the reference sequence.

In some embodiments the engineered TAL which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:14, and an amino acid residue difference as compared to SEQ ID NO:14, at one or more amino acid positions (e.g., at 1, 2, 3, 4, 5, 6, 7, 8, 9, 10, 11, 12, 14, 15, 20 or more amino acid positions compared to SEQ ID NO:14, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14). In some embodiment the residue difference as compared to SEQ ID NO:14, at one or more positions will include at least 1, 2, 3, 4, 5, 6, 7, 8, 9, 10 or more conservative amino acid substitutions. In some embodiments, the engineered TAL polypeptide is a polypeptide listed in Tables 4-1, 4-2, 4-3, 4-4, 4-5, 4-6, and/or 4-7. In some embodiments the engineered TAL which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:14.

In some embodiments, the engineered TAL polypeptide comprises a functional fragment of an engineered TAL polypeptide encompassed by the invention. Functional fragments have at least 95%, 96%, 97%, 98%, or 99% of the activity of the engineered TAL polypeptide from which is was derived (i.e., the parent engineered TAL). A functional fragment comprises at least 90%, 91%, 92%, 93%, 94%, 95%, 96%, 97%, 98% and even 99% of the parent sequence of the engineered TAL. In some embodiments the functional fragment is truncated by less than 5, less than 10, less than 15, less than 10, less than 25, less than 30, less than 35, less than 40, less than 45, and less than 50 amino acids.

Variants with Reduced Sensitivity to Proteolysis:

In some embodiments, the engineered TAL polypeptides of the invention having TAL activity comprise a) an amino acid sequence having at least 85% sequence identity to reference sequence SEQ ID NO:6; b) an amino acid residue difference as compared to SEQ ID NO:6 at one or more amino acid positions; and c) which exhibits reduced sensitivity to proteolysis.

In some embodiments the engineered TAL which exhibits reduced sensitivity to proteolysis has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6 and an amino acid residue difference as compared to SEQ ID NO:6 at one or more amino acid positions (e.g., at 1, 2, 3, 4, 5, 6, 7, 8, 9, 10, 11, 12, 14, 15, 20 or more amino acid positions compared to SEQ ID NO:6 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6).

In some embodiments, the engineered TAL polypeptides of the invention having TAL activity comprise a) an amino acid sequence having at least 85% sequence identity to reference sequence SEQ ID NO:8; b) an amino acid residue difference as compared to SEQ ID NO:8 at one or more amino acid positions; and c) which exhibits reduced sensitivity to proteolysis.

In some embodiments the engineered TAL which exhibits reduced sensitivity to proteolysis has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8 and an amino acid residue difference as compared to SEQ ID NO:8 at one or more amino acid positions (e.g., at 1, 2, 3, 4, 5, 6, 7, 8, 9, 10, 11, 12, 14, 15, 20 or more amino acid positions compared to SEQ ID NO:8 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8).

In some embodiments, the engineered TAL polypeptides of the invention having TAL activity comprise a) an amino acid sequence having at least 85% sequence identity to reference sequence SEQ ID NO:8; b) an amino acid residue difference as compared to SEQ ID NO:8 at one or more amino acid positions; and c) which exhibits reduced sensitivity to proteolysis.

In some embodiments the engineered TAL which exhibits reduced sensitivity to proteolysis has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8 and an amino acid residue difference as compared to SEQ ID NO:8 at one or more amino acid positions (e.g., at 1, 2, 3, 4, 5, 6, 7, 8, 9, 10, 11, 12, 14, 15, 20 or more amino acid positions compared to SEQ ID NO:8 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8).

In some embodiments, the engineered TAL polypeptides of the invention having TAL activity comprise a) an amino acid sequence having at least 85% sequence identity to reference sequence SEQ ID NO:10; b) an amino acid residue difference as compared to SEQ ID NO:10 at one or more amino acid positions; and c) which exhibits reduced sensitivity to proteolysis.

In some embodiments the engineered TAL which exhibits reduced sensitivity to proteolysis has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10 and an amino acid residue difference as compared to SEQ ID NO:10 at one or more amino acid positions (e.g., at 1, 2, 3, 4, 5, 6, 7, 8, 9, 10, 11, 12, 14, 15, 20 or more amino acid positions compared to SEQ ID NO:10 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10).

In some embodiments, the engineered TAL polypeptides of the invention having TAL activity comprise a) an amino acid sequence having at least 85% sequence identity to reference sequence SEQ ID NO:12; b) an amino acid residue difference as compared to SEQ ID NO:12 at one or more amino acid positions; and c) which exhibits reduced sensitivity to proteolysis.

In some embodiments the engineered TAL which exhibits reduced sensitivity to proteolysis has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12 and an amino acid residue difference as compared to SEQ ID NO:12 at one or more amino acid positions (e.g., at 1, 2, 3, 4, 5, 6, 7, 8, 9, 10, 11, 12, 14, 15, 20 or more amino acid positions compared to SEQ ID NO:12 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12).

In some embodiments, the engineered TAL polypeptides of the invention having TAL activity comprise a) an amino acid sequence having at least 85% sequence identity to reference sequence SEQ ID NO:14; b) an amino acid residue difference as compared to SEQ ID NO:14 at one or more amino acid positions; and c) which exhibits reduced sensitivity to proteolysis.

In some embodiments the engineered TAL which exhibits reduced sensitivity to proteolysis has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14 and an amino acid residue difference as compared to SEQ ID NO:14 at one or more amino acid positions (e.g., at 1, 2, 3, 4, 5, 6, 7, 8, 9, 10, 11, 12, 14, 15, 20 or more amino acid positions compared to SEQ ID NO:14 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14).

In some embodiments, the proteolytic sensitivity of the engineered TAL polypeptide will be reduced by at least 5%, at least 10%, at least 15%, at least 20%, at least 25%, at least 30%, at least 40%, at least 50%, at least 60%, at least 70%, at least 80% and at least 85% compared to the wild-type AvPAL and/or at least one reference TAL polypeptide under essentially the same conditions. The proteolytic sensitivity can be measured using any suitable assay system, including, but not limited to the assays described in the Examples.

In some embodiments, the engineered TAL polypeptide having reduced sensitivity to proteolysis has reduced sensitivity to a composition comprising one or more proteases such as but not limited to pepsin, trypsin, chymotrypsin, carboxypeptidase A and B, peptidases (e.g., amino peptidase, dipeptidase and enteropeptidase) when both the reference TAL and the engineered TAL having the reduced sensitivity are compared and exposed to essentially the same amount and kind of protease under essentially the same conditions.

In some embodiments, the engineered TAL polypeptide having reduced sensitivity to proteolysis has enzyme activity that is about 1.0 fold, 2-fold, 5-fold, 10-fold, 20-fold, 25-fold, 50-fold, 75-fold, 100-fold, 150-fold, 200-fold or more of the enzymatic activity of the reference TAL. In some embodiments, the engineered polypeptides will have more enzyme activity (as compared to a reference TAL) when activity is measured at a pH range of 4.5 to 7.5; when activity is measured at a pH range of 4.5 to 6.5; when activity is measured at a pH range of 5.0 to 7.5, when activity is measured at a pH range of 5.0 to 6.5; when activity is measured at a pH range of 5.5 to 7.5 and also when activity is measured at a pH range of 5.5 to 6.5. In other embodiments, the engineered TAL polypeptides will have a $K_m$ in the range of 1 µM to 5 mM.

Variants with Increased Tolerance to Acidic pH:

In some embodiments, the engineered TAL polypeptides of the invention having TAL activity comprise a) an amino acid sequence having at least 85% sequence identity to reference sequence SEQ ID NO:6, or a fragment thereof; b) an amino acid residue difference as compared to SEQ ID NO:6, at one or more amino acid positions; and c) which exhibits increased tolerance to acidic pH.

In some embodiments, the engineered TAL that exhibits increased tolerance to acidic pH has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6 and an amino acid residue difference as compared to SEQ ID NO:6, at one or more amino acid positions (e.g., at 1, 2, 3, 4, 5, 6, 7, 8, 9, 10, 11, 12, 14, 15, 20 or more amino acid positions compared to SEQ ID NO:6, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6.

In some embodiments, the engineered TAL polypeptides of the invention having TAL activity comprise a) an amino acid sequence having at least 85% sequence identity to reference sequence SEQ ID NO:8, or a fragment thereof; b) an amino acid residue difference as compared to SEQ ID NO:8, at one or more amino acid positions; and c) which exhibits increased tolerance to acidic pH.

In some embodiments, the engineered TAL that exhibits increased tolerance to acidic pH has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8 and an amino acid residue difference as compared to SEQ ID NO:8, at one or more amino acid positions (e.g., at 1, 2, 3, 4, 5, 6, 7, 8, 9, 10, 11, 12, 14, 15, 20 or more amino acid positions compared to SEQ ID NO:8, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8.

In some embodiments, the engineered TAL polypeptides of the invention having TAL activity comprise a) an amino acid sequence having at least 85% sequence identity to reference sequence SEQ ID NO:10, or a fragment thereof; b) an amino acid residue difference as compared to SEQ ID NO:10, at one or more amino acid positions; and c) which exhibits increased tolerance to acidic pH.

In some embodiments, the engineered TAL that exhibits increased tolerance to acidic pH has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10 and an amino acid residue difference as compared to SEQ ID NO:10, at one or more amino acid positions (e.g., at 1, 2, 3, 4, 5, 6, 7, 8, 9, 10, 11, 12, 14, 15, 20 or more amino acid positions compared to SEQ ID NO:10, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10.

In some embodiments, the engineered TAL polypeptides of the invention having TAL activity comprise a) an amino acid sequence having at least 85% sequence identity to reference sequence SEQ ID NO:12, or a fragment thereof; b) an amino acid residue difference as compared to SEQ ID NO:12, at one or more amino acid positions; and c) which exhibits increased tolerance to acidic pH.

In some embodiments, the engineered TAL that exhibits increased tolerance to acidic pH has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12 and an amino acid residue difference as compared to SEQ ID NO:12, at one or more amino acid positions (e.g., at 1, 2, 3, 4, 5, 6, 7, 8, 9, 10, 11, 12, 14, 15, 20 or more amino acid positions compared to SEQ ID NO:12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12.

In some embodiments, the engineered TAL polypeptides of the invention having TAL activity comprise a) an amino acid sequence having at least 85% sequence identity to reference sequence SEQ ID NO:14, or a fragment thereof; b) an amino acid residue difference as compared to SEQ ID NO:14, at one or more amino acid positions; and c) which exhibits increased tolerance to acidic pH.

In some embodiments, the engineered TAL that exhibits increased tolerance to acidic pH has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14 and an amino acid residue difference as compared to SEQ ID NO:14, at one or more amino acid positions (e.g., at 1, 2, 3, 4, 5, 6, 7, 8, 9, 10, 11, 12, 14, 15, 20 or more amino acid positions compared to SEQ ID NO:14, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14.

In some embodiments, when all other assay conditions are essentially the same, the engineered TAL polypeptide has increased tolerance to acidic pH as compared to a reference TAL polypeptide. The engineered peptide has an increased tolerance at a pH range between 1.5 to 6.5, and between 1.5 and 5.0, and between 2.0 to 5.5, and between 3.0 and 6.8; between 3.0 and 5.5; between 4.0 and 6.5; between 4.0 and 4.5; between 4.5 and between 5.0; between 4.5 and 5.5, between 4.5 and 6.0; between 4.5 and 6.5; between 5.0 and 6.5; between 5.0 and 6.0; between 5.0 and 5.5; between 5.5 and 6.0; between 6.0 and 6.5 and between 6.5 and 7.0. In some embodiments the increased tolerance to acidic pH will be exhibited at a pH of about 3.5, 4.0, 4.5, 5.0, 5.5, 6.0 and 6.5.

In some embodiments, the engineered TAL polypeptide having increased tolerance to acidic pH exhibits greater TAL activity as compared to a reference TAL when measured by any standard assay, including, but not limited to the assays described in the Examples.

Variants with Improved Activity:

In some embodiments, the engineered TAL polypeptides of the invention having TAL activity comprise a) an amino acid sequence having at least 85% sequence identity to reference sequence SEQ ID NO:6, or a fragment thereof; b) an amino acid residue difference as compared to SEQ ID NO:6, at one or more amino acid positions; and c) which exhibits improved activity, as compared to SEQ ID NO:6.

In some embodiments, the engineered TAL that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6 and an amino acid residue difference as compared to SEQ ID NO:6, at one or more amino acid positions (e.g., at 1, 2, 3, 4, 5, 6, 7, 8, 9, 10, 11, 12, 14, 15, 20 or more amino acid positions compared to SEQ ID NO:6, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6.

In some embodiments, the engineered TAL polypeptides of the invention having TAL activity comprise a) an amino acid sequence having at least 85% sequence identity to reference sequence SEQ ID NO:8, or a fragment thereof; b) an amino acid residue difference as compared to SEQ ID NO:8, at one or more amino acid positions; and c) which exhibits improved activity, as compared to SEQ ID NO:8.

In some embodiments, the engineered TAL that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8 and an amino acid residue difference as compared to SEQ ID NO:8, at one or more amino acid positions (e.g., at 1, 2, 3, 4, 5, 6, 7, 8, 9, 10, 11, 12, 14, 15, 20 or more amino acid positions compared to SEQ ID NO:8, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:8.

In some embodiments, the engineered TAL polypeptides of the invention having TAL activity comprise a) an amino acid sequence having at least 85% sequence identity to reference sequence SEQ ID NO:10, or a fragment thereof; b) an amino acid residue difference as compared to SEQ ID NO:10, at one or more amino acid positions; and c) which exhibits improved activity, as compared to SEQ ID NO:10.

In some embodiments, the engineered TAL that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10 and an amino acid residue difference as compared to SEQ ID NO:10, at one or more amino acid positions (e.g., at 1, 2, 3, 4, 5, 6, 7, 8, 9, 10, 11, 12, 14, 15, 20 or more amino acid positions compared to SEQ ID NO:10, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10.

In some embodiments, the engineered TAL polypeptides of the invention having TAL activity comprise a) an amino acid sequence having at least 85% sequence identity to reference sequence SEQ ID NO:12, or a fragment thereof; b) an amino acid residue difference as compared to SEQ ID NO:12, at one or more amino acid positions; and c) which exhibits improved activity, as compared to SEQ ID NO:12.

In some embodiments, the engineered TAL that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12 and an amino acid residue difference as compared to SEQ ID NO:12, at one or more amino acid positions (e.g., at 1, 2, 3, 4, 5, 6, 7, 8, 9, 10, 11, 12, 14, 15, 20 or more amino acid positions compared to SEQ ID NO:12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12.

In some embodiments, the engineered TAL polypeptides of the invention having TAL activity comprise a) an amino acid sequence having at least 85% sequence identity to reference sequence SEQ ID NO:14, or a fragment thereof; b) an amino acid residue difference as compared to SEQ ID NO:14, at one or more amino acid positions; and c) which exhibits improved activity, as compared to SEQ ID NO:14.

In some embodiments, the engineered TAL that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14 and an amino acid residue difference as compared to SEQ ID NO:14, at one or more amino acid positions (e.g., at 1, 2, 3, 4, 5, 6, 7, 8, 9, 10, 11, 12, 14, 15, 20 or more amino acid positions compared to SEQ ID NO:14, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14.

In some embodiments, when all other assay conditions are essentially the same, the engineered TAL polypeptide has improved activity as compared to a reference TAL polypeptide. In some embodiments this activity can be measured under conditions that monitor enzymatic activity at saturating levels of tyrosine, thus assessing the maximum activity of the enzyme ($k_{cat}$). In other embodiments this activity can be measured under substrate concentrations resulting in one-half, one-fifth, one-tenth or less of maximal activity. Under either method of analysis, the engineered polypeptide has improved activity levels about 1.0 fold, 1.5-fold, 2-fold, 5-fold, 10-fold, 20-fold, 25-fold, 50-fold, 75-fold, 100-fold, or more of the enzymatic activity of the reference TAL In some embodiments, the engineered TAL polypeptide having improved activity as compared to a reference TAL when measured by any standard assay, including, but not limited to the assays described in the Examples.

In light of the guidance provided herein, it is further contemplated that any of the exemplary engineered polypeptides (e.g., SEQ ID NOS:6, 8, 10, 12, and 14) can be used as the starting amino acid sequence for synthesizing other engineered TAL polypeptides, for example by subsequent rounds of evolution by adding new combinations of various amino acid differences from other polypeptides and other residue positions described herein. Further improvements may be generated by including amino acid differences at residue positions that had been maintained as unchanged throughout earlier rounds of evolution.

Polynucleotides Encoding Engineered Polypeptides, Expression Vectors and Host Cells:

The present invention provides polynucleotides encoding the engineered TAL polypeptides described herein. In some embodiments, the polynucleotides are operatively linked to one or more heterologous regulatory sequences that control gene expression to create a recombinant polynucleotide capable of expressing the polypeptide. Expression constructs containing a heterologous polynucleotide encoding the engineered TAL polypeptides can be introduced into appropriate host cells to express the corresponding TAL polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the engineered TAL polypeptide. Thus, having knowledge of a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made encoding the polypeptides described herein by selecting combinations based on the possible codon choices, and all such variations are to be considered specifically disclosed for any polypeptide described herein, including the variants provided in Table 4-1, as well as SEQ ID NOS:8 and 10.

In various embodiments, the codons are preferably selected to fit the host cell in which the protein is being produced. For example, preferred codons used in bacteria are used for expression in bacteria. Consequently, codon optimized polynucleotides encoding the engineered TAL polypeptides contain preferred codons at about 40%, 50%, 60%, 70%, 80%, or greater than 90% of codon positions of the full length coding region.

In some embodiments, as described above, the polynucleotide encodes an engineered polypeptide having TAL activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NOS:6, 8, 10, 12, and/or 14, or the amino acid sequence of any variant as disclosed in Tables 4-1, 4-2, 4-3, 4-4, 4-5, 4-6, and/or 4-7, and one or more residue differences as compared to the reference polypeptide of SEQ ID NOS:6, 8, 10, 12, and/or 14, or the amino acid sequence of any variant as disclosed in Table 4-1, 4-2, 4-3, 4-4, 4-5, 4-6, and/or 4-7 (e.g., 1, 2, 3, 4, 5, 6, 7, 8, 9, 10 or more amino acid residue positions). In some embodiments, the reference sequence is selected from SEQ ID NOS:6, 8, 10, 12, and/or 14.

In some embodiments, the polynucleotide encodes an engineered polypeptide having TAL activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:6, and one or more residue differences as compared to SEQ ID NO:10 at residue positions selected from 73, 77, 88, 91, 93, 95, 97, 108, 222, 253, 304, 307, 315, 364, 389, 400, 401, 453, and/or 490, when optimally aligned with the polypeptide of SEQ ID NO:10.

In some embodiments, the polynucleotide encoding the engineered TAL polypeptides comprises a polynucleotide sequence selected from a polynucleotide sequence encoding the SEQ ID NOS:6, 8, 10, 12, and 14. In some embodiments, the polynucleotide encoding an engineered TAL polypeptide has at least 80%, 85%, 90%, 93%, 95%, 96%, 97%, 98%, 99% nucleotide residue identity to SEQ ID NOS:5, 7, 9, 11, and/or 13.

In some embodiments, the polynucleotides are capable of hybridizing under highly stringent conditions to a reference polynucleotide sequence selected from SEQ ID NOS:5, 7, 9, 11, and/or 13, or a complement thereof, or a polynucleotide sequence encoding any of the variant TAL polypeptides provided herein. In some embodiments, the polynucleotide capable of hybridizing under highly stringent conditions encodes a TAL polypeptide comprising an amino acid sequence that has one or more residue differences as compared to SEQ ID NO:10, at residue positions selected from 73, 77, 88, 91, 93, 95, 97, 108, 222, 253, 304, 307, 315, 364, 389, 400, 401, 453, and/or 490.

In some embodiments, an isolated polynucleotide encoding any of the engineered TAL polypeptides provided herein is manipulated in a variety of ways to provide for expression of the polypeptide. In some embodiments, the polynucleotides encoding the polypeptides are provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

In some embodiments, the control sequences include among other sequences, promoters, leader sequences, polyadenylation sequences, propeptide sequences, signal peptide sequences, and transcription terminators. As known in the art, suitable promoters can be selected based on the host cells used. For bacterial host cells, suitable promoters for directing transcription of the nucleic acid constructs of the present application, include, but are not limited to the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice finds use in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is a suitable leader sequence, a non-translated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are also known in the art (See e.g., Guo and Sherman, Mol. Cell. Bio., 15:5983-5990 [1995]).

In some embodiments, the control sequence is a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region that directs the expressed polypeptide into the secretory pathway of a host cell of choice finds use for expression of the engineered TAL polypeptides provided herein. Effective signal peptide coding regions for bacterial host cells include, but are not limited to the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is a propeptide coding region that codes for an amino acid sequence positioned at the amino terminus of a polypeptide. The resultant polypeptide is referred to as a "proenzyme," "propolypeptide," or "zymogen," in some cases). A propolypeptide can be converted to a mature active polypeptide by catalytic or autocatalytic cleavage of the propeptide from the propolypeptide. The propeptide coding region includes, but is not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention also provides a recombinant expression vector comprising a polynucleotide encoding an engineered TAL polypeptide, and one or more expression regulating regions such as a promoter and a terminator, a replication origin, etc., depending on the type of hosts into which they are to be introduced. in some embodiments, the various nucleic acid and control sequences described above are joined together to produce a recombinant expression vector which includes one or more convenient restriction sites to allow for insertion or substitution of the nucleic acid sequence encoding the variant TAL polypeptide at such sites. Alternatively, the polynucleotide sequence(s) of the present invention are expressed by inserting the polynucleotide sequence or a nucleic acid construct comprising the polynucleotide sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), that can be conveniently subjected to recombinant DNA procedures and can result in the expression of the variant TAL polynucleotide sequence. The choice of the vector will typically depend on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the expression vector preferably contains one or more selectable markers, which permit easy selection of transformed cells. A "selectable marker" is a gene the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In another aspect, the present invention provides a host cell comprising a polynucleotide encoding at least one engineered TAL polypeptide of the present application, the polynucleotide being operatively linked to one or more control sequences for expression of the engineered TAL enzyme(s) in the host cell. Host cells for use in expressing the polypeptides encoded by the expression vectors of the present invention are well known in the art and include but are not limited to, bacterial cells, such as *E. coli*, *Vibrio fluvialis*, *Streptomyces* and *Salmonella typhimurium* cells; fungal cells, such as yeast cells (e.g., *Saccharomyces cerevisiae* and *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Exemplary host cells are *Escherichia coli* strains (such as W3110 (AfhuA) and BL21).

Accordingly, in another aspect, the present invention provides methods for producing the engineered TAL polypeptides, where the methods comprise culturing a host cell capable of expressing a polynucleotide encoding the engineered TAL polypeptide under conditions suitable for expression of the polypeptide. In some embodiments, the methods further comprise the steps of isolating and/or purifying the TAL polypeptides, as described herein.

Appropriate culture media and growth conditions for the above-described host cells are well known in the art. Polynucleotides for expression of the TAL polypeptides may be introduced into cells by various methods known in the art. Techniques include, among others, electroporation, biolistic particle bombardment, liposome mediated transfection, calcium chloride transfection, and protoplast fusion.

The engineered TAL with the properties disclosed herein can be obtained by subjecting the polynucleotide encoding the naturally occurring or engineered TAL polypeptide to mutagenesis and/or directed evolution methods known in the art, and as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254:157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; WO 2009/152336, and U.S. Pat. No. 6,537,746, all of which are incorporated herein by reference).

In some embodiments, the enzyme clones obtained following mutagenesis treatment are screened by subjecting the enzymes to a defined temperature (or other assay conditions) and measuring the amount of enzyme activity remaining after heat treatments or other assay conditions. Clones containing a polynucleotide encoding a TAL polypeptide are then isolated from the gene, sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tetra. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer), purified, annealed, ligated and cloned in appropriate vectors.

Accordingly, in some embodiments, a method for preparing the engineered TAL polypeptide can comprise: (a) synthesizing a polynucleotide encoding a polypeptide comprising an amino acid sequence selected from the amino acid sequence of any variant provided in Table 4-1, 4-2, 4-3, 4-4, 4-5, 4-6, and/or 4-7, as well as SEQ ID NOS:6, 8, 10, 12, and 14, and (b) expressing the TAL polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered TAL polypeptide can be measured for any desired improved property (e.g., activity, selectivity, stability, acid tolerance, protease sensitivity, etc.), using any suitable assay known in the art, including but not limited to the assays and conditions described herein.

In some embodiments, any of the engineered TAL polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the TAL polypeptides include, among others, reverse phase chromatography high performance liquid chromatography, ion exchange chromatography, hydrophobic interaction chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved variant TAL enzymes. In some embodiments utilizing affinity chromatography purification, any antibody which specifically binds the variant TAL polypeptide finds use. For the production of antibodies, various host animals, including but not limited to rabbits, mice, rats, etc., are immunized by injection with a TAL polypeptide (e.g., a TAL variant), or a fragment thereof. In some embodiments, the TAL polypeptide or fragment is attached to a suitable carrier, such as BSA, by means of a side chain functional group or linkers attached to a side chain functional group.

In some embodiments, the engineered TAL polypeptide is produced in a host cell by a method comprising culturing a host cell (e.g., an *E. coli* strain) comprising a polynucleotide sequence encoding an engineered TAL polypeptide as described herein under conditions conducive to the production of the engineered TAL polypeptide and recovering the engineered TAL polypeptide from the cells and/or culture medium.

In some preferred embodiments, the invention encompasses a method of producing an engineered TAL polypeptide comprising culturing a recombinant bacterial cell comprising a polynucleotide sequence encoding an engineered TAL polypeptide having at least 85%, 90%, 95%, 96%, 97%, 98%, 99%, or 100% sequence identity to reference sequences SEQ ID NOS:6, 8, 10, 12, and/or 14, and one or more amino acid residue differences as compared to SEQ ID NO:10, selected from amino acid positions 73, 77, 88, 91, 93, 95, 97, 108, 222, 253, 304, 307, 315, 364, 389, 400, 401, 453, and/or 490, and/or combinations thereof when optimally aligned with the amino acid sequence of SEQ ID NO:10, under suitable culture conditions to allow the production of the engineered TAL polypeptide and optionally recovering the engineered TAL polypeptide from the culture and/or cultured bacterial cells.

In some embodiments, once the engineered TAL polypeptides are recovered from the recombinant host cells or cell culture and they are further purified by any suitable method(s) known in the art. In some additional embodiments, the purified TAL polypeptides are combined with other ingredients and compounds to provide compositions and formulations comprising the engineered TAL polypeptide as appropriate for different applications and uses (e.g., pharmaceutical compositions).

Compositions:

Pharmaceutical Compositions

The present invention provides engineered TAL polypeptides suitable for use in pharmaceutical and other compositions, such as dietary/nutritional supplements.

Depending on the mode of administration, the compositions comprising a therapeutically effective amount of an engineered TAL according to the present invention are in the form of a solid, semi-solid, gel, or liquid. In some embodiments, the compositions include other pharmaceutically acceptable components such as diluents, buffers, excipients, salts, emulsifiers, preservatives, stabilizers, fillers, and other ingredients. Details on techniques for formulation and administration are well known in the art and described in the literature.

In some embodiments, the engineered TAL polypeptides are formulated for use in oral pharmaceutical compositions. Any suitable format for use in delivering the engineered TAL polypeptides find use in the present invention, including but not limited to pills, tablets, gel tabs, capsules, lozenges, dragees, powders, soft gels, sol-gels, gels, emulsions, implants, patches, sprays, ointments, liniments, creams, pastes, jellies, paints, aerosols, chewing gums, demulcents, sticks, suspensions (including but not limited to oil-based suspensions, oil-in water emulsions, etc.), slurries, syrups, controlled release formulations, suppositories, etc.

In some embodiments, the engineered TAL polypeptides are provided in a format suitable for injection (i.e., in an injectable formulation). In some embodiments, the engineered TAL polypeptides are provided in biocompatible matrices such as sol-gels, including silica-based (e.g., oxysilane) sol-gels. In some embodiments, the engineered TAL polypeptides are encapsulated. In some alternative embodiments, the engineered TAL polypeptides are encapsulated in nanostructures (e.g., nanotubes, nanotubules, nanocapsules, or microcapsules, microspheres, liposomes, etc.). Indeed, it is not intended that the present invention be limited to any particular delivery formulation and/or means of delivery. It is intended that the engineered TAL polypeptides be administered by any suitable means known in the art, including but not limited to parenteral, oral, topical, transdermal, intranasal, intraocular, intrathecal, via implants, etc.

In some embodiments, the engineered TAL polypeptides are chemically modified by glycosylation, pegylation (i.e., modified with polyethylene glycol [PEG] or activated PEG, etc.) or other compounds (See e.g., Ikeda, Amino Acids 29:283-287 [2005]; U.S. Pat. Nos. 7,531,341, 7,534,595, 7,560,263, and 7,53,653; US Pat. Appln. Publ. Nos. 2013/0039898, 2012/0177722, etc.). Indeed, it is not intended that the present invention be limited to any particular delivery method and/or mechanism.

In some additional embodiments, the engineered TAL polypeptides are provided in formulations comprising matrix-stabilized enzyme crystals. In some embodiments, the formulation comprises a cross-linked crystalline engineered TAL enzyme and a polymer with a reactive moiety that adheres to the enzyme crystals. The present invention also provides engineered TAL polypeptides in polymers.

In some embodiments, compositions comprising the engineered TAL polypeptides of the present invention include one or more commonly used carrier compounds, including but not limited to sugars (e.g., lactose, sucrose, mannitol, and/or sorbitol), starches (e.g., corn, wheat, rice, potato, or other plant starch), cellulose (e.g., methyl cellulose, hydroxypropylmethyl cellulose, sodium carboxy-methylcellulose), gums (e.g., arabic, tragacanth, guar, etc.), and/or proteins (e.g., gelatin, collagen, etc.). Additional components in oral formulations may include coloring and or sweetening agents (e.g., glucose, sucrose, and mannitol) and lubricating agents (e.g., magnesium stearate), as well as enteric coatings (e.g., methacrylate polymers, hydroxyl propyl methyl cellulose phthalate, and/or any other suitable enteric coating known in the art). In some embodiments, disintegrating or solubilizing agents are included (e.g., cross-linked polyvinyl pyrrolidone, agar, alginic acid or salts thereof, such as sodium alginate). In some embodiments, the engineered TAL polypeptide are be combined with various additional components, including but not limited to preservatives, suspending agents, thickening agents, wetting agents, alcohols, fatty acids, and/or emulsifiers, particularly in liquid formulations. In some embodiments, the engineered TAL polypeptides are administered to subjects in combination with other compounds used in the treatment of tyrosinemia and/or alkaptonuria, including but not limited to NTBC, nitisinone, antacids (e.g., omeprazole, esomeprazole and other prazoles), as well as any other suitable compounds.

In some embodiments, the present invention provides engineered TAL polypeptides suitable for use in decreasing the concentration of tyrosine in fluids such as blood, cerebrospinal fluid, etc. The dosages of engineered TAL polypeptide(s) administered to an animal depend upon the condition or disease, the general condition of the animal, and other factors known to those in the art. In some embodiments, the compositions are intended for single or multiple administrations to an animal. In some embodiments, it is contemplated that the concentration of engineered TAL polypeptide(s) in the composition(s) administered to an animal (e.g., a human with tyrosinemia or alkaptonuria) is sufficient to effectively treat, ameliorate and/or prevent the symptoms of disease (e.g., tyrosinemia or alkaptonuria and/or tyrosinemia or alkaptonuria-related conditions, diseases and/or symptoms), In some embodiments, the engineered TAL polypeptides are administered in combination with other pharmaceutical and/or dietary compositions.

Industrial Compositions

It is contemplated that the engineered TAL polypeptides of the present invention will find use in industrial compositions. In some embodiments, the engineered TAL polypeptides find use in the production of chemicals (e.g., coumaric acid). In some embodiments, the engineered TAL polypeptides are formulated for use in the food and/or feed industries. In some embodiments, the engineered TAL polypeptides are formulated in granulated or pelleted products which are mixed with animal feed components such as additional enzymes (for example, cellulases, laccases, and amylases). In some alternative embodiments, the engineered TAL polypeptides are used in liquid animal feed compositions (e.g., aqueous or oil based slurries). Thus, in some embodiments, the engineered TAL variants of the present invention are sufficiently thermotolerant and thermostable to withstand the treatment used to produce pellets and other processed feed/foods. In some further embodiments, the engineered TAL variants are used to produce tyrosine and/or tyrosine derivatives.

The engineered TAL polypeptides provided herein also find use in agricultural applications. Indeed, it is contemplated that modulation of TAL activity by using recombinant polypeptides having TAL activity will lead to effective herbicides.

The foregoing and other aspects of the invention may be better understood in connection with the following non-limiting examples. The examples are provided for illustrative purposes only and are not intended to limit the scope of the present invention in any way.

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); CDS (coding sequence); DNA (deoxyribonucleic acid); RNA (ribonucleic acid); E. coli W3110 (commonly used laboratory E. coli strain, available from the Coli Genetic Stock Center [CGSC], New Haven, Conn.); HPLC (high pressure liquid chromatography); SDS-PAGE (sodium dodecyl sulfate polyacrylamide gel electrophoresis); PES (polyethersulfone); CFSE (carboxyfluorescein succinimidyl ester); IPTG (isopropyl β-D-1-thiogalactopyranoside); PMBS (polymyxin B sulfate); NADPH (nicotinamide adenine dinucleotide phosphate); FIOPC (fold improvements over positive control); PHE and Phe (phenylalanine); TYR and Tyr (tyrosine); PBMC (peripheral blood mononuclear cells); LB (Luria broth); MeOH (methanol); Athens Research (Athens Research Technology, Athens, Ga.); ProSpec (ProSpec Tany Technogene, East Brunswick, N.J.); Sigma-Aldrich (Sigma-Aldrich, St. Louis, Mo.); Ram Scientific (Ram Scientific, Inc., Yonkers, N.Y.); Pall Corp. (Pall, Corp., Pt. Washington, NY); Millipore (Millipore, Corp., Billerica Mass.); Difco (Difco Laboratories, BD Diagnostic Systems, Detroit, Mich.); Molecular Devices (Molecular Devices, LLC, Sunnyvale, Calif.); Kuhner (Adolf Kuhner, AG, Basel, Switzerland); Cambridge Isotope Laboratories, (Cambridge Isotope Laboratories, Inc., Tewksbury. Mass.); Applied Biosystems (Applied Biosystems, part of Life Technologies, Corp., Grand Island, N.Y.), Agilent (Agilent Technologies, Inc., Santa Clara, Calif.); Thermo Scientific (part of Thermo Fisher Scientific, Waltham, Mass.); Corning (Corning, Inc., Palo Alto, Calif.); Megazyme (Megazyme International, Wicklow, Ireland); Enzo (Enzo Life Sciences, Inc., Farmingdale, N.Y.); GE Healthcare (GE Healthcare Bio-Sciences, Piscataway, N.J.); Pierce (Pierce Biotechnology (now part of Thermo Fisher Scientific), Rockford, Ill.); Phenomenex (Phenomenex, Inc., Torrance, Calif.); Optimal (Optimal Biotech Group, Belmont, Calif.); and Bio-Rad (Bio-Rad Laboratories, Hercules, Calif.).

The following polynucleotide and polypeptide sequences find use in the present invention. In some cases (as shown below), the polynucleotide sequence is followed by the encoded polypeptide.

```
Polynucleotide Sequence of pET16b-AvPAL Expression Vector (SEQ ID NO: 1):
                                                          (SEQ ID NO: 1)
TCTCATGTTTGACAGCTTATCATCGATAAGCTTTAATGCGGTAGTTTATCACAGTTAAATTGC

TAACGCAGTCAGGCACCGTGTATGAAATCTAACAATGCGCTCATCGTCATCCTCGGCACCGT

CACCCTGGATGCTGTAGGCATAGGCTTGGTTATGCCGGTACTGCCGGGCCTCTTGCGGGATA

TCCGGATATAGTTCCTCCTTTCAGCAAAAAACCCCTCAAGACCCGTTTAGAGGCCCCAAGGG

GTTATGCTAGTTATTGCTCAGCGGTGGCAGCAGCCAACTCAGCTTCCTTTCGGGCTTTGTTAG

CAGCCGGATCCTTAATGCAGACACGGCAGAATGTCCTGAACGGCCTGAACAATAACACCAC

CGGCTGCAATATCTGCACTAATACGTGCAATATGTTCATCCAGACCCTGTTCATTATCATTCC

AAATATACGGACGATCTGAGGTCGGTTTCTGACCAACAACATGACGAACTGCGCTATACAG

ACGTTCGGTTGCCGGTGACAGACAGGCACGTGCATCATAATGACCGGTTTTTTTGTAGGTAC
```

-continued

```
GCAGATCAACTGCCTGAACACCAAACATCAGGGCAATGGCAACATAATTCTGAAAAATATC

AACGCTACGACGTGCCAGGGTTGCGCTGGTATAACCCTGGCTGTTAATATTCTGGTTAAACT

GTTCGGCATGGGTCGGAAAACGATCTGCAATACTATTACCATAAAAGGTCAGCAGCGGCAT

AATGCTATTACCGCAAATCTGCAGACCTTTCAGACCCATATTAACTTTACGTTCACGATTACC

CAGCAGACTCGGAGGCAGACCATTGCTAAATTCCGGTGATGCCAGCAGTGCAATCTGAACA

TCCAGATGTTTTGCCAGCAGACCGATATAATAGCGCAGATGATCCATACCCATACCAACATA

CTGACCCAGAAAATTACCACCATGATAGCTTGCCTGATTATCAACATCAATCAGCGGGTTAT

CGGTAACGCTGTTAATCTCAATTTCGATTTGTTTGGCAATCTGGCTAATACCATCAACAATCG

GACCCAGATACTGCGGCAGACAACGCAGGCTATAACGATCCTGGATCAGTTCATGATCACG

ATAATCATGTTTACCATCCAGTTCATCACGAACCAGCTGGCTATTGGCCAGCAGGCTAATCA

TCTGATCTGCTGCCCACAGCTGACCCGGATGCGGTTTGCTGTTATGGATAAACGGATGAAAG

CTCTGATTTGTACCATTCAGTGCCTGAATATCCAGTGCATGAACACCCATTGCAATTGCGGTC

AGAATCTGGGTATCATAAACACAATTTGCTGCAATACCGGTCATAACGCTGGTGCCATTCAT

CATTGCCAGACCTTCTTTCGGCAGGGTCAGCGGACTCAGATTCAGCTGACGCAGTGCGG

TCGGTGCGTCCATTTCTTTGCCATTAAAATCAACTTTAAAGCTCGGGTCCAGGCCAATCAGG

CTACCGGTAATATAGCTCAGCGGAACCAGATCACCGCTGGCACCAATGCTACCAAATTCATA

AACATACGGGGTAACACCGGCATTCAGAAAGATTTCCATGCGTTTAATCAGTTCCAGACGAA

TACCGCTTGCACCACGCATGTGGCTATTTGCACGCAGCAGCATTGCTGCACGAACATCTGCC

AGCGGCAGTTTATTACCTGCACCGGTTTTCAGAAACCAAACCAGATTGGTCTGCAGTTCGCT

TGCCTGTTCACGGCTAATTGCAACATTTGCCATACCACCAAAACCGCTGGTAACACCATAAA

TCGGTTCACCGCTTTCAACTGCATTATTGATATAATCACAGCTGGCCTGAATACCCTGCAGA

ATATCGGTATTATTGGTCAGGCTAACCAGGGTGCCATTACGGGCAACACGTGCAACATCATT

GATGGTCAGTTTCTGATTACCAATAATCACATTTGCGCTGCTATTGCCGGTAAAGCTAAACT

GCTGGCTGCTGGTTTTGCTCTGTGCCTGGCTCAGGGTTTTCATATGACGACCTTCGATATGGC

CGCTGCTGTGATGATGATGATGATGATGATGATGATGGCCCATGGTATATCTCCTTCTTAAA

GTTAAACAAAATTATTTCTAGAGGGGAATTGTTATCCGCTCACAATTCCCCTATAGTGAGTC

GTATTAATTTCGCGGGATCGAGATCTCGATCCTCTACGCCGGACGCATCGTGGCCGGCATCA

CCGGCGCCACAGGTGCGGTTGCTGGCGCCTATATCGCCGACATCACCGATGGGGAAGATCG

GGCTCGCCACTTCGGGCTCATGAGCGCTTGTTTCGGCGTGGGTATGGTGGCAGGCCCCGTGG

CCGGGGGACTGTTGGGCGCCATCTCCTTGCATGCACCATTCCTTGCGGCGGCGGTGCTCAAC

GGCCTCAACCTACTACTGGGCTGCTTCCTAATGCAGGAGTCGCATAAGGGAGAGCGTCGAG

ATCCCGGACACCATCGAATGGCGCAAAACCTTTCGCGGTATGGCATGATAGCGCCCGGAAG

AGAGTCAATTCAGGGTGGTGAATGTGAAACCAGTAACGTTATACGATGTCGCAGAGTATGC

CGGTGTCTCTTATCAGACCGTTTCCCGCGTGGTGAACCAGGCCAGCCACGTTTCTGCGAAAA

CGCGGGAAAAGTGGAAGCGGCGATGGCGGAGCTGAATTACATTCCCAACCGCGTGGCACA

ACAACTGGCGGGCAAACAGTCGTTGCTGATTGGCGTTGCCACCTCCAGTCTGGCCCTGCACG

CGCCGTCGCAAATTGTCGCGGCGATTAAATCTCGCGCCGATCAACTGGGTGCCAGCGTGGTG

GTGTCGATGGTAGAACGAAGCGGCGTCGAAGCCTGTAAAGCGGCGGTGCACAATCTTCTCG

CGCAACGCGTCAGTGGGCTGATCATTAACTATCCGCTGGATGACCAGGATGCCATTGCTGTG

GAAGCTGCCTGCACTAATGTTCCGGCGTTATTTCTTGATGTCTCTGACCAGACACCCATCAAC

AGTATTATTTTCTCCCATGAAGACGGTACGCGACTGGGCGTGGAGCATCTGGTCGCATTGGG
```

-continued

```
TCACCAGCAAATCGCGCTGTTAGCGGGCCCATTAAGTTCTGTCTCGGCGCGTCTGCGTCTGG
CTGGCTGGCATAAATATCTCACTCGCAATCAAATTCAGCCGATAGCGGAACGGGAAGGCGA
CTGGAGTGCCATGTCCGGTTTTCAACAAACCATGCAAATGCTGAATGAGGGCATCGTTCCCA
CTGCGATGCTGGTTGCCAACGATCAGATGGCGCTGGGCGCAATGCGCGCCATTACCGAGTCC
GGGCTGCGCGTTGGTGCGGATATCTCGGTAGTGGGATACGACGATACCGAAGACAGCTCAT
GTTATATCCCGCCGTTAACCACCATCAAACAGGATTTTCGCCTGCTGGGGCAAACCAGCGTG
GACCGCTTGCTGCAACTCTCTCAGGGCCAGGCGGTGAAGGGCAATCAGCTGTTGCCCGTCTC
ACTGGTGAAAAGAAAAACCACCCTGGCGCCCAATACGCAAACCGCCTCTCCCCGCGCGTTG
GCCGATTCATTAATGCAGCTGGCACGACAGGTTTCCCGACTGGAAAGCGGGCAGTGAGCGC
AACGCAATTAATGTAAGTTAGCTCACTCATTAGGCACCGGGATCTCGACCGATGCCCTTGAG
AGCCTTCAACCCAGTCAGCTCCTTCCGGTGGGCGCGGGGCATGACTATCGTCGCCGCACTTA
TGACTGTCTTCTTTATCATGCAACTCGTAGGACAGGTGCCGGCAGCGCTCTGGGTCATTTTCG
GCGAGGACCGCTTTCGCTGGAGCGCGACGATGATCGGCCTGTCGCTTGCGGTATTCGGAATC
TTGCACGCCCTCGCTCAAGCCTTCGTCACTGGTCCCGCCACCAAACGTTTCGGCGAGAAGCA
GGCCATTATCGCCGGCATGGCGGCCGACGCGCTGGGCTACGTCTTGCTGGCGTTCGCGACGC
GAGGCTGGATGGCCTTCCCCATTATGATTCTTCTCGCTTCCGGCGGCATCGGGATGCCCGCGT
TGCAGGCCATGCTGTCCAGGCAGGTAGATGACGACCATCAGGGACAGCTTCAAGGATCGCT
CGCGGCTCTTACCAGCCTAACTTCGATCACTGGACCGCTGATCGTCACGGCGATTTATGCCG
CCTCGGCGAGCACATGGAACGGGTTGGCATGGATTGTAGGCGCCGCCCTATACCTTGTCTGC
CTCCCCGCGTTGCGTCGCGGTGCATGGAGCCGGGCCACCTCGACCTGAATGGAAGCCGGCG
GCACCTCGCTAACGGATTCACCACTCCAAGAATTGGAGCCAATCAATTCTTGCGGAGAACTG
TGAATGCGCAAACCAACCCTTGGCAGAACATATCCATCGCGTCCGCCATCTCCAGCAGCCGC
ACGCGGCGCATCTCGGGCAGCGTTGGGTCCTGGCCACGGGTGCGCATGATCGTGCTCCTGTC
GTTGAGGACCCGGCTAGGCTGGCGGGGTTGCCTTACTGGTTAGCAGAATGAATCACCGATAC
GCGAGCGAACGTGAAGCGACTGCTGCTGCAAAACGTCTGCGACCTGAGCAACAACATGAAT
GGTCTTCGGTTTCCGTGTTTCGTAAAGTCTGGAAACGCGGAAGTCAGCGCCCTGCACCATTA
TGTTCCGGATCTGCATCGCAGGATGCTGCTGGCTACCCTGTGGAACACCTACATCTGTATTA
ACGAAGCGCTGGCATTGACCCTGAGTGATTTTTCTCTGGTCCCGCCGCATCCATACCGCCAG
TTGTTTACCCTCACAACGTTCCAGTAACCGGGCATGTTCATCATCAGTAACCCGTATCGTGAG
CATCCTCTCTCGTTTCATCGGTATCATTACCCCCATGAACAGAAATCCCCCTTACACGGAGGC
ATCAGTGACCAAACAGGAAAAAACCGCCCTTAACATGGCCCGCTTTATCAGAAGCCAGACA
TTAACGCTTCTGGAGAAACTCAACGAGCTGGACGCGGATGAACAGGCAGACATCTGTGAAT
CGCTTCACGACCACGCTGATGAGCTTTACCGCAGCTGCCTCGCGCGTTTCGGTGATGACGGT
GAAAACCTCTGACACATGCAGCTCCCGGAGACGGTCACAGCTTGTCTGTAAGCGGATGCCG
GGAGCAGACAAGCCCGTCAGGGCGCGTCAGCGGGTGTTGGCGGGTGTCGGGGCGCAGCCAT
GACCCAGTCACGTAGCGATAGCGGAGTGTATACTGGCTTAACTATGCGGCATCAGAGCAGA
TTGTACTGAGAGTGCACCATATATGCGGTGTGAAATACCGCACAGATGCGTAAGGAGAAAA
TACCGCATCAGGCGCTCTTCCGCTTCCTCGCTCACTGACTCGCTGCGCTCGGTCGTTCGGCTG
CGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCG
```

-continued

```
CGTTGCTGGCGTTTTTCCATAGGCTCCGCCCCCTGACGAGCATCACAAAAATCGACGCTCA

AGTCAGAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAGGTCGTTC

GCTCCAAGCTGGGCTGTGTGCACGAACCCCCCGTTCAGCCCGACCGCTGCGCCTTATCCGGT

AACTATCGTCTTGAGTCCAACCCGGTAAGACACGACTTATCGCCACTGGCAGCAGCCACTGG

TAACAGGATTAGCAGAGCGAGGTATGTAGGCGGTGCTACAGAGTTCTTGAAGTGGTGGCCT

AACTACGGCTACACTAGAAGGACAGTATTTGGTATCTGCGCTCTGCTGAAGCCAGTTACCTT

CGGAAAAAGAGTTGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGATCCTTTGATCTTT

TCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCA

GCGATCTGTCTATTTCGTTCATCCATAGTTGCCTGACTCCCCGTCGTGTAGATAACTACGATA

CGGGAGGGCTTACCATCTGGCCCCAGTGCTGCAATGATACCGCGAGACCCACGCTCACCGGC

TCCAGATTTATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGTAGTTCGCCA

GTTAATAGTTTGCGCAACGTTGTTGCCATTGCTGCAGGCATCGTGGTGTCACGCTCGTCGTTT

GGTATGGCTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCGCAG

TGTTATCACTCATGGTTATGGCAGCACTGCATAATTCTCTTACTGTCATGCCATCCGTAAGAT

GCTTTTCTGTGACTGGTGAGTACTCAACCAAGTCATTCTGAGAATAGTGTATGCGGCGACCG

AGTTGCTCTTGCCCGGCGTCAACACGGGATAATACCGCGCCACATAGCAGAACTTTAAAAGT

GCTCATCATTGGAAAACGTTCTTCGGGGCGAAAACTCTCAAGGATCTTACCGCTGTTGAGAT

CCAGTTCGATGTAACCCACTCGTGCACCCAACTGATCTTCAGCATCTTTTACTTTCACCAGCG

TTTCTGGGTGAGCAAAAACAGGAAGGCAAAATGCCGCAAAAAAGGGAATAAGGGCGACAC

GGAAATGTTGAATACTCATACTCTTCCTTTTTCAATATTATTGAAGCATTTATCAGGGTTATT

GTCTCATGAGCGGATACATATTTGAATGTATTTAGAAAAATAAACAAATAGGGGTTCCGCGC

ACATTTCCCCGAAAAGTGCCACCTGACGTCTAAGAAACCATTATTATCATGACATTAACCTA

TAAAAATAGGCGTATCACGAGGCCCTTTCGTCTTCAAGAAT
```

AvPAL ORF Polynucleotide Sequence (SEQ ID NO: 2):

(SEQ ID NO: 2)

```
ATGAAACCCTGAGCCAGGCACAGAGCAAAACCAGCAGCCAGCAGTTTAGCTTTACCGGCA

ATAGCAGCGCAAATGTGATTATTGGTAATCAGAAACTGACCATCAATGATGTTGCACGTGTT

GCCCGTAATGGCACCCTGGTTAGCCTGACCAATAATACCGATATTCTGCAGGGTATTCAGGC

CAGCTGTGATTATATCAATAATGCAGTTGAAAGCGGTGAACCGATTTATGGTGTTACCAGCG

GTTTTGGTGGTATGGCAAATGTTGCAATTAGCCGTGAACAGGCAAGCGAACTGCAGACCAAT

CTGGTTTGGTTTCTGAAAACCGGTGCAGGTAATAAACTGCCGCTGGCAGATGTTCGTGCAGC

AATGCTGCTGCGTGCAAATAGCCACATGCGTGGTGCAAGCGGTATTCGTCTGGAACTGATTA

AACGCATGGAAATCTTTCTGAATGCCGGTGTTACCCCGTATGTTTATGAATTTGGTAGCATTG

GTGCCAGCGGTGATCTGGTTCCGCTGAGCTATATTACCGGTAGCCTGATTGGCCTGGACCCG

AGCTTTAAAGTTGATTTTAATGGCAAAGAAATGGACGCACCGACCGCACTGCGTCAGCTGAA
```

```
TCTGAGTCCGCTGACCCTGCTGCCGAAAGAAGGTCTGGCAATGATGAATGGCACCAGCGTTA
TGACCGGTATTGCAGCAAATTGTGTTTATGATACCCAGATTCTGACCGCAATTGCAATGGGT
GTTCATGCACTGGATATTCAGGCACTGAATGGTACAAATCAGAGCTTTCATCCGTTTATCCAT
AACAGCAAACCGCATCCGGGTCAGCTGTGGGCAGCAGATCAGATGATTAGCCTGCTGGCCA
ATAGCCAGCTGGTTCGTGATGAACTGGATGGTAAACATGATTATCGTGATCATGAACTGATC
CAGGATCGTTATAGCCTGCGTTGTCTGCCGCAGTATCTGGGTCCGATTGTTGATGGTATTAGC
CAGATTGCCAAACAAATCGAAATTGAGATTAACAGCGTTACCGATAACCCGCTGATTGATGT
TGATAATCAGGCAAGCTATCATGGTGGTAATTTTCTGGGTCAGTATGTTGGTATGGGTATGG
ATCATCTGCGCTATTATATCGGTCTGCTGGCAAAACATCTGGATGTTCAGATTGCACTGCTGG
CATCACCGGAATTTAGCAATGGTCTGCCTCCGAGTCTGCTGGGTAATCGTGAACGTAAAGTT
AATATGGGTCTGAAAGGTCTGCAGATTTGCGGTAATAGCATTATGCCGCTGCTGACCTTTTA
TGGTAATAGTATTGCAGATCGTTTTCCGACCCATGCCGAACAGTTTAACCAGAATATTAACA
GCCAGGGTTATACCAGCGCAACCCTGGCACGTCGTAGCGTTGATATTTTTCAGAATTATGTT
GCCATTGCCCTGATGTTTGGTGTTCAGGCAGTTGATCTGCGTACCTACAAAAAAACCGGTCA
TTATGATGCACGTGCCTGTCTGTCACCGGCAACCGAACGTCTGTATAGCGCAGTTCGTCATG
TTGTTGGTCAGAAACCGACCTCAGATCGTCCGTATATTTGGAATGATAATGAACAGGGTCTG
GATGAACATATTGCACGTATTAGTGCAGATATTGCAGCCGGTGGTGTTATTGTTCAGGCCGT
TCAGGACATTCTGCCGTGTCTGCAT
```

AvPAL WT Polynucleotide Sequence (SEQ ID NO: 3):

(SEQ ID NO: 3)
```
ATGAAAACCCTGAGCCAGGCACAGAGCAAAACCAGCAGCCAGCAGTTTAGCTTTACCGGCA
ATAGCAGCGCAAATGTGATTATTGGTAATCAGAAACTGACCATCAATGATGTTGCACGTGTT
GCCCGTAATGGCACCCTGGTTAGCCTGACCAATAATACCGATATTCTGCAGGGTATTCAGGC
CAGCTGTGATTATATCAATAATGCAGTTGAAAGCGGTGAACCGATTTATGGTGTTACCAGCG
GTTTTGGTGGTATGGCAAATGTTGCAATTAGCCGTGAACAGGCAAGCGAACTGCAGACCAAT
CTGGTTTGGTTTCTGAAAACCGGTGCAGGTAATAAACTGCCGCTGGCAGATGTTCGTGCAGC
AATGCTGCTGCGTGCAAATAGCCACATGCGTGGTGCAAGCGGTATTCGTCTGGAACTGATTA
AACGCATGGAAATCTTTCTGAATGCCGGTGTTACCCCGTATGTTTATGAATTTGGTAGCATTG
GTGCCAGCGGTGATCTGGTTCCGCTGAGCTATATTACCGGTAGCCTGATTGGCCTGGACCCG
AGCTTTAAAGTTGATTTTAATGGCAAAGAAATGGACGCACCGACCGCACTGCGTCAGCTGAA
TCTGAGTCCGCTGACCCTGCTGCCGAAAGAAGGTCTGGCAATGATGAATGGCACCAGCGTTA
TGACCGGTATTGCAGCAAATTGTGTTTATGATACCCAGATTCTGACCGCAATTGCAATGGGT
GTTCATGCACTGGATATTCAGGCACTGAATGGTACAAATCAGAGCTTTCATCCGTTTATCCAT
AACAGCAAACCGCATCCGGGTCAGCTGTGGGCAGCAGATCAGATGATTAGCCTGCTGGCCA
ATAGCCAGCTGGTTCGTGATGAACTGGATGGTAAACATGATTATCGTGATCATGAACTGATC
CAGGATCGTTATAGCCTGCGTTGTCTGCCGCAGTATCTGGGTCCGATTGTTGATGGTATTAGC
CAGATTGCCAAACAAATCGAAATTGAGATTAACAGCGTTACCGATAACCCGCTGATTGATGT
TGATAATCAGGCAAGCTATCATGGTGGTAATTTTCTGGGTCAGTATGTTGGTATGGGTATGG
ATCATCTGCGCTATTATATCGGTCTGCTGGCAAAACATCTGGATGTTCAGATTGCACTGCTGG
CATCACCGGAATTTAGCAATGGTCTGCCTCCGAGTCTGCTGGGTAATCGTGAACGTAAAGTT
AATATGGGTCTGAAAGGTCTGCAGATTTGCGGTAATAGCATTATGCCGCTGCTGACCTTTTA
```

-continued

```
TGGTAATAGTATTGCAGATCGTTTTCCGACCCATGCCGAACAGTTTAACCAGAATATTAACA

GCCAGGGTTATACCAGCGCAACCCTGGCACGTCGTAGCGTTGATATTTTTCAGAATTATGTT

GCCATTGCCCTGATGTTTGGTGTTCAGGCAGTTGATCTGCGTACCTACAAAAAAACCGGTCA

TTATGATGCACGTGCCTGTCTGTCACCGGCAACCGAACGTCTGTATAGCGCAGTTCGTCATG

TTGTTGGTCAGAAACCGACCTCAGATCGTCCGTATATTTGGAATGATAATGAACAGGGTCTG

GATGAACATATTGCACGTATTAGTGCAGATATTGCAGCCGGTGGTGTTATTGTTCAGGCCGT

TCAGGACATTCTGCCGTGTCTGCAT
```

AvPAL WT Polypeptide Sequence (SEQ ID NO: 4):

(SEQ ID NO: 4)
```
MKTLSQAQSKTSSQQFSFTGNSSANVIIGNQKLTINDVARVARNGTLVSLTNNTDILQGIQASCD

YINNAVESGEPIYGVTSGFGGMANVAISREQASELQTNLVWFLKTGAGNKLPLADVRAAMLLR

ANSHMRGASGIRLELIKRMEIFLNAGVTPYVYEFGSIGASGDLVPLSYITGSLIGLDPSFKVDFNG

KEMDAPTALRQLNLSPLTLLPKEGLAMMNGTSVMTGIAANCVYDTQILTAIAMGVHALDIQAL

NGTNQSFHPFIHNSKPHPGQLWAADQMISLLANSQLVRDELDGKHDYRDHELIQDRYSLRCLPQ

YLGPIVDGISQIAKQIEIEINSVTDNPLIDVDNQASYHGGNFLGQYVGMGMDHLRYYIGLLAKHL

DVQIALLASPEFSNGLPPSLLGNRERKVNMGLKGLQICGNSIMPLLTFYGNSIADRFPTHAEQFNQ

NINSQGYTSATLARRSVDIFQNYVAIALMFGVQAVDLRTYKKTGHYDARACLSPATERLYSAVR

HVVGQKPTSDRPYIWNDNEQGLDEHIARISADIAAGGVIVQAVQDILPCLH
```

AvPAL Variant No. 1 Polynucleotide Sequence (SEQ ID NO: 5):

(SEQ ID NO: 5)
```
ATGAAAACCCTGAGTCAGGCACAGAGCAAAACCAGCAGCCAGCAGTTTAGCTTTACCGGCA

ATAGCAGCGCAAATGTGATTATTGGTAATCAGAAACTGACCATCAATGATGTTGTACGTGTT

GCCCGTAATGGCACCCTGGTTAGCCTGACCAATAATACCGATATTCTGCAGGGTATTCAGGC

CAGCTGTGATTATATCAATAATGCAGTTGAAAGCGGTGAACCGATTTATGGTGTTACCAGCG

GTTTTGGTGGTATGGCAAATGTTGTAATTAGCCGTGAACAGGCAAGCGAACTGCAGACCAAT

CTGGTTTGGTTTCTGAAAACCGGTGCAGGTAATAAACTGCCGCTGGCAGATGTTCGTGCAGC

AATGCTGCTGCGTGCAAATAGCCACATGCGTGGTGCAAGCGGTATTCGTCTGGAACTGATTA

AACGCATGGAAATCTTTCTGAATGCCGGTGTTACCCCGTATGTTTATGAATTTGGTAGCATTG

GTGCCAGCGGTGATCTGGTTCCGCTGAGCTATATTACCGGTAGCCTGATTGGCCTGGACCCG

AGCTTTAAAGTTGATTTTAATGGCAAAGAAATGGACGCACCGACCGCACTGCGTCAGCTGAA

TCTGAGTCCGCTGACCCTGCTGCCGAAAGAAGGTCTGGCAATGATGAATGGCACCAGCGTTA

TGACCGGTATTGCAGCAAATTGTGTTTATGATACCCAGATTCTGACCGCAATTGCAATGGGT

GTTCATGCACTGGATATTCAGGCACTGAATGGTACAAATCAGAGCTTTCATCCGTTTATCCAT

AACAGCAAACCGCATCCGGGTCAGCTGTGGGCAGCAGATCAGATGATTAGCCTGCTGGCCG

GTAGCCAGCTGGTTCGTGATGAACTGGATGGTAAACATGATTATCGTGATGGTGAACTGATC

CAGGATCGTTATAGCCTGCGTTGTCTGCCGCAGTATCTGGGTCCGATTGTTGATGGTATTAGC

CAGATTGCCAAACAAATCGAAATTGAGATTAACAGCGTTACCGATAACCCGCTGATTGATGT

TGATAATCAGGCAAGCTATCATGGTGGTAATTTTCTGGGTCAGTATGTTGGTATGGGTATGG

ATCATCTGCGCTATTATATCGGTCTGCTGGCAAAACATCTGGATGTTCAGATTGCACTGCTGG

CATCACCGGAATTTAGCAATGGTCTGCCTCCGAGTCTGGTGGGTAATCGTGAACGTAAAGTT

AATATGGGTCTGAAAGGTCTGCAGATTTGCGGTAATAGCATTATGCCGCTGCTGACCTTTTA

TGGTAATAGTATTGCAGATCGTTTTCCGACCCATGCCGAACAGTTTAACCAGAATATTAACA

GCCAGGGTTATACCAGCGCAACCCTGGCACGTCGTAGCGTTGATATTTTTCAGAATTATGTT
```

-continued

```
GCCATTGCCCTGATGTTTGGTGTTCAGGCAGTTGATCTGCGTACCTACAAAAAAACCGGTCA

TTATGATGCACGTGCCTGTCTGTCACCGGCAACCGAACGTCTGTATAGCGCAGTTCGTCATG

TTGTTGGTCAGAAACCGAGCTCAGATCGTCCGTATATTTGGAATGATAATGAACAGGGTCTG

GATGAACATATTGCACGTATTAGTGCAGATATTGCAGCCGGTGGTGTTATTGTTCAGGCCGT

TCAGGACATTCTGCCGTGTCTGCAT
```

AvPAL Variant No. 1 Polypeptide Sequence (SEQ ID NO: 6):

(SEQ ID NO: 6)

```
MKTLSQAQSKTSSQQFSFTGNSSANVIIGNQKLTINDVVRVARNGTLVSLTNNTDILQGIQASCD

YINNAVESGEPIYGVTSGFGGMANVVISREQASELQTNLVWFLKTGAGNKLPLADVRAAMLLR

ANSHMRGASGIRLELIKRMEIFLNAGVTPYVYEFGSIGASGDLVPLSYITGSLIGLDPSFKVDFNG

KEMDAPTALRQLNLSPLTLLPKEGLAMMNGTSVMTGIAANCVYDTQILTAIAMGVHALDIQAL

NGTNQSFHPFIHNSKPHPGQLWAADQMISLLAGSQLVRDELDGKHDYRDGELIQDRYSLRCLPQ

YLGPIVDGISQIAKQIEIEINSVTDNPLIDVDNQASYHGGNFLGQYVGMGMDHLRYYIGLLAKHL

DVQIALLASPEFSNGLPPSLVGNRERKVNMGLKGLQICGNSIMPLLTFYGNSIADRFPTHAEQFNQ

NINSQGYTSATLARRSVDIFQNYVAIALMFGVQAVDLRTYKKTGHYDARACLSPATERLYSAVR

HVVGQKPSSDRPYIWNDNEQGLDEHIARISADIAAGGVIVQAVQDILPCLH
```

AvPAL Variant No. 2 Polynucleotide Sequence (SEQ ID NO: 7):

(SEQ ID NO: 7)

```
ATGAAAACCCTGAGCCAGGCACAGAGCAAAACCAGCAGCCAGCAGTTTAGCTTTACCGGCA

ATAGCAGCGCAAATGTGATTATTGGTAATCAGAAACTGACCATCAATGATGTTGCACGTGTT

GCCCGTAATGGCACCCTGGTTAGCCTGACCAATAATACCGATATTCTGCAGGGTATTCAGGC

CAGCTGTGATTATATCAATAATGCAGTTGAAAGCGGTGAACCGATTTATGGTGTTACCAGCG

GTTTTGGTGGTATGGCAAATGTTGCAATTAGCCGTGAACAGGCAAGCGAACTGCAGACCAAT

CTGGTTTGGCACCTGAAAACCGGTGCAGGTAATAAACTGCCGCTGGCAGATGTTCGTGCAGC

AATGCTGCTGCGTGCAAATAGCCACATGCGTGGTGCAAGCGGTATTCGTCTGGAACTGATTA

AACGCATGGAAATCTTTCTGAATGCCGGTGTTACCCCGTATGTTTATGAATTTGGTAGCATTG

GTGCCAGCGGTGATCTGGTTCCGCTGAGCTATATTACCGGTAGCCTGATTGGCCTGGACCCG

AGCTTTAAAGTTGATTTTAATGGCAAAGAAATGGACGCACCGACCGCACTGCGTCAGCTGAA

TCTGAGTCCGCTGACCCTGCTGCCGAAAGAAGGTCTGGCAATGATGAATGGCACCAGCGTTA

TGACCGGTATTGCAGCAAATTGTGTTTATGATACCCAGATTCTGACCGCAATTGCAATGGGT

GTTCATGCACTGGATATTCAGGCACTGAATGGTACAAATCAGAGCTTTCATCCGTTTATCCAT

AACAGCAAACCGCATCCGGGTCAGCTGTGGGCAGCAGATCAGATGATTAGCCTGCTGGCCA

ATAGCCAGCTGGTTCGTGATGAACTGGATGGTAAACATGATTATCGTGATCATGAACTGATC

CAGGATCGTTATAGCCTGCGTTGTCTGCCGCAGTATCTGGGTCCGATTGTTGATGGTATTAGC

CAGATTGCCAAACAAATCGAAATTGAGATTAACAGCGTTACCGATAACCCGCTGATTGATGT

TGATAATCAGGCAAGCTATCATGGTGGTAATTTTCTGGGTCAGTATGTTGGTATGGGTATGG

ATCATCTGCGCTATTATATCGGTCTGCTGGCAAAACATCTGGATGTTCAGATTGCACTGCTGG

CATCACCGGAATTTAGCAATGGTCTGCCTCCGAGTCTGCTGGGTAATCGTGAACGTAAAGTT

AATATGGGTCTGAAAGGTCTGCAGATTTGCGGTAATAGCATTATGCCGCTGCTGACCTTTTA

TGGTAATAGTATTGCAGATCGTTTTCCGACCCATGCCGAACAGTTTAACCAGAATATTAACA

GCCAGGGTTATACCAGCGCAACCCTGGCACGTCGTAGCGTTGATATTTTTCAGAATTATGTT

GCCATTGCCCTGATGTTTGGTGTTCAGGCAGTTGATCTGCGTACCTACAAAAAAACCGGTCA
```

```
TTATGATGCACGTGCCTGTCTGTCACCGGCAACCGAACGTCTGTATAGCGCAGTTCGTCATG

TTGTTGGTCAGAAACCGACCTCAGATCGTCCGTATATTTGGAATGATAATGAACAGGGTCTG

GATGAACATATTGCACGTATTAGTGCAGATATTGCAGCCGGTGGTGTTATTGTTCAGGCCGT

TCAGGACATTCTGCCGTGTCTGCAT
```

AvPAL Variant No. 2 Polypeptide Sequence (SEQ ID NO: 8):

(SEQ ID NO: 8)

```
MKTLSQAQSKTSSQQFSFTGNSSANVIIGNQKLTINDVARVARNGTLVSLTNNTDILQGIQASCD

YINNAVESGEPIYGVTSGFGGMANVAISREQASELQTNLVWHLKTGAGNKLPLADVRAAMLLR

ANSHMRGASGIRLELIKRMEIFLNAGVTPYVYEFGSIGASGDLVPLSYITGSLIGLDPSFKVDFNG

KEMDAPTALRQLNLSPLTLLPKEGLAMMNGTSVMTGIAANCVYDTQILTAIAMGVHALDIQAL

NGTNQSFHPFIHNSKPHPGQLWAADQMISLLANSQLVRDELDGKHDYRDHELIQDRYSLRCLPQ

YLGPIVDGISQIAKQIEIEINSVTDNPLIDVDNQASYHGGNFLGQYVGMGMDHLRYYIGLLAKHL

DVQIALLASPEFSNGLPPSLLGNRERKVNMGLKGLQICGNSIMPLLTFYGNSIADRFPTHAEQFNQ

NINSQGYTSATLARRSVDIFQNYVAIALMFGVQAVDLRTYKKTGHYDARACLSPATERLYSAVR

HVVGQKPTSDRPYIWNDNEQGLDEHIARISADIAAGGVIVQAVQDILPCLH
```

AvPAL Variant No. 3 Polynucleotide Sequence (SEQ ID NO: 9):

(SEQ ID NO: 9)

```
ATGAAAACCCTGAGTCAGGCACAGAGCAAAACCAGCAGCCAGCAGTTTAGCTTTACCGGCA

ATAGCAGCGCAAATGTGATTATTGGTAATCAGAAACTGACCATCAATGATGTTGTACGTGTT

GCCCGTAATGGCACCCTGGTTAGCCTGACCAATAATACCGATATTCTGCAGGGTATTCAGGC

CAGCTGTGATTATATCAATAATGCAGTTGAAAGCGGTGAACCGATTTATGGTGTTACCAGCG

GTTTTGGTGGTATGGCAAATGTTGTAATTAGCCGTGAACAGGCAAGCGAACTGCAGACCAAT

CTGGTTTGGCACCTGAAAACCGGTGCAGGTAATAAACTGCCGCTGGCAGATGTTCGTGCAGC

AATGCTGCTGCGTGCAAATAGCCACATGCGTGGTGCAAGCGGTATTCGTCTGGAACTGATTA

AACGCATGGAAATCTTTCTGAATGCCGGTGTTACCCCGTATGTTTATGAATTTGGTAGCATTG

GTGCCAGCGGTGATCTGGTTCCGCTGAGCTATATTACCGGTAGCCTGATTGGCCTGGACCCG

AGCTTTAAAGTTGATTTTAATGGCAAAGAAATGGACGCACCGACCGCACTGCGTCAGCTGAA

TCTGAGTCCGCTGACCCTGCTGCCGAAAGAAGGTCTGGCAATGATGAATGGCACCAGCGTTA

TGACCGGTATTGCAGCAAATTGTGTTTATGATACCCAGATTCTGACCGCAATTGCAATGGGT

GTTCATGCACTGGATATTCAGGCACTGAATGGTACAAATCAGAGCTTTCATCCGTTTATCCAT

AACAGCAAACCGCATCCGGGTCAGCTGTGGGCAGCAGATCAGATGATTAGCCTGCTGGCCG

GTAGCCAGCTGGTTCGTGATGAACTGGATGGTAAACATGATTATCGTGATGGTGAACTGATC

CAGGATCGTTATAGCCTGCGTTGTCTGCCGCAGTATCTGGGTCCGATTGTTGATGGTATTAGC

CAGATTGCCAAACAAATCGAAATTGAGATTAACAGCGTTACCGATAACCCGCTGATTGATGT

TGATAATCAGGCAAGCTATCATGGTGGTAATTTTCTGGGTCAGTATGTTGGTATGGGTATGG

ATCATCTGCGCTATTATATCGGTCTGCTGGCAAAACATCTGGATGTTCAGATTGCACTGCTGG

CATCACCGGAATTTAGCAATGGTCTGCCTCCGAGTCTGGTGGGTAATCGTGAACGTAAAGTT

AATATGGGTCTGAAAGGTCTGCAGATTTGCGGTAATAGCATTATGCCGCTGCTGACCTTTTA

TGGTAATAGTATTGCAGATCGTTTTCCGACCCATGCCGAACAGTTTAACCAGAATATTAACA

GCCAGGGTTATACCAGCGCAACCCTGGCACGTCGTAGCGTTGATATTTTTCAGAATTATGTT

GCCATTGCCCTGATGTTTGGTGTTCAGGCAGTTGATCTGCGTACCTACAAAAAAACCGGTCA

TTATGATGCACGTGCCTGTCTGTCACCGGCAACCGAACGTCTGTATAGCGCAGTTCGTCATG

TTGTTGGTCAGAAACCGAGCTCAGATCGTCCGTATATTTGGAATGATAATGAACAGGGTCTG
```

```
GATGAACATATTGCACGTATTAGTGCAGATATTGCAGCCGGTGGTGTTATTGTTCAGGCCGT

TCAGGACATTCTGCCGTGTCTGCAT
```

AvPAL Variant No. 3 Polypeptide Sequence (SEQ ID NO: 10):

(SEQ ID NO: 10)
```
MKTLSQAQSKTSSQQFSFTGNSSANVIIGNQKLTINDVVRVARNGTLVSLTNNTDILQGIQASCD

YINNAVESGEPIYGVTSGFGGMANVVISREQASELQTNLVWHLKTGAGNKLPLADVRAAMLLR

ANSHMRGASGIRLELIKRMEIFLNAGVTPYVYEFGSIGASGDLVPLSYITGSLIGLDPSFKVDFNG

KEMDAPTALRQLNLSPLTLLPKEGLAMMNGTSVMTGIAANCVYDTQILTAIAMGVHALDIQAL

NGTNQSFHPFIHNSKPHPGQLWAADQMISLLAGSQLVRDELDGKHDYRDGELIQDRYSLRCLPQ

YLGPIVDGISQIAKQIEIEINSVTDNPLIDVDNQASYHGGNFLGQYVGMGMDHLRYYIGLLAKHL

DVQIALLASPEFSNGLPPSLVGNRERKVNMGLKGLQICGNSIMPLLTFYGNSIADRFPTHAEQFNQ

NINSQGYTSATLARRSVDIFQNYVAIALMFGVQAVDLRTYKKTGHYDARACLSPATERLYSAVR

HVVGQKPSSDRPYIWNDNEQGLDEHIARISADIAAGGVIVQAVQDILPCLH
```

AvPAL Variant No. 17 Polynucleotide Sequence (SEQ ID NO: 11):

(SEQ ID NO: 11)
```
ATGAAAACCCTGAGTCAGGCACAGAGCAAAACCAGCAGCCAGCAGTTTAGCTTTACCGGCA

ATAGCAGCGCAAATGTGATTATTGGTAATCAGAAACTGACCATCAATGATGTTGTACGTGTT

GCCCGTAATGGCACCCTGGTTAGCCTGACCAATAATACCGATATTCTGCAGGGTATTCAGGC

CAGCTGTGATTATATCAATAATGCAGTTGAAAGCGGTGAACCGATGTATGGTGTTACCAGCG

GTTTTGGTGGTATGGCAAATGTTGTAATTAGCCGTGAACAGGCAAGCGAACTGCAGACCAAT

CTGGTTTGGCACCTGAAAACCGGTGCAGGTAATAAACTGCCGCTGGCAGATGTTCGTGCAGC

AATGCTGCTGCGTCAAATAGCCACATGCGTGGTGCAAGCGGTATTCGTCTGGAACTGATTA

AACGCATGGAAATCTTTCTGAATGCCGGTGTTACCCCGTATGTTTATGAATTTGGTAGCATTG

GTGCCAGCGGTGATCTGGTTCCGCTGAGCTATATTACCGGTAGCCTGATTGGCCTGGACCCG

AGCTTTAAAGTTGATTTTAATGGCAAAGAAATGGACGCACCGACCGCACTGCGTCAGCTGAA

TCTGAGTCCGCTGACCCTGCTGCCGAAAGAAGGTCTGGCAATGATGAATGGCACCAGCGTTA

TGACCGGTATTGCAGCAAATTGTGTTTATGATACCCAGATTCTGACCGCAATTGCAATGGGT

GTTCATGCACTGGATATTCAGGCACTGAATGGTACAAATCAGAGCTTTCATCCGTTTATCCAT

AACAGCAAACCGCATCCGGGTCAGCTGTGGGCAGCAGATCAGATGATTAGCCTGCTGGCCG

GTAGCCAGCTGGTTCGTGATGAACTGGATGGTAAACATGATTATCGTGATGGTGAACTGATC

CAGGATCGTTATAGCCTGCGTTGTCTGCCGCAGTATCTGGGTCCGATTGTTGATGGTATTAGC

CAGATTGCCAAACAAATCGAAATTGAGATTAACAGCGTTACCGATAACCCGCTGATTGATGT

TGATAATCAGGCAAGCTATCATGGTGGTAATTTTCTGGGTCAGTATGTTGGTATGGGTATGG

ATCATCTGCGCTATTATATCGGTCTGCTGGCAAAACATCTGGATGTTCAGATTGCACTGCTGG

CATCACCGGAATTTAGCAATGGTCTGCCTCCGAGTCTGGTGGGTAATCGTGAACGTAAAGTT

AATATGGGTCTGAAAGGTCTGCAGATTTGCGGTAATAGCATTATGCCGCTGCTGACCTTTTA

TGGTAATAGTATTGCAGATCGTTTTCCGACCCATGCCGAACAGTTTAACCAGAATATTAACA

GCCAGGGTTATACCAGCGCAACCCTGGCACGTCGTAGCGTTGATATTTTTCAGAATTATGTT

GCCATTGCCCTGATGTTTGGTGTTCAGGCAGTTGATCTGCGTACCTACAAAAAAACCGGTCA

TTATGATGCACGTGCCTGTCTGTCACCGGCAACCGAACGTCTGTATAGCGCAGTTCGTCATG

TTGTTGGTCAGAAACCGAGCTCAGATCGTCCGTATATTTGGAATGATAATGAACAGGGTCTG

GATGAACATATTGCACGTATTAGTGCAGATATTGCAGCCGGTGGTGTTATTGTTCAGGCCGT
```

TCAGGACATTCTGCCGTGTCTGCAT

AvPAL Variant No. 17 Polypeptide Sequence (SEQ ID NO: 12):

(SEQ ID NO: 12)
MKTLSQAQSKTSSQQFSFTGNSSANVIIGNQKLTINDVVRVARNGTLVSLTNNTDILQGI

QASCDYINNAVESGEPMYGVTSGFGGMANVVISREQASELQTNLVWHLKTGAGNKLPLADVRA

AMLLRANSHMRGASGIRLELIKRMEIFLNAGVTPYVYEFGSIGASGDLVPLSYITGSLIGLDPSFK

VDFNGKEMDAPTALRQLNLSPLTLLPKEGLAMMNGTSVMTGIAANCVYDTQILTAIAMGVHAL

DIQALNGTNQSFHPFIHNSKPHPGQLWAADQMISLLAGSQLVRDELDGKHDYRDGELIQDRYSL

RCLPQYLGPIVDGISQIAKQIEIEINSVTDNPLIDVDNQASYHGGNFLGQYVGMGMDHLRYYIGLL

AKHLDVQIALLASPEFSNGLPPSLVGNRERKVNMGLKGLQICGNSIMPLLTFYGNSIADRFPTHAE

QFNQNINSQGYTSATLARRSVDIFQNYVAIALMFGVQAVDLRTYKKTGHYDARACLSPATERLY

SAVRHVVGQKPSSDRPYIWNDNEQGLDEHIARISADIAAGGVIVQAVQDILPCLH

AvPAL Variant No. 116 Polynucleotide Sequence (SEQ ID NO: 13):

(SEQ ID NO: 13)
ATGAAAACCCTGAGTCAGGCACAGAGCAAAACCAGCAGCCAGCAGTTTAGCTTTACCGGCA

ATAGCAGCGCAAATGTGATTATTGGTAATCAGAAACTGACCATCAATGATGTTGTACGTGTT

GCCCGTAATGGCACCCTGGTTAGCCTGACCAATAATACCGATATTCTGCAGGGTATTCAGGC

CAGCTGTGATTATATCAATAATGCAGTTGAAAGCGGTGAACCGATGTATGGTGTTACCAGCG

GTTTTGGTGGTATGGCAAATGTTGTAATTAGCCGTGAACAGGCCAGCGAACTGCAGACCAAT

CTGGTTTGGCACCTGAAAACCGGTGCAGGTAATAAACTGCCGCTGGCAGATGTTCGTGCAGC

AATGCTGCTGCGTGCAAATAGCCACATGCGTGGTGCAAGCGGTATTCGTCTGGAACTGATTA

AACGCATGGAAATCTTTCTGAATGCCGGTGTTACCCCGTATGTTTATGAATTTGGTAGCATTG

GTGCCAGCGGTGATCTGGTTCCGCTGAGCTATATTACCGGTAGCCTGATTGGCCTGGACCCG

AGCTTTAAAGTTGATTTTAATGGCAAAGAAATGGACGCACCGACCGCACTGCGTCAGCTGAA

TCTGAGTCCGCTGACCCTGCTGCCGAAAGAAGGTCTGGCAATGATGAATGGCACCAGCGTTA

TGACCGGTATTGCAGCAAATTGTGTTTATGATACCCAGATTCTGACCGCAATTGCAATGGGT

GTTCATGCACTGGATATTCAGGCACTGAATGGTACAAATCAGAGCTTTCATCCGTTTATCCAT

AACAGCAAACCGCATCCGGGTCAGCTGTGGGCAGCAGATCAGATGATTAGCCTGCTGGCCG

GTAGCCAGCTGGTTCGTGATGAACTGGATGGTAAACATGATTATCGTGATGGTGAACTGATC

CAGGATCGTTATGCGCTGCGTTGTCTGCCGCAGTATCTGGGTCCGATTGTTGATGGTATTAGC

CAGATTGCCAAACAAATCGAAATTGAGATTAACAGCGTTACCGATAACCCGCTGATTGATGT

TGATAATCAGGCAAGCTATCATGGTGGTAATTTTATGGGTCAGTATGTTGGTATGGGTATGG

ATCATCTGCGCTATTATATCGGTCTGCTGGCAAAACATCTGGATGTTACCATTGCACTGCTGG

CATCACCGGAATTTAGCATGGGTCTGCCTCCGAGTCTGGTGGGTAATCGTGAACGTAAAGTT

AATATGGGTCTGAAAGGTCTGCAGATTTGCGGTAATAGCATTATGCCGCTGCTGACCTTTTA

TGGTAATAGTATTGCAGATCGTTTTCCGACCCATGCCGAACAGTTTAACCAGTGCATTAACA

GCCAGGGTTATACCAGCGCAACCCTGGCACGTCGTAGCGTTGATATTTTTCAGAATTATGTT

GCCATTGCCCTGATGTTTGGTGTTCAGGCAGTTGATCTGAGGACCTACAAAAAAACCGGTCA

TTATGATGCACGTGCCTGTCTGTCACCGGCAACCGAACGTCTGTATAGCGCAGTTCGTCATG

TTGTTGGTCAGAAACCGAGCTCAGATCGTCCGTATATTTGGAATGATAATGAACAGGGTCTG

GATGAACATATTGCACGTATTAGTGCAGATATTGCAGCCGGTGGTGTTATTGTTCAGGCCGT

TCAGGACATTCTGCCGTGTCTGCAT

AvPAL Variant No. 116 Polypeptide Sequence (SEQ ID NO: 14):

-continued (SEQ ID NO: 14)
```
MKTLSQAQSKTSSQQFSFTGNSSANVIIGNQKLTINDVVRVARNGTLVSLTNNTDILQGIQASCD
YINNAVESGEPMYGVTSGFGGMANVVISREQASELQTNLVWHLKTGAGNKLPLADVRAAMLL
RANSHMRGASGIRLELIKRMEIFLNAGVTPYVYEFGSIGASGDLVPLSYITGSLIGLDPSFKVDFNG
KEMDAPTALRQLNLSPLTLLPKEGLAMMNGTSVMTGIAANCVYDTQILTAIAMGVHALDIQAL
NGTNQSFHPFIHNSKPHPGQLWAADQMISLLAGSQLVRDELDGKHDYRDGELIQDRYALRCLPQ
YLGPIVDGISQIAKQIEIEINSVTDNPLIDVDNQASYHGGNFMGQYVGMGMDHLRYYIGLLAKHL
DVTIALLASPEFSMGLPPSLVGNRERKVNMGLKGLQICGNSIMPLLTFYGNSIADRFPTHAEQFNQ
CINSQGYTSATLARRSVDIFQNYVAIALMFGVQAVDLRTYKKTGHYDARACLSPATERLYSAVR
HVVGQKPSSDRPYIWNDNEQGLDEHIARISADIAAGGVIVQAVQDILPCLH
```

Expression Vector pCK100900i (SEQ ID NO: 15):

(SEQ ID NO: 15)
```
TGGCCACCATCACCATCACCATTAGGGAAGAGCAGATGGGCAAGCTTGACCTGTGAAGTGA
AAAATGGCGCACATTGTGCGACATTTTTTTTTGAATTCTACGTAAAAAGCAGCCGATACATC
GGCTGCTTTTTTTTTGNNNGAGGTTCCAACTTGTGGTATAATGAAATAAGATCACTCCGGAG
CGTATTTTTTGAGTTATCGAGATTTTCAGGAGCTAAGGAGGAACTAAATGGAGAAAAAAT
CACTGGATATACCACCGTTGATATATCCCAATGGCATCGTAAAGAACATTTTGAGGCATTTC
AGTCAGTTGCTCAATGTACCTATAACCAGACCGTTCAGCTGGATATTACGGCCTTTTTAAAG
ACCGTAAAGAAAATAAGCACAAGTTTTATCCGGCCTTTATTCACATTCTTGCCCGCCTGAT
GAATGCTCATCCGGAGTTCCGTATGGCAATGAAAGACGGTGAGCTGGTGATATGGGATAGT
GTTCACCCTTGTTACACCGTTTTCCATGAGCAAACTGAAACGTTTTCATCGCTCTGGAGTGAA
TACCACGACGATTTCCGGCAGTTTCTACACATATATTCGCAAGATGTGGCGTGTTACGGTGA
AAACCTGGCCTATTTCCCTAAAGGGTTTATTGAGAATATGTTTTTCGTCTCAGCCAATCCCTG
GGTGAGTTTCACCAGTTTTGATTTAAACGTGGCCAATATGGACAACTTCTTCGCCCCCGTTTT
CACCATGGGCAAATATTATACGCAAGGCGACAAGGTGCTGATGCCGCTGGCGATTCAGGTTC
ATCATGCCGTCTGTGATGGCTTCCATGTCGGCAGAATGCTTAATGAATTACAACAGTACTGC
GATGAGTGGCAGGGCGGGGCGTAACTGCAGGAGCTCAAACAGCAGCCTGTATTCAGGCTGC
TTTTTTCGTTTTGGTCTGCGCGTAATCTCTTGCTCTGAAAACGAAAAAACCGCCTTGCAGGGC
GGTTTTTCGAAGGTTCTCTGAGCTACCAACTCTTTGAACCGAGGTAACTGGCTTGGAGGAGC
GCAGTCACCAAAACTTGTCCTTTCAGTTTAGCCTTAACCGGCGCATGACTTCAAGACTAACT
CCTCTAAATCAATTACCAGTGGCTGCTGCCAGTGGTGCTTTTGCATGTCTTTCCGGGTTGGAC
TCAAGACGATAGTTACCGGATAAGGCGCAGCGGTCGGACTGAACGGGGGGTTCGTGCATAC
AGTCCAGCTTGGAGCGAACTGCCTACCCGGAACTGAGTGTCAGGCGTGGAATGAGACAAAC
GCGGCCATAACAGCGGAATGACACCGGTAAACCGAAAGGCAGGAACAGGAGAGCGCACGA
GGGAGCCGCCAGGGGGAAACGCCTGGTATCTTTATAGTCCTGTCGGGTTTCGCCACCACTGA
TTTGAGCGTCAGATTTCGTGATGCTTGTCAGGGGGCGGAGCCTATGGAAAAACGGCTTTGC
CGCGGCCCTCTCACTTCCCTGTTAAGTATCTTCCTGGCATCTTCCAGGAAATCTCCGCCCCGT
TCGTAAGCCATTTCCGCTCGCCGCAGTCGAACGACCGAGCGTAGCGAGTCAGTGAGCGAGG
AAGCGGAATATATCCTGTATCACATATTCTGCTGACGCACCGGTGCAGCCTTTTTTCTCCTGC
CACATGAAGCACTTCACTGACACCCTCATCAGTGAACCACCGCTGGTAGCGGTGGTTTTTTT
AGGCCTATGGCCTTTTTTTTTNTGNNAAACCTTTCGCGGTATGGNATNANAGCGCCCGGAA
GAGAGTCAATTAAGAGGGTGGTGAATGTGAAACCAGTAACGTTATACGATGTCGCAGAGTA
```

-continued

```
TGCCGGTGTCTCTTATCAGACCGTTTCCCGCGTGGTGAACCAGGCCAGCCACGTTTCTGCGA

AAACGCGGGAAAAAGTGGAAGCGGCGATGGCGGAGCTGAATTACATTCCCAACCGCGTGGC

ACAACAACTGGCGGGCAAACAGTCGTTGCTGATTGGCGTTGCCACCTCCAGTCTGGCCCTGC

ACGCGCCGTCGCAAATTGTCGCGGCGATTAAATCTCGCGCCGATCAACTGGGTGCCAGCGTG

GTGGTGTCGATGGTAGAACGAAGCGGCGTCGAAGCCTGTAAAGCGGCGGTGCACAATCTTC

TCGCGCAACGCGTCAGTGGGCTGATCATTAACTATCCGCTGGATGACCAGGATGCCATTGCT

GTGGAAGCTGCCTGCACTAATGTTCCGGCGTTATTTCTTGATGTCTCTGACCAGACACCCATC

AACAGTATTATTTTCTCCCATGAAGACGGTACGCGACTGGGCGTGGAGCATCTGGTCGCATT

GGGTCACCAGCAAATCGCGCTGTTAGCGGGCCCATTAAGTTCTGTCTCGGCGCGTCTGCGTC

TGGCTGGCTGGCATAAATATCTCACTCGCAATCAAATTCAGCCGATAGCGGAACGGGAAGG

CGACTGGAGTGCCATGTCCGGTTTTCAACAAACCATGCAAATGCTGAATGAGGGCATCGTTC

CCACTGCGATGCTGGTTGCCAACGATCAGATGGCGCTGGGCGCAATGCGCGCCATTACCGAG

TCCGGGCTGCGCGTTGGTGCGGACATCTCGGTAGTGGGATACGACGATACCGAAGACAGCT

CATGTTATATCCCGCCGTTAACCACCATCAAACAGGATTTTCGCCTGCTGGGGCAAACCAGC

GTGGACCGCTTGCTGCAACTCTCTCAGGGCCAGGCGGTGAAGGGCAATCAGCTGTTGCCCGT

CTCACTGGTGAAAAGAAAAACCACCCTGGCGCCCAATACGCAAACCGCCTCTCCCCGCGCGT

TGGCCGATTCATTAATGCAGCTGGCACGACAGGTTTCCCGACTGGAAAGCGGGCAGTGAGC

GGTACCCGATAAAAGCGGCTTCCTGACAGGAGGCCGTTTTGTTTCTCGAGTTAATTAAGGCA

GTGAGCGCAACGCAATTAATGTGAGTTAGCTCACTCATTAGGCACCCCAGGCTTTACACTTT

ATGCTTCCGGCTCGTATGTTGTGTGGAATTGTGAGCGGATAACAATTTCACACAGGAAACAG

CTATGACCATGATTACGGATTCACTGGCCGTCGTTTTACAATCTAGAGGCCAGCCTGGCCAT

AAGGAGATATACATATGGGCCATCATCATCATCATCATCATCATCACAGCAGCGGCCAT

ATCGAAGGTCGTCATATGAAAACCCTGAGCCAGGCACAGAGCAAAACCAGCAGCCAGCAGT

TTAGCTTTACCGGCAATAGCAGCGCAAATGTGATTATTGGTAATCAGAAACTGACCATCAAT

GATGTTGCACGTGTTGCCCGTAATGGCACCCTGGTTAGCCTGACCAATAATACCGATATTCT

GCAGGGTATTCAGGCCAGCTGTGATTATATCAATAATGCAGTTGAAAGCGGTGAACCGATTT

ATGGTGTTACCAGCGGTTTTGGTGGTATGGCAAATGTTGCAATTAGCCGTGAACAGGCAAGC

GAACTGCAGACCAATCTGGTTTGGTTTCTGAAAACCGGTGCAGGTAATAAACTGCCGCTGGC

AGATGTTCGTGCAGCAATGCTGCTGCGTGCAAATAGCCACATGCGTGGTGCAAGCGGTATTC

GTCTGGAACTGATTAAACGCATGGAAATCTTTCTGAATGCCGGTGTTACCCCGTATGTTTATG

AATTTGGTAGCATTGGTGCCAGCGGTGATCTGGTTCCGCTGAGCTATATTACCGGTAGCCTG

ATTGGCCTGGACCCGAGCTTTAAAGTTGATTTTAATGGCAAAGAAATGGACGCACCGACCGC

ACTGCGTCAGCTGAATCTGAGTCCGCTGACCCTGCTGCCGAAAGAAGGTCTGGCAATGATGA

ATGGCACCAGCGTTATGACCGGTATTGCAGCAAATTGTGTTTATGATACCCAGATTCTGACC

GCAATTGCAATGGGTGTTCATGCACTGGATATTCAGGCACTGAATGGTACAAATCAGAGCTT

TCATCCGTTTATCCATAACAGCAAACCGCATCCGGGTCAGCTGTGGGCAGCAGATCAGATGA

TTAGCCTGCTGGCCAATAGCCAGCTGGTTCGTGATGAACTGGATGGTAAACATGATTATCGT

GATCATGAACTGATCCAGGATCGTTATAGCCTGCGTTGTCTGCCGCAGTATCTGGGTCCGAT

TGTTGATGGTATTAGCCAGATTGCCAAACAAATCGAAATTGAGATTAACAGCGTTACCGATA

ACCCGCTGATTGATGTTGATAATCAGGCAAGCTATCATGGTGGTAATTTTCTGGGTCAGTAT

GTTGGTATGGGTATGGATCATCTGCGCTATTATATCGGTCTGCTGGCAAAACATCTGGATGTT
```

-continued

```
CAGATTGCACTGCTGGCATCACCGGAATTTAGCAATGGTCTGCCTCCGAGTCTGCTGGGTAA

TCGTGAACGTAAAGTTAATATGGGTCTGAAAGGTCTGCAGATTTGCGGTAATAGCATTATGC

CGCTGCTGACCTTTTATGGTAATAGTATTGCAGATCGTTTTCCGACCCATGCCGAACAGTTTA

ACCAGAATATTAACAGCCAGGGTTATACCAGCGCAACCCTGGCACGTCGTAGCGTTGATATT

TTTCAGAATTATGTTGCCATTGCCCTGATGTTTGGTGTTCAGGCAGTTGATCTGCGTACCTAC

AAAAAAACCGGTCATTATGATGCACGTGCCTGTCTGTCACCGGCAACCGAACGTCTGTATAG

CGCAGTTCGTCATGTTGTTGGTCAGAAACCGACCTCAGATCGTCCGTATATTTGGAATGATA

ATGAACAGGGTCTGGATGAACATATTGCACGTATTAGTGCAGATATTGCAGCCGGTGGTGTT

ATTGTTCAGGCCGTTCAGGACATTCTGCCGTGTCTGCATTAAGGCCAAAC
```

Example 1

TAL Gene Acquisition and Construction of Expression Vectors

A synthetic gene encoding *Anabaena variabilis* phenylalanine ammonia lyase (AvPAL) plasmid DNA optimized for expression in *E. coli* was cloned into the *E. coli* expression vector pET16b to provide pET16b-AvPAL (SEQ ID NO:1). The AvPAL open reading frame (SEQ ID NO:2) was amplified by PCR using the oligonucleotides: PAL-pCK-F and PAL-pCK-R and subcloned into the expression vector pCK100900i (SEQ ID NO:15).

| Primer | Sequence 5' to 3' | SEQ ID NO: |
|---|---|---|
| PAL-pCK-F | CTAGAGGCCAGCCTGGCCATAAGGAGATATACATA TGAAAACCCTGAGCCAGGCAC | SEQ ID NO: 16 |
| PAL-pCK-R | GATGGTGATGGTGGCCAGTTTGGCCTTAATGCAGA CACGGCAGAATG | SEQ ID NO: 17 |

This plasmid construct was transformed into an *E. coli* strain derived from W3110. Directed evolution techniques generally known by those skilled in the art were used to generate libraries of gene variants from this plasmid construct (See e.g., U.S. Pat. No. 8,383,346 and WO2010/144103) and screened to identify variants resistant to both trypsin and chymotrypsin (See, U.S. Prov. Pat. Appln. No. 61/897,932, filed Oct. 31, 2013, incorporated by reference herein, in its entirety). Targeted mutagenesis of WT AvPAL (SEQ ID NO:4) and an evolved variant resistant to proteolytic degradation (SEQ ID NO:6) was performed to generate the F107H variants of these enzymes (SEQ ID NO:8, SEQ ID NO:10, SEQ ID NO:12, and SEQ ID NO:14).

Example 2

Lyophilized Lysates from Shake Flask (SF) Cultures

*E. coli* cultures transformed with plasmids containing PAL variants were plated onto Luria Broth-agar plates with 1% glucose and 30 μg/ml chloramphenicol and grown overnight at 37° C. A single colony from each culture was transferred to 50 ml of Luria Broth with 1% glucose and 30 μg/ml chloramphenicol. The cultures were grown for 18 h at 30° C., 250 rpm, and subcultured approximately 1:10 into 250 ml of Terrific Broth with 30 μg/ml of chloramphenicol, to a final OD600 of 0.2. The cultures were grown 135 minutes at 30° C., 250 rpm, to an OD600 of 0.6-0.8 and induced with 1 mM of IPTG. The cultures were grown for 20 h at 30° C., 250 rpm. Cultures were centrifuged 4000 rpm×10 min. The supernatant was discarded, and the pellets were resuspended in 30 ml of 50 mM sodium phosphate pH 7.0. Cells were pelleted (3500×g for 10 min), resuspended in 35 ml of 50 mM sodium phosphate pH 7.0, and lysed using single pass through a microfluidizer (Optimal), at 110 psi. The lysate was pelleted (10,000×g for 30 min) and the supernatant was frozen and lyophilized to generate a powder containing the expressed enzyme.

Example 3

Demonstration of Initial Tyrosine Ammonia Lyase Activity

Figure 2:
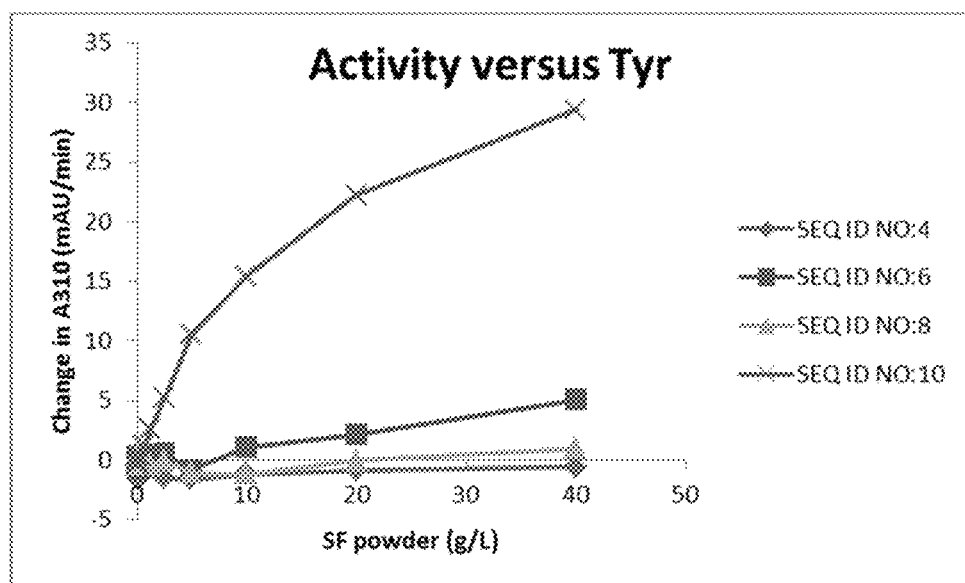
FIG. 2 provides a graph showing the activity of WT AvPAL and AvPAL variants (i.e., TAL variants) on tyrosine.

*E. coli* transformed with plasmids containing SEQ ID NO:3, 5, 7, or 9 were grown in Luria Broth-agar plates with 1% glucose and 30 μg/ml chloramphenicol shake flask cultures and the TAL genes expressed and prepared as described in Example 2. The resulting lyophilized powders were dissolved in buffer, serially diluted, and assayed against 25 mM Phe or 3 mM Tyr in 100 mM sodium phosphate at pH 7.0. The reaction components were mixed briefly and the activity was determined by tracking the absorbance at 290 nm (phenylalanine) or 310 nm (tyrosine) over time (every 12-20s over 5-20 min) using a SpectraMax® Plus$^{384}$ or a SpectraMax® 190 (Molecular Devices) absorbance microplate reader. Variants without the F107H mutation (SEQ ID NOS:4 and 6) each showed significant activity versus phenylalanine, but no detectable activity versus tyrosine. Variants that comprise the F107H mutation (SEQ ID NOS:8 and 10) showed decreased activity versus Phe and detectable activity versus Tyr. The results are shown in FIGS. 1 and 2.

Example 4

High-Throughput (HTP) Growth and Assays

In this Example, methods used for high throughput growth and assays are described.
High-Throughput (HTP) Growth of TAL and TAL Variants:
Transformed *E. coli* cells were selected by plating onto LB agar plates containing 1% glucose and 30 μg/ml chloramphenicol. After overnight incubation at 37° C., colonies were picked onto NUNC™ (Thermo-Scientific) 96-well shallow flat bottom plates filled with 180 μl/well LBmedium supplemented with 1% glucose and 30 µg/ml chloramphenicol. Cultures were allowed to grow overnight for 18-20 hours in a shaker (200 rpm, 30° C., and 85% relative humidity; Kuhner). Overnight growth samples (20 µL) were transferred into Costar 96-well deep plates filled with 380 µL of Terrific Broth supplemented with 30 µg/ml chloramphenicol. Cultures were incubated for 135 minutes in a shaker (250 rpm, 30° C., and 85% relative humidity; Kuhner) and then induced with 40 µL of 10 mM IPTG in sterile water and incubated overnight for 20-24 hours in a shaker (250 rpm, 30° C., and 85% relative humidity; Kuhner). Two replicate cultures were combined, cells were pelleted (4000 rpm×20 min), supernatants were discarded, and cells were frozen at −80° C. prior to analysis.

Lysis of HTP Pellets:

First, 200-225 µL of lysis buffer (B-PER (Pierce), with 1 mg/ml lysozyme) was added to cell pellets. The mixture was agitated for 1 h at room temperature, and pelleted (4000 rpm×10 min) after which the clarified lysates were used in HTP assays. Analysis of these lysates by SDS-PAGE revealed the presence of an overexpressed protein at an apparent MW of 61 kDa consistent with the expected MW of TAL.

In some cases, lysis including B-PER was found to lead to a background signal that interfered with the analysis. In these cases an alternative lysis method was used. In this method, 200 µl of lysis buffer (1 mg/ml lysozyme+0.5 g/L PMBS in 20 mM TRIS pH 7.5) were added to cell pellets. The mixture was agitated for 2 hours at room temperature, and pelleted (4000 rpm×10 min) after which the clarified lysates were used in HTP assays.

Analysis of Clarified Lysates:

TAL variant activity was assayed by measuring the formation of coumaric acid as determined by the change in absorbance at 290 nm over time. Reactions were prepared by the addition of 150-180 µL of 200 mM sodium phosphate, 2.2 mM tyrosine, pH 7.0 and 20-50 µl of clarified lysate to a polyacrylate 96-well plate (Costar #3635, Corning). The reactions were mixed briefly and the activity was determined by tracking the absorbance at 290 nm over time (every 12-60s over 5-120 min) using a SpectraMax® Plus[384] or a SpectraMax® 190 (Molecular Devices) absorbance microplate reader. The results of this assay are shown in Tables 4-1, 4-3, and 4-5.

In certain cases it was found to be beneficial to measure the activity of TAL variants at low tyrosine concentrations (e.g., less than 500 µM, or less than 100 µM). In these cases, the amount of coumarate generated may be below the limit of quantitation for the assay described above. Thus, enzymatic activity must be measured by alternative means. One approach is to monitor absorbance at long time points rather than via the continuous method described above. Reactions were prepared by adding 180 µL of 200 mM sodium phosphate, 0.1-2.5 mM tyrosine, pH 7.0 and 20 µl of clarified lysate to a polyacrylate 96-well plate (Costar #3635, Corning). The reactions were mixed briefly and an initial absorbance was determined by measuring the absorbance at 290 nm using a SpectraMax® Plus[384] or a SpectraMax® 190 (Molecular Devices) absorbance microplate reader. After incubation at 37° C. for 1-5 h with 800 rpm shaking, the final absorbance was measured in a similar fashion. Activity was determined by subtracting the initial from the final absorbance and results are shown in Tables 4.-2, 4-4, and 4-6.

In another assay system, ammonia generated by TAL activity is monitored by a rapid ammonia assay (e.g., the rapid ammonia assay kit available from Megazyme). Briefly, in this assay, 150-180 µl of 200 mM sodium phosphate, 0.01-1 mM tyrosine, pH 7.0 and 20-50 µL of clarified lysate are added to a 96-well polyacrylate plate. After brief mixing, the plate is incubated at 37° C. for 10-600 min. Then, 200 µL of water, 10 µL of sample, 20 µL of Megazyme NADPH solution and 30 µL of Megazyme buffer solution are added to the wells of a NUNC™ (Thermo Scientific) 96 well flat bottom plate. The mixture is agitated for 2 minutes, 2 µL of a GIDH suspension (Megazyme) is added to the reaction, and the absorbance is monitored at 340 nm.

In yet another assay system, production of coumarate is followed using high-performance liquid chromatography (HPLC) as known in the art (See, Geetha et al., Int. J. Phytomed., 3:319-324 [2011]). Reactions conducted as described above are quenched by adding 100 µL of the reaction mix to 100 µL of MeOH and 0.1% formic acid, mixing for 10 min, and centrifuging the samples at 3500×g for 10 min. Chromatography is performed by injecting 50 µL of clarified supernatant onto a Luna 5 µm C18 column (250×4.6 mm) (Phenomenex), at 35° C., and eluting isocratically with 1 ml/min of a 6:4 mixture of methanol:0.8% formic acid in water. Coumarate is detected at 325 nm and elutes at approximately 12.7 min.

TABLE 4-1

Relative Activities of TAL Variants[1,2,3]

| Variant No. | Activity Relative to SEQ ID NO: 10 | Amino Acid Differences Relative to SEQ ID NO: 10 |
|---|---|---|
| 4 | + | G401C |
| 5 | + | S93T |
| 6 | + | D253G |
| 7 | + | S73I |
| 8 | + | G401L |
| 9 | + | Y304F |
| 10 | + | G307P |
| 11 | + | G307H |
| 12 | + | S93R |
| 13 | + | A88S |
| 14 | + | N400M |
| 15 | + | E95D |
| 16 | + | S93L |
| 17 | + | I77M |
| 18 | + | L108C |
| 19 | + | R490T |
| 20 | + | L364M |
| 21 | + | L364H |
| 22 | + | M222T |
| 23 | ++ | A97T |
| 24 | ++ | V91R |
| 25 | ++ | S93P |
| 26 | ++ | N453C |
| 27 | ++ | Q389T |
| 28 | ++ | S315A |

[1]Relative activity was calculated as activity of the variant/activity of SEQ ID NO: 10 (encoded by SEQ ID NO: 9).
[2]Variant No. 17 has the polynucleotide sequence of SEQ ID NO: 11 and polypeptide sequence of SEQ ID NO: 12.
[3]+ = 0.1 to 1.5 relative activity over SEQ ID NO: 10; and ++ = >1.5 to 2.5 relative activity over SEQ ID NO: 10

TABLE 4-2

Relative Activities of TAL Variants (0.1 mM tyrosine)[1,2]

| Variant No. | Activity Relative to SEQ ID NO: 12 | Amino Acid Differences Relative to SEQ ID NO: 10 |
|---|---|---|
| 29 | +++ | I77M/V91R/S93R/A97T/Q389T/N400M |
| 30 | +++ | I77M/A88S/S93L/E95D/A97T/M222T/R490T |
| 31 | ++ | I77M/S315A/L364M/Q389T |
| 32 | ++ | I77M/S315A/N453C/A462T |
| 33 | + | I77M/Q389T |
| 34 | ++ | I77M/L364M/N453C |
| 35 | ++ | I77M/Q389T/N400M |
| 36 | + | I77M/A88S/V91R/S93P/M222T/S315A/L364Y/Q389T/N400T/N453C |
| 37 | + | I77M/M222T/S315A/L364Y/N400M |
| 38 | ++ | I77M/S93W/E95D/A97T/L364M/N453C |
| 39 | +++ | I77M/M222T/S315A/Q389T/N400M |
| 40 | ++ | I77M/E95D |
| 41 | +++ | I77M/S93L/E95D/M222T/N400T |
| 42 | ++ | I77M/S315A/Q389T/N400M |
| 43 | +++ | I77M/S315A/N400T |
| 44 | ++ | I77M/M222T/Q389T |
| 45 | +++ | I77M/S315A/L364M |
| 46 | ++ | I77M/S93W/S315A/L364M |
| 47 | +++ | I77M/S93R/E95D/M222T/S315A/N400M |
| 48 | ++ | I77M/Q389T/N400T |
| 49 | ++ | I77M/S315A/Y367F/N400M/N453C |
| 50 | +++ | I77M/V91R/S93R/E95D/A97T/M222T/N453C |
| 51 | ++ | I77M/L364M/Q389T/N400M |
| 52 | + | I77M/S93L/A97T/N400M/N453C/R490T |
| 53 | ++ | I77M/M222T/L364H |
| 54 | +++ | I77M/S315A/L364M/R490T |
| 55 | + | I77M/S93W/S315A/Q389T |
| 56 | ++ | I77M/S93W/A97T/S315A |
| 57 | ++ | I77M/S93R/E95D/A97T/R490T/P564S |
| 58 | ++ | I77M/S93R/E95D/S315A/L364Y/N453C |
| 59 | + | I77M/M222T/L364M/N400T/N453C |
| 60 | +++ | I77M/M222T/N400T |
| 61 | ++ | I77M/S315A/R490T |
| 62 | ++ | I77M/L364H/N400M/R490T |
| 63 | ++ | I77M/S315A/L364M/Q389T/N453C |
| 64 | ++ | I77M/V91R/S93P/E95D/A97T |
| 65 | ++ | I77M/E95D/Q389T/N400M/N453C |
| 66 | ++ | I77M/S93W/S315A/Q389T/N400T |
| 67 | ++ | I77M/S315A/N400M/N453C |
| 68 | ++ | I77M/L364M/N400T |
| 69 | ++ | I77M/L364M/N400T/R490T |
| 70 | +++ | I77M/M222T/S315A |
| 71 | + | I77M/L108C/S315A/L364M/N400M |
| 72 | ++ | I77M/V91R/S93W/E95D/R490T |
| 73 | + | I77M/S93R/E95D/M222T/L364M/A550V |
| 74 | + | I77M/V91R/S93R/L108C/M222T/S315A/L364Y/N400M |
| 75 | + | I77M/V91R/S93W/E95D/A97T/L108C/M222T/L364M/Q389T |
| 76 | ++ | I77M/V91R/S93L/S315A |
| 77 | +++ | I77M/A88S/S93R/S315A/N400T |
| 78 | +++ | I77M/S315A/Q389T/N400T/N453C |
| 79 | +++ | I77M/S93L/S315A/N400M |
| 80 | ++ | I77M/L364H |
| 81 | +++ | I77M/V91R/S93P/E95D/A97T/S315A/Q389T |
| 82 | ++ | I77M/V91R/S93L/E95D/S315A/L364M/N453C/R490T |
| 83 | ++ | I77M/L364M/Q389T |
| 84 | ++ | I77M/S315A/Q389T |
| 85 | +++ | I77M/S93L/E95D/S315A |
| 86 | + | I77M/L108C/L219M/S315A/Q389T/N400M |
| 87 | ++ | I77M/L364M/R490T |
| 88 | ++ | I77M/V91R/S93L/E95D/S315A/Q389T |
| 89 | ++ | I77M/S93L/E95D/M222T/N400M |
| 90 | +++ | I77M/L108C/M222T/S315A/N400M |
| 91 | + | I77M/N400M/N453C |
| 92 | ++ | I77M/S93P/E95D/S315A/N400M |
| 93 | + | I77M/V91R/S93W/L108C/L364M/Q389T/N400T/N453C |
| 94 | + | I77M/L364M |
| 95 | +++ | I77M/V91R/S93L/M222T/N400M |
| 96 | + | I77M/S93L/S315A/L364M/Q389T/N400T |
| 97 | ++ | I77M/S93P/E95D/L108C/S315A/R490T |
| 98 | +++ | I77M/L108C/M222T/S315A/R490T |
| 99 | + | I77M/A88S/S93L/E95D/M222T/S315A/L364H/N400M |
| 100 | ++ | I77M/M222T |
| 101 | +++ | I77M/S315A/Q389T/N400T |
| 102 | ++ | I77M/S315A/L364M/N453C |

TABLE 4-2-continued

Relative Activities of TAL Variants (0.1 mM tyrosine)[1,2]

| Variant No. | Activity Relative to SEQ ID NO: 12 | Amino Acid Differences Relative to SEQ ID NO: 10 |
|---|---|---|
| 103 | ++ | I77M/V91R/S93L/E95D/A97T |
| 104 | + | I77M/M222T/S315A/N400T/I423F |
| 105 | +++ | I77M/L108C/S315A/N400M/R490T |
| 106 | +++ | I77M/S93R/A97T/S315A |
| 107 | ++ | I77M/V91R/S93R/E95D/S315A/N400M |
| 108 | + | I77M/L364M/Q389T/A394V/N400M |
| 109 | + | I77M/S315A/L364M/N400T/A447T |
| 110 | + | I77M/S93W/N400T |
| 111 | +++ | I77M/M222T/S315A/R490T |
| 112 | + | I77M/A88S/S93L/E95D/A97T/M222T/S315A/L364M/N400T |
| 113 | ++ | I77M/L364H/N400M/R490T |
| 114 | + | I77M/Q389T/N453C |
| 115 | ++ | I77M/N400T |
| 116 | +++ | I77M/S315A/L364M/Q389T/N400M/N453C |
| 117 | ++ | I77M/S315A/L364H/N453C |
| 118 | +++ | I77M/L364H/N400M |
| 119 | +++ | I77M/S315A/L364M/N400M |
| 120 | ++ | I77M/L364M/N400M |
| 121 | ++ | I77M/S315A/N400M/N453C/R490T |
| 122 | ++ | I77M/S315A |
| 123 | + | I77M/L108C/S315A/L364Y/Q389T |
| 124 | + | I77M/A88S/S93W/A97T/L108C/S315A/L364Y/N400T |
| 125 | ++ | I77M/S315A/N453C/R490T |
| 126 | ++ | I77M/E95D/L364M |
| 127 | ++ | I77M/V91R/S93W/E95D/L108C/M222T/R490T |
| 128 | +++ | I77M/L364H/Q389T/N400M/N453C |
| 129 | +++ | I77M/S93L/A97T/S315A/N400M |
| 130 | ++ | I77M/S93W/E95D/A97T/M222T/S315A/L364M/Q389T/N453C |
| 131 | +++ | I77M/E95D/A97T/S315A/N400M |
| 132 | + | I77M/S315A/L364M/Q389T/N400T/R490T |
| 133 | ++ | I77M/E95D/S315A/Q389T/A500S |
| 134 | ++ | I77M/A97T |
| 135 | + | I77M/L108C/S315A/L364M |
| 136 | ++ | I77M/M222T/L364M |
| 137 | + | I77M/R490T |
| 138 | +++ | I77M/M222T/S315A/N400M |
| 139 | ++ | I77M/M222T/Q389T/N453C |
| 140 | + | I77M/V91R/S93R/Q389T |
| 141 | + | I77M/V91R/S93W/A97T/S315A/N453C |
| 142 | + | I77M/N400M |
| 143 | + | I77M/N453C |
| 144 | +++ | I77M/S315A/L364M/Q389T/N400M |
| 145 | +++ | I77M/V91R/S93P/E95D/S315A/N400M |
| 146 | ++ | I77M/E95D/L364H/N400M |
| 147 | ++ | I77M/S93R/L364M/Q389T/N453C |
| 148 | +++ | I77M/E95D/A97T/S315A/Q389T/N400M |
| 149 | ++ | I77M/V91R/S93L/L364M/Q389T/N400M/N453C |
| 150 | +++ | I77M/S315A/N400M |
| 151 | + | I77M/S93W/E95D/A97T/N400M |
| 152 | + | I77M/A88S/E95D/A153V/S315A/P396Q/N400T/N453C |
| 153 | +++ | I77M/V91R/S93L/A97T/S315A/N400M/N453C |
| 154 | + | I77M/L108C/L364M/Q389T/N400T |

[1]Relative activity was calculated as activity of the variant/activity of SEQ ID NO: 12 (encoded by SEQ ID NO: 11).
[2]+ = 0.1 to 1.5 relative activity over SEQ ID NO: 12
++ = > 1.5 to 2.0 relative activity over SEQ ID NO: 12; and
+++ = > 2.0 relative activity over SEQ ID NO: 12

TABLE 4-3

Relative Activities of TAL Variants (2 mM tyrosine)[1,2]

| Variant No. | Activity Relative to SEQ ID NO: 12 | Amino Acid Differences Relative to SEQ ID NO: 10 |
|---|---|---|
| 29 | ++ | I77M/V91R/S93R/A97T/Q389T/N400M |
| 30 | + | I77M/A88S/S93L/E95D/A97T/M222T/R490T |
| 31 | + | I77M/S315A/L364M/Q389T |
| 32 | + | I77M/S315A/N453C/A462T |
| 33 | + | I77M/Q389T |
| 34 | ++ | I77M/L364M/N453C |
| 35 | ++ | I77M/Q389T/N400M |

TABLE 4-3-continued

Relative Activities of TAL Variants (2 mM tyrosine)[1,2]

| Variant No. | Activity Relative to SEQ ID NO: 12 | Amino Acid Differences Relative to SEQ ID NO: 10 |
|---|---|---|
| 36 | − | I77M/A88S/V91R/S93P/M222T/S315A/L364Y/Q389T/N400T/N453C |
| 37 | − | I77M/M222T/S315A/L364Y/N400M |
| 38 | ++ | I77M/S93W/E95D/A97T/L364M/N453C |
| 39 | + | I77M/M222T/S315A/Q389T/N400M |
| 40 | + | I77M/E95D |
| 41 | + | I77M/S93L/E95D/M222T/N400T |
| 42 | + | I77M/S315A/Q389T/N400M |
| 43 | ++ | I77M/S315A/N400T |
| 44 | + | I77M/M222T/Q389T |
| 45 | + | I77M/S315A/L364M |
| 46 | + | I77M/S93W/S315A/L364M |
| 47 | + | I77M/S93R/E95D/M222T/S315A/N400M |
| 48 | + | I77M/Q389T/N400T |
| 49 | ++ | I77M/S315A/Y367F/N400M/N453C |
| 50 | + | I77M/V91R/S93R/E95D/A97T/M222T/N453C |
| 51 | + | I77M/L364M/Q389T/N400M |
| 52 | − | I77M/S93L/A97T/N400M/N453C/R490T |
| 53 | + | I77M/M222T/L364H |
| 54 | + | I77M/S315A/L364M/R490T |
| 55 | + | I77M/S93W/S315A/Q389T |
| 56 | + | I77M/S93W/A97T/S315A |
| 57 | ++ | I77M/S93R/E95D/A97T/R490T/P564S |
| 58 | + | I77M/S93R/E95D/S315A/L364Y/N453C |
| 59 | − | I77M/M222T/L364M/N400T/N453C |
| 60 | + | I77M/M222T/N400T |
| 61 | + | I77M/S315A/R490T |
| 62 | + | I77M/L364H/N400M/R490T |
| 63 | ++ | I77M/S315A/L364M/Q389T/N453C |
| 64 | + | I77M/V91R/S93P/E95D/A97T |
| 65 | ++ | I77M/E95D/Q389T/N400M/N453C |
| 66 | + | I77M/S93W/S315A/Q389T/N400T |
| 67 | ++ | I77M/S315A/N400M/N453C |
| 68 | + | I77M/L364M/N400T |
| 69 | + | I77M/L364M/N400T/R490T |
| 70 | + | I77M/M222T/S315A |
| 71 | − | I77M/L108C/S315A/L364M/N400M |
| 72 | ++ | I77M/V91R/S93W/E95D/R490T |
| 73 | + | I77M/S93R/E95D/M222T/L364M/A550V |
| 74 | − | I77M/V91R/S93R/L108C/M222T/S315A/L364Y/N400M |
| 75 | − | I77M/V91R/S93W/E95D/A97T/L108C/M222T/L364M/Q389T |
| 76 | ++ | I77M/V91R/S93L/S315A |
| 77 | + | I77M/A88S/S93R/S315A/N400T |
| 78 | ++ | I77M/S315A/Q389T/N400T/N453C |
| 79 | ++ | I77M/S93L/S315A/N400M |
| 80 | ++ | I77M/L364H |
| 81 | + | I77M/V91R/S93P/E95D/A97T/S315A/Q389T |
| 82 | + | I77M/V91R/S93L/E95D/S315A/L364M/N453C/R490T |
| 83 | ++ | I77M/L364M/Q389T |
| 84 | ++ | I77M/S315A/Q389T |
| 85 | + | I77M/S93L/E95D/S315A |
| 86 | − | I77M/L108C/L219M/S315A/Q389T/N400M |
| 87 | + | I77M/L364M/R490T |
| 88 | + | I77M/V91R/S93L/E95D/S315A/Q389T |
| 89 | + | I77M/S93L/E95D/M222T/N400M |
| 90 | + | I77M/L108C/M222T/S315A/N400M |
| 91 | ++ | I77M/N400M/N453C |
| 92 | + | I77M/S93P/E95D/S315A/N400M |
| 93 | − | I77M/V91R/S93W/L108C/L364M/Q389T/N400T/N453C |
| 94 | + | I77M/L364M |
| 95 | ++ | I77M/V91R/S93L/M222T/N400M |
| 96 | − | I77M/S93L/S315A/L364M/Q389T/N400T |
| 97 | − | I77M/S93P/E95D/L108C/S315A/R490T |
| 98 | + | I77M/L108C/M222T/S315A/R490T |
| 99 | − | I77M/A88S/S93L/E95D/M222T/S315A/L364H/N400M |
| 100 | + | I77M/M222T |
| 101 | + | I77M/S315A/Q389T/N400T |
| 102 | ++ | I77M/S315A/L364M/N453C |
| 103 | ++ | I77M/V91R/S93L/E95D/A97T |
| 104 | − | I77M/M222T/S315A/N400T/I423F |
| 105 | − | I77M/L108C/S315A/N400M/R490T |
| 106 | + | I77M/S93R/A97T/S315A |
| 107 | + | I77M/V91R/S93R/E95D/S315A/N400M |
| 108 | + | I77M/L364M/Q389T/A394V/N400M |
| 109 | − | I77M/S315A/L364M/N400T/A447T |
| 110 | + | I77M/S93W/N400T |

TABLE 4-3-continued

Relative Activities of TAL Variants (2 mM tyrosine)[1,2]

| Variant No. | Activity Relative to SEQ ID NO: 12 | Amino Acid Differences Relative to SEQ ID NO: 10 |
|---|---|---|
| 111 | + | I77M/M222T/S315A/R490T |
| 112 | − | I77M/A88S/S93L/E95D/A97T/M222T/S315A/L364M/N400T |
| 113 | + | I77M/L364H/N400M/R490T |
| 114 | + | I77M/Q389T/N453C |
| 115 | ++ | I77M/N400T |
| 116 | ++ | I77M/S315A/L364M/Q389T/N400M/N453C |
| 117 | ++ | I77M/S315A/L364H/N453C |
| 118 | ++ | I77M/L364H/N400M |
| 119 | + | I77M/S315A/L364M/N400M |
| 120 | ++ | I77M/L364M/N400M |
| 121 | ++ | I77M/S315A/N400M/N453C/R490T |
| 122 | ++ | I77M/S315A |
| 123 | − | I77M/L108C/S315A/L364Y/Q389T |
| 124 | − | I77M/A88S/S93W/A97T/L108C/S315A/L364Y/N400T |
| 125 | ++ | I77M/S315A/N453C/R490T |
| 126 | ++ | I77M/E95D/L364M |
| 127 | + | I77M/V91R/S93W/E95D/L108C/M222T/R490T |
| 128 | + | I77M/L364H/Q389T/N400M/N453C |
| 129 | + | I77M/S93L/A97T/S315A/N400M |
| 130 | + | I77M/S93W/E95D/A97T/M222T/S315A/L364M/Q389T/N453C |
| 131 | + | I77M/E95D/A97T/S315A/N400M |
| 132 | − | I77M/S315A/L364M/Q389T/N400T/R490T |
| 133 | ++ | I77M/E95D/S315A/Q389T/A500S |
| 134 | + | I77M/A97T |
| 135 | − | I77M/L108C/S315A/L364M |
| 136 | + | I77M/M222T/L364M |
| 137 | ++ | I77M/R490T |
| 138 | + | I77M/M222T/S315A/N400M |
| 139 | ++ | I77M/M222T/Q389T/N453C |
| 140 | + | I77M/V91R/S93R/Q389T |
| 141 | + | I77M/V91R/S93W/A97T/S315A/N453C |
| 142 | + | I77M/N400M |
| 143 | + | I77M/N453C |
| 144 | + | I77M/S315A/L364M/Q389T/N400M |
| 145 | + | I77M/V91R/S93P/E95D/S315A/N400M |
| 146 | + | I77M/E95D/L364H/N400M |
| 147 | ++ | I77M/S93R/L364M/Q389T/N453C |
| 148 | + | I77M/E95D/A97T/S315A/Q389T/N400M |
| 149 | + | I77M/V91R/S93L/L364M/Q389T/N400M/N453C |
| 150 | ++ | I77M/S315A/N400M |
| 151 | + | I77M/S93W/E95D/A97T/N400M |
| 152 | + | I77M/A88S/E95D/A153V/S315A/P396Q/N400T/N453C |
| 153 | ++ | I77M/V91R/S93L/A97T/S315A/N400M/N453C |
| 154 | − | I77M/L108C/L364M/Q389T/N400T |

1 Relative activity was calculated as activity of the variant/activity of SEQ ID NO: 12 (encoded by SEQ ID NO: 11).
2 − = < 0.5 relative activity over SEQ ID NO: 12;
+ = > 0.5 to 1.3 relative activity over SEQ ID NO: 12; and
++ = > 1.3 relative activity over SEQ ID NO: 12.

TABLE 4-4

Relative Activities of TAL Variants (100 uM tyrosine)[1,2]

| Variant No. | Activity Relative to SEQ ID NO: 14 | Amino Acid Differences Relative to SEQ ID NO: 14 |
|---|---|---|
| 155 | + | F18H/L47A/T54K/G59R/L214Q/Q521K |
| 156 | ++ | F18H/L47A/G59R/A97T/L214Q/M364L/C503Q/Q521K |
| 157 | + | F18H/T54K/S73K/C503Q/Q521K/V554I |
| 158 | + | F18H/L47A/T54K/G59R/S73K/Q521K/C565P |
| 159 | + | F18H/L47A/T54K/L214Q/C565P |
| 160 | + | F18H/L47A/G59R/L214Q |
| 161 | + | F18H/L47A/S73K/L214Q/M364L/T389Q/Q521K |
| 162 | ++ | F18H/L47A/S73K/L214Q/T389Q/C503Q |
| 163 | + | F18H/G59R/Q521K |
| 164 | + | F18H/C503Q/C565P |
| 165 | + | L47A/G59R/L214Q/M364L/T389Q/C503Q |
| 166 | + | F18H/G59R/L214Q/C503Q |
| 167 | + | F18H/L47A/L214Q/M364L/T389Q/C503Q/Q521K |
| 168 | + | F18H/G59R/S73K/L214Q/M364L/T389Q |
| 169 | ++ | F18H/L47A/G59R/S73K/A97T/L214Q/M364L/C503Q |

TABLE 4-4-continued

Relative Activities of TAL Variants (100 uM tyrosine)[1,2]

| Variant No. | Activity Relative to SEQ ID NO: 14 | Amino Acid Differences Relative to SEQ ID NO: 14 |
|---|---|---|
| 170 | + | F18H/L47A/S49I/T54K/S73K/A97T/L214Q/M364L |
| 171 | + | F18H/S73K |
| 172 | + | F18H/T54K/G59R/L214Q/C503Q/Q521K |
| 173 | ++ | F18H/L47A/S73K/L214Q/Q521K |
| 174 | + | F18H/S73K/N193D/R305M/C503Q/Q521K |
| 175 | + | F18H/L47A/L214Q/T389Q/Q521K |
| 176 | + | F18H/L47A/M364L/T389Q/Q521K |
| 177 | + | F18H/L214Q/T389Q/C503Q |
| 178 | + | F18H/C503Q |
| 179 | + | F18H/L47A/S73K/L214Q/C565P |
| 180 | + | F18H/L47A/T54K/S73K/L214Q/T389Q/C503Q |
| 181 | + | F18H/L47A/S73K/L214Q/R305M/T389Q |
| 182 | ++ | F18H/L47A/G59R/L214Q/C565P |
| 183 | + | F18H/L47A/T54K/G59R/C64S/S73K/L214Q/T389Q/C503Q |
| 184 | + | F18H/L47A/S73K/L214Q/C503Q/Q521K/C565P |
| 185 | + | F18H/L47A/T54K/G59R/S73K/L214Q/C565P |
| 186 | + | F18H/S73K/C503Q/C565P |
| 187 | + | F18H/S73K/L214Q/T389Q/C503Q/Q521K |
| 188 | + | F18H/L47A/L214Q/M364L/T389Q/C503Q |
| 189 | + | F18H |
| 190 | ++ | F18H/L47A/G59R/S73K/L214Q/C503Q/C565P |
| 191 | + | F18H/L47A/S73K/L214Q/M364L/Q521K/C565P |
| 192 | ++ | F18H/L47A/G59R/S73K/M364L |
| 193 | + | F18H/S73K/L214Q/C503Q/Q521K |
| 194 | + | F18H/L47A/L214Q/C503Q |
| 195 | + | F18H/L47A/T54K/G59R/S73K/L214Q/C503Q |
| 196 | + | F18H/T389Q/Q521K |
| 197 | + | F18H/T54K/L214Q/C503Q |
| 198 | + | F18H/L47A/A97T/L214Q/M364L/C503Q/Q521K/C565P |
| 199 | + | F18H/L47A/S73K/R305M/T389Q/C503Q |
| 200 | + | F18H/L47A/M364L/Q521K |
| 201 | + | F18H/L214Q |
| 202 | + | F18H/G59R/M364L/Q521K |
| 203 | + | F18H/L47A/T54K/G59R/S73K/L214Q/H250N/T389Q |
| 204 | + | F18H/L214Q/C503Q/Q521K |
| 205 | ++ | F18H/L47A/G59R/S73K/A97T/L214Q/M364L/C503Q/Q521K/C565P |
| 206 | + | F18H/T54K/G59R/S73K |
| 207 | + | F18H/L47A/A97T/L214Q/M364L/Q521K |
| 208 | + | F18H/L47A/S73K/R305M/Q521K/C565P |
| 209 | + | F18H/L47A/S73K/L214Q/M364L/C503Q/Q521K |
| 210 | + | F18H/S73K/L214Q/T389Q/C503Q |
| 211 | + | F18H/L47A/T54K |
| 212 | + | F18H/T54K/C503Q/C565P |
| 213 | + | F18H/L47A/C64S/S73K/A97T/L214Q/M364L/C503Q |
| 214 | + | F18H/S73K/C503Q/Q521K |
| 215 | ++ | F18H/L47A/Q521K/C565P |
| 216 | + | F18H/L47A/G59R/L214Q/M364L/C503Q/Q521K |
| 217 | + | F18H/L47A/C503Q/Q521K/C565P |
| 218 | + | F18H/L47A/G59R/L214Q/R305M/T389Q/C503Q/Q521K |
| 219 | + | F18H/L47A/G59R/S73K/L214Q/T389Q/C503Q |
| 220 | + | F18H/L47A/G59R/M364L/C503Q/Q521K/C565P |
| 221 | + | F18H/L47A/G59R/M364L/C503Q/Q521K |
| 222 | + | F18H/L47A/T54K/G59R/S73K/L214Q/C503Q/Q521K/C565P |
| 223 | + | F18H/L47A/S73K/A97T/L214Q/R305M/M364L/Q521K/C565P |
| 224 | + | F18H/S73K/M364L/C565P |
| 225 | + | F18H/L47A |
| 226 | + | F18H/L47A/C64S/S73K/L214Q/M364L/C503Q/C565P |
| 227 | + | F18H/S73K/L214Q/Q521K/C565P |
| 228 | + | F18H/L47A/T54K/S73K/L214Q/L392Q/C503Q/Q521K |
| 229 | + | F18H/L47A/T54K/G59R/S73K/L214Q/M364L/T389Q/C503Q/Q521K |
| 230 | + | F18H/L47A/T54K/G59R/L214Q/M364L/C503Q/C565P |
| 231 | + | F18H/L47A/S73K/L214Q/C503Q/Q521K |
| 232 | + | F18H/L47A/T54K/S73K/A97T/L214Q/M364L/T389Q/C503Q |
| 233 | + | F18H/L47A/L214Q/C503Q/Q521K |
| 234 | + | F18H/L47A/T54K/T389Q |
| 235 | + | F18H/L47A/T54K/L214Q/C503Q/Q521K |
| 236 | + | F18H/T54K/G59R |
| 237 | + | F18H/L47A/G59R/L214Q/M364L/C503Q/C565P |
| 238 | + | F18H/L47A/M364L/T389Q/C565P |
| 239 | + | F18H/T54K/G59R/L214Q/T389Q/Q521K |
| 240 | + | F18H/L47A/S73K/L214Q/T389Q |
| 241 | + | F18H/L47A/T54K/L214Q |
| 242 | + | F18H/L47A/T54K/G59R/S73K/A97T/L214Q/M364L/C503Q |
| 243 | ++ | F18H/L47A/G59R/L214Q/T389Q/C503Q/Q521K/C565P |

TABLE 4-4-continued

Relative Activities of TAL Variants (100 uM tyrosine)[1,2]

| Variant No. | Activity Relative to SEQ ID NO: 14 | Amino Acid Differences Relative to SEQ ID NO: 14 |
|---|---|---|
| 244 | + | F18H/L47A/L214Q/C503Q/Q521K/C565P |
| 245 | + | F18H/L47A/G59R/L214Q/C503Q/Q521K/C565P |
| 246 | + | F18H/L47A/G59R/S73K/L214Q/C503Q |
| 247 | + | G59R |
| 248 | + | F18H/S73K/Q521K/C565P |
| 249 | + | F18H/L47A/T54K/A97T/L214Q/M364L/T389Q/C503Q |
| 250 | + | F18H/L47A/A97T/L214Q/M364L/T389Q/Q521K/C565P |
| 251 | ++ | F18H/L47A/G59R/S73K/T389Q/C565P |
| 252 | + | F18H/L214Q/Q521K |
| 253 | + | F18H/L47A/G59R/S73K/L214Q/M364L/T389Q/C503Q/Q521K/C565P |
| 254 | ++ | F18H/L47A/C64S/S73K/L214Q/Q521K |
| 255 | ++ | F18H/L47A/G59R/S73K/C503Q |
| 256 | + | F18H/G59R/S73K/L214Q/T389Q/C503Q |
| 257 | + | F18H/L47A/T389Q/C503Q |
| 258 | + | F18H/T54K/G59R/S73K/L214Q/M364L/C503Q/Q521K |
| 259 | + | F18H/L47A/S73K/L214Q/T389Q/C503Q/Q521K |
| 260 | + | L214Q/Q521K/C565P |
| 261 | + | F18H/L214Q/M364L/C503Q/Q521K |
| 262 | + | F18H/L47A/G59R/A97T/L214Q/T389Q/C503Q/Q521K/C565P |
| 263 | + | F18H/L47A/M364L/T389Q/C503Q/Q521K/C565P |
| 264 | + | F18H/G59R/L214Q/Q521K |
| 265 | + | F18H/L47A/T54K/S73K/L214Q/M364L/C503Q/C565P |
| 266 | + | L47A/L214Q/M364L |
| 267 | ++ | F18H/G59R/S73K/C503Q |
| 268 | + | F18H/T46N/L47A/S73K/L214Q/M370/C503Q/Q521K |
| 269 | + | F18H/L47A/L214Q/T389Q/C503Q/Q521K |
| 270 | ++ | F18H/L47A/C503Q |
| 271 | + | F18H/L47A/T54K/S73K/L214Q/C503Q/Q521K/C565P |
| 272 | ++ | F18H/L47A/A97T/M364L/Q521K |
| 273 | + | F18H/L47A/S73K/A97T/L214Q/T389Q/C503Q/Q521K |
| 274 | ++ | L47A/G59R/T389Q/C503Q/Q521K/C565P |
| 275 | ++ | F18H/G59R/S73K/L214Q/M364L |
| 276 | + | S73K/L214Q/T389Q/C503Q/Q521K/C565P |
| 277 | + | F18H/L47A/C64S/S73K/C503Q/C565P |
| 278 | ++ | F18H/L47A/G59R/L214Q/M364L |
| 279 | ++ | F18H/L47A/L214Q/M364L/Q521K/C565P |
| 280 | ++ | F18H/G59R/S73K/M364L/C565P |
| 281 | + | L47A/L214Q/C503Q |
| 282 | + | F18H/S73K/L214Q/Q521K |
| 283 | + | F18H/L47A/C64S/S73K/L214Q/T389Q/C503Q/Q521K/C565P |
| 284 | ++ | F18H/L47A/T54K/A97T/M364L/C503Q |
| 285 | + | F18H/L47A/G59R/L214Q/M364L/T389Q/C503Q/Q521K/C565P |
| 286 | ++ | F18H/L47A/S73K/A97T/M364L/C503Q/Q521K |
| 287 | ++ | F18H/L47A/S73K/A97T/L214Q/M364L/C503Q |
| 288 | + | F18H/L47A/T54K/G59R/L214Q/M364L/C503Q |
| 289 | ++ | F18H/L47A/A97T/L214Q/M364L/C503Q |
| 290 | + | Y160P/M372S |
| 291 | + | S175A |
| 292 | + | Y160P/Q336V |
| 293 | + | Y160P |
| 294 | + | V484A |

[1]Relative activity was calculated as activity of the variant/activity of SEQ ID NO: 14 (encoded by SEQ ID NO: 13).
[2]+ = < 1.5 relative activity over SEQ ID NO: 14; and
++ = > 1.5 relative activity over SEQ ID NO: 14.

TABLE 4-5

Relative Activities of TAL Variants (1.3 mM tyrosine)[1,2]

| Variant No. | Activity Relative to SEQ ID NO: 14 | Amino Acid Differences Relative to SEQ ID NO: 14 |
|---|---|---|
| 155 | + | F18H/L47A/T54K/G59R/L214Q/Q521K |
| 156 | ++ | F18H/L47A/G59R/A97T/L214Q/M364L/C503Q/Q521K |
| 157 | + | F18H/T54K/S73K/C503Q/Q521K/V554I |
| 158 | + | F18H/L47A/T54K/G59R/S73K/Q521K/C565P |
| 159 | + | F18H/L47A/T54K/L214Q/C565P |
| 160 | + | F18H/L47A/G59R/L214Q |
| 161 | ++ | F18H/L47A/S73K/L214Q/M364L/T389Q/Q521K |
| 162 | ++ | F18H/L47A/S73K/L214Q/T389Q/C503Q |
| 163 | + | F18H/G59R/Q521K |

TABLE 4-5-continued

Relative Activities of TAL Variants (1.3 mM tyrosine)[1,2]

| Variant No. | Activity Relative to SEQ ID NO: 14 | Amino Acid Differences Relative to SEQ ID NO: 14 |
|---|---|---|
| 164 | + | F18H/C503Q/C565P |
| 165 | + | L47A/G59R/L214Q/M364L/T389Q/C503Q |
| 166 | + | F18H/G59R/L214Q/C503Q |
| 167 | + | F18H/L47A/L214Q/M364L/T389Q/C503Q/Q521K |
| 168 | ++ | F18H/G59R/S73K/L214Q/M364L/T389Q |
| 169 | ++ | F18H/L47A/G59R/S73K/A97T/L214Q/M364L/C503Q |
| 170 | + | F18H/L47A/S49I/T54K/S73K/A97T/L214Q/M364L |
| 171 | + | F18H/S73K |
| 172 | + | F18H/T54K/G59R/L214Q/C503Q/Q521K |
| 173 | + | F18H/L47A/S73K/L214Q/Q521K |
| 174 | + | F18H/S73K/N193D/R305M/C503Q/Q521K |
| 175 | ++ | F18H/L47A/L214Q/T389Q/Q521K |
| 176 | ++ | F18H/L47A/M364L/T389Q/Q521K |
| 177 | + | F18H/L214Q/T389Q/C503Q |
| 178 | + | F18H/C503Q |
| 179 | + | F18H/L47A/S73K/L214Q/C565P |
| 180 | + | F18H/L47A/T54K/S73K/L214Q/T389Q/C503Q |
| 181 | + | F18H/L47A/S73K/L214Q/R305M/T389Q |
| 182 | + | F18H/L47A/G59R/L214Q/C565P |
| 183 | + | F18H/L47A/T54K/G59R/C64S/S73K/L214Q/T389Q/C503Q |
| 184 | + | F18H/L47A/S73K/L214Q/C503Q/Q521K/C565P |
| 185 | + | F18H/L47A/T54K/G59R/S73K/L214Q/C565P |
| 186 | + | F18H/S73K/C503Q/C565P |
| 187 | + | F18H/S73K/L214Q/T389Q/C503Q/Q521K |
| 188 | + | F18H/L47A/L214Q/M364L/T389Q/C503Q |
| 189 | + | F18H |
| 190 | ++ | F18H/L47A/G59R/S73K/L214Q/C503Q/C565P |
| 191 | + | F18H/L47A/S73K/L214Q/M364L/Q521K/C565P |
| 192 | + | F18H/L47A/G59R/S73K/M364L |
| 193 | + | F18H/S73K/L214Q/C503Q/Q521K |
| 194 | + | F18H/L47A/L214Q/C503Q |
| 195 | + | F18H/L47A/T54K/G59R/S73K/L214Q/C503Q |
| 196 | + | F18H/T389Q/Q521K |
| 197 | + | F18H/T54K/L214Q/C503Q |
| 198 | ++ | F18H/L47A/A97T/L214Q/M364L/C503Q/Q521K/C565P |
| 199 | + | F18H/L47A/S73K/R305M/T389Q/C503Q |
| 200 | + | F18H/L47A/M364L/Q521K |
| 201 | + | F18H/L214Q |
| 202 | + | F18H/G59R/M364L/Q521K |
| 203 | + | F18H/L47A/T54K/G59R/S73K/L214Q/H250N/T389Q |
| 204 | + | F18H/L214Q/C503Q/Q521K |
| 205 | + | F18H/L47A/G59R/S73K/A97T/L214Q/M364L/C503Q/Q521K/C565P |
| 206 | + | F18H/T54K/G59R/S73K |
| 207 | + | F18H/L47A/A97T/L214Q/M364L/Q521K |
| 208 | + | F18H/L47A/S73K/R305M/Q521K/C565P |
| 209 | + | F18H/L47A/S73K/L214Q/M364L/C503Q/Q521K |
| 210 | + | F18H/S73K/L214Q/T389Q/C503Q |
| 211 | + | F18H/L47A/T54K |
| 212 | + | F18H/T54K/C503Q/C565P |
| 213 | + | F18H/L47A/C64S/S73K/A97T/L214Q/M364L/C503Q |
| 214 | + | F18H/S73K/C503Q/Q521K |
| 215 | + | F18H/L47A/Q521K/C565P |
| 216 | + | F18H/L47A/G59R/L214Q/M364L/C503Q/Q521K |
| 217 | + | F18H/L47A/C503Q/Q521K/C565P |
| 218 | + | F18H/L47A/G59R/L214Q/R305M/T389Q/C503Q/Q521K |
| 219 | + | F18H/L47A/G59R/S73K/L214Q/T389Q/C503Q |
| 220 | + | F18H/L47A/G59R/M364L/C503Q/Q521K/C565P |
| 221 | + | F18H/L47A/G59R/M364L/C503Q/Q521K |
| 222 | + | F18H/L47A/T54K/G59R/S73K/L214Q/C503Q/Q521K/C565P |
| 223 | + | F18H/L47A/S73K/A97T/L214Q/R305M/M364L/Q521K/C565P |
| 224 | + | F18H/S73K/M364L/C565P |
| 225 | + | F18H/L47A |
| 226 | + | F18H/L47A/C64S/S73K/L214Q/M364L/C503Q/C565P |
| 227 | + | F18H/S73K/L214Q/Q521K/C565P |
| 228 | + | F18H/L47A/T54K/S73K/L214Q/L392Q/C503Q/Q521K |
| 229 | ++ | F18H/L47A/T54K/G59R/S73K/L214Q/M364L/T389Q/C503Q/Q521K |
| 230 | + | F18H/L47A/T54K/G59R/L214Q/M364L/C503Q/C565P |
| 231 | + | F18H/L47A/S73K/L214Q/C503Q/Q521K |
| 232 | ++ | F18H/L47A/T54K/S73K/A97T/L214Q/M364L/T389Q/C503Q |
| 233 | + | F18H/L47A/L214Q/C503Q/Q521K |
| 234 | ++ | F18H/L47A/T54K/T389Q |
| 235 | + | F18H/L47A/T54K/L214Q/C503Q/Q521K |
| 236 | + | F18H/T54K/G59R |
| 237 | ++ | F18H/L47A/G59R/L214Q/M364L/C503Q/C565P |
| 238 | ++ | F18H/L47A/M364L/T389Q/C565P |

TABLE 4-5-continued

Relative Activities of TAL Variants (1.3 mM tyrosine)[1,2]

| Variant No. | Activity Relative to SEQ ID NO: 14 | Amino Acid Differences Relative to SEQ ID NO: 14 |
| --- | --- | --- |
| 239 | + | F18H/T54K/G59R/L214Q/T389Q/Q521K |
| 240 | ++ | F18H/L47A/S73K/L214Q/T389Q |
| 241 | ++ | F18H/L47A/T54K/L214Q |
| 242 | + | F18H/L47A/T54K/G59R/S73K/A97T/L214Q/M364L/C503Q |
| 243 | ++ | F18H/L47A/G59R/L214Q/T389Q/C503Q/Q521K/C565P |
| 244 | ++ | F18H/L47A/L214Q/C503Q/Q521K/C565P |
| 245 | + | F18H/L47A/G59R/L214Q/C503Q/Q521K/C565P |
| 246 | + | F18H/L47A/G59R/S73K/L214Q/C503Q |
| 247 | + | G59R |
| 248 | + | F18H/S73K/Q521K/C565P |
| 249 | ++ | F18H/L47A/T54K/A97T/L214Q/M364L/T389Q/C503Q |
| 250 | ++ | F18H/L47A/A97T/L214Q/M364L/T389Q/Q521K/C565P |
| 251 | + | F18H/L47A/G59R/S73K/T389Q/C565P |
| 252 | + | F18H/L214Q/Q521K |
| 253 | + | F18H/L47A/G59R/S73K/L214Q/M364L/T389Q/C503Q/Q521K/C565P |
| 254 | ++ | F18H/L47A/C64S/S73K/L214Q/Q521K |
| 255 | + | F18H/L47A/G59R/S73K/C503Q |
| 256 | + | F18H/G59R/S73K/L214Q/T389Q/C503Q |
| 257 | ++ | F18H/L47A/T389Q/C503Q |
| 258 | + | F18H/T54K/G59R/S73K/L214Q/M364L/C503Q/Q521K |
| 259 | + | F18H/L47A/S73K/L214Q/T389Q/C503Q/Q521K |
| 260 | + | L214Q/Q521K/C565P |
| 261 | + | F18H/L214Q/M364L/C503Q/Q521K |
| 262 | + | F18H/L47A/G59R/A97T/L214Q/T389Q/C503Q/Q521K/C565P |
| 263 | ++ | F18H/L47A/M364L/T389Q/C503Q/Q521K/C565P |
| 264 | + | F18H/G59R/L214Q/Q521K |
| 265 | + | F18H/L47A/T54K/S73K/L214Q/M364L/C503Q/C565P |
| 266 | + | L47A/L214Q/M364L |
| 267 | + | F18H/G59R/S73K/C503Q |
| 268 | + | F18H/T46N/L47A/S73K/L214Q/M370Q/C503Q/Q521K |
| 269 | ++ | F18H/L47A/L214Q/T389Q/C503Q/Q521K |
| 270 | ++ | F18H/L47A/C503Q |
| 271 | + | F18H/L47A/T54K/S73K/L214Q/C503Q/Q521K/C565P |
| 272 | ++ | F18H/L47A/A97T/M364L/Q521K |
| 273 | + | F18H/L47A/S73K/A97T/L214Q/T389Q/C503Q/Q521K |
| 274 | ++ | L47A/G59R/T389Q/C503Q/Q521K/C565P |
| 275 | ++ | F18H/G59R/S73K/L214Q/M364L |
| 276 | + | S73K/L214Q/T389Q/C503Q/Q521K/C565P |
| 277 | + | F18H/L47A/C64S/S73K/C503Q/C565P |
| 278 | ++ | F18H/L47A/G59R/L214Q/M364L |
| 279 | ++ | F18H/L47A/L214Q/M364L/Q521K/C565P |
| 280 | ++ | F18H/G59R/S73K/M364L/C565P |
| 281 | ++ | L47A/L214Q/C503Q |
| 282 | + | F18H/S73K/L214Q/Q521K |
| 283 | + | F18H/L47A/C64S/S73K/L214Q/T389Q/C503Q/Q521K/C565P |
| 284 | ++ | F18H/L47A/T54K/A97T/M364L/C503Q |
| 285 | ++ | F18H/L47A/G59R/L214Q/M364L/T389Q/C503Q/Q521K/C565P |
| 286 | + | F18H/L47A/S73K/A97T/M364L/C503Q/Q521K |
| 287 | + | F18H/L47A/S73K/A97T/L214Q/M364L/C503Q |
| 288 | + | F18H/L47A/T54K/G59R/L214Q/M364L/C503Q |
| 289 | ++ | F18H/L47A/A97T/L214Q/M364L/C503Q |
| 290 | + | Y160P/M372S |
| 291 | + | S175A |
| 292 | + | Y160P/Q336V |
| 293 | + | Y160P |
| 294 | + | V484A |

[1]Relative activity was calculated as activity of the variant/activity of SEQ ID NO: 14 (encoded by SEQ ID NO: 13).
[2]+ = < 1.5 relative activity over SEQ ID NO: 14; and
++ = > 1.5 relative activity over SEQ ID NO: 14.

TABLE 4-6

Relative Activities of TAL Variants (2.2 mM Phe, 5h) [1,2]

| Variant No. | Activity Relative to SEQ ID NO: 14 | Amino Acid Differences Relative to SEQ ID NO: 14 |
| --- | --- | --- |
| 155 | + | F18H/L47A/T54K/G59R/L214Q/Q521K |
| 156 | ++ | F18H/L47A/G59R/A97T/L214Q/M364L/C503Q/Q521K |
| 157 | + | F18H/T54K/S73K/C503Q/Q521K/V554I |
| 158 | + | F18H/L47A/T54K/G59R/S73K/Q521K/C565P |
| 159 | + | F18H/L47A/T54K/L214Q/C565P |

TABLE 4-6-continued

Relative Activities of TAL Variants (2.2 mM Phe, 5h) [1,2]

| Variant No. | Activity Relative to SEQ ID NO: 14 | Amino Acid Differences Relative to SEQ ID NO: 14 |
|---|---|---|
| 160 | + | F18H/L47A/G59R/L214Q |
| 161 | + | F18H/L47A/S73K/L214Q/M364L/T389Q/Q521K |
| 162 | ++ | F18H/L47A/S73K/L214Q/T389Q/C503Q |
| 163 | + | F18H/G59R/Q521K |
| 164 | + | F18H/C503Q/C565P |
| 165 | + | L47A/G59R/L214Q/M364L/T389Q/C503Q |
| 166 | + | F18H/G59R/L214Q/C503Q |
| 167 | + | F18H/L47A/L214Q/M364L/T389Q/C503Q/Q521K |
| 168 | + | F18H/G59R/S73K/L214Q/M364L/T389Q |
| 169 | ++ | F18H/L47A/G59R/S73K/A97T/L214Q/M364L/C503Q |
| 170 | + | F18H/L47A/S49I/T54K/S73K/A97T/L214Q/M364L |
| 171 | + | F18H/S73K |
| 172 | + | F18H/T54K/G59R/L214Q/C503Q/Q521K |
| 173 | ++ | F18H/L47A/S73K/L214Q/Q521K |
| 174 | + | F18H/S73K/N193D/R305M/C503Q/Q521K |
| 175 | + | F18H/L47A/L214Q/T389Q/Q521K |
| 176 | + | F18H/L47A/M364L/T389Q/Q521K |
| 177 | + | F18H/L214Q/T389Q/C503Q |
| 178 | + | F18H/C503Q |
| 179 | + | F18H/L47A/S73K/L214Q/C565P |
| 180 | + | F18H/L47A/T54K/S73K/L214Q/T389Q/C503Q |
| 181 | + | F18H/L47A/S73K/L214Q/R305M/T389Q |
| 182 | ++ | F18H/L47A/G59R/L214Q/C565P |
| 183 | + | F18H/L47A/T54K/G59R/C64S/S73K/L214Q/T389Q/C503Q |
| 184 | + | F18H/L47A/S73K/L214Q/C503Q/Q521K/C565P |
| 185 | + | F18H/L47A/T54K/G59R/S73K/L214Q/C565P |
| 186 | + | F18H/S73K/C503Q/C565P |
| 187 | + | F18H/S73K/L214Q/T389Q/C503Q/Q521K |
| 188 | + | F18H/L47A/L214Q/M364L/T389Q/C503Q |
| 189 | + | F18H |
| 190 | ++ | F18H/L47A/G59R/S73K/L214Q/C503Q/C565P |
| 191 | + | F18H/L47A/S73K/L214Q/M364L/Q521K/C565P |
| 192 | ++ | F18H/L47A/G59R/S73K/M364L |
| 193 | + | F18H/S73K/L214Q/C503Q/Q521K |
| 194 | + | F18H/L47A/L214Q/C503Q |
| 195 | + | F18H/L47A/T54K/G59R/S73K/L214Q/C503Q |
| 196 | + | F18H/T389Q/Q521K |
| 197 | + | F18H/T54K/L214Q/C503Q |
| 198 | + | F18H/L47A/A97T/L214Q/M364L/C503Q/Q521K/C565P |
| 199 | + | F18H/L47A/S73K/R305M/T389Q/C503Q |
| 200 | + | F18H/L47A/M364L/Q521K |
| 201 | + | F18H/L214Q |
| 202 | + | F18H/G59R/M364L/Q521K |
| 203 | + | F18H/L47A/T54K/G59R/S73K/L214Q/H250N/T389Q |
| 204 | + | F18H/L214Q/C503Q/Q521K |
| 205 | ++ | F18H/L47A/G59R/S73K/A97T/L214Q/M364L/C503Q/Q521K/C565P |
| 206 | + | F18H/T54K/G59R/S73K |
| 207 | + | F18H/L47A/A97T/L214Q/M364L/Q521K |
| 208 | + | F18H/L47A/S73K/R305M/Q521K/C565P |
| 209 | + | F18H/L47A/S73K/L214Q/M364L/C503Q/Q521K |
| 210 | + | F18H/S73K/L214Q/T389Q/C503Q |
| 211 | + | F18H/L47A/T54K |
| 212 | + | F18H/T54K/C503Q/C565P |
| 213 | + | F18H/L47A/C64S/S73K/A97T/L214Q/M364L/C503Q |
| 214 | + | F18H/S73K/C503Q/Q521K |
| 215 | ++ | F18H/L47A/Q521K/C565P |
| 216 | + | F18H/L47A/G59R/L214Q/M364L/C503Q/Q521K |
| 217 | + | F18H/L47A/C503Q/Q521K/C565P |
| 218 | + | F18H/L47A/G59R/L214Q/R305M/T389Q/C503Q/Q521K |
| 219 | + | F18H/L47A/G59R/S73K/L214Q/T389Q/C503Q |
| 220 | + | F18H/L47A/G59R/M364L/C503Q/Q521K/C565P |
| 221 | + | F18H/L47A/G59R/M364L/C503Q/Q521K |
| 222 | + | F18H/L47A/T54K/G59R/S73K/L214Q/C503Q/Q521K/C565P |
| 223 | + | F18H/L47A/S73K/A97T/L214Q/R305M/M364L/Q521K/C565P |
| 224 | + | F18H/S73K/M364L/C565P |
| 225 | + | F18H/L47A |
| 226 | + | F18H/L47A/C64S/S73K/L214Q/M364L/C503Q/C565P |
| 227 | + | F18H/S73K/L214Q/Q521K/C565P |
| 228 | + | F18H/L47A/T54K/S73K/L214Q/L392Q/C503Q/Q521K |
| 229 | + | F18H/L47A/T54K/G59R/S73K/L214Q/M364L/T389Q/C503Q/Q521K |
| 230 | + | F18H/L47A/T54K/G59R/L214Q/M364L/C503Q/C565P |
| 231 | + | F18H/L47A/S73K/L214Q/C503Q/Q521K |
| 232 | + | F18H/L47A/T54K/S73K/A97T/L214Q/M364L/T389Q/C503Q |
| 233 | + | F18H/L47A/L214Q/C503Q/Q521K |
| 234 | + | F18H/L47A/T54K/T389Q |

TABLE 4-6-continued

Relative Activities of TAL Variants (2.2 mM Phe, 5h) [1,2]

| Variant No. | Activity Relative to SEQ ID NO: 14 | Amino Acid Differences Relative to SEQ ID NO: 14 |
|---|---|---|
| 235 | + | F18H/L47A/T54K/L214Q/C503Q/Q521K |
| 236 | + | F18H/T54K/G59R |
| 237 | + | F18H/L47A/G59R/L214Q/M364L/C503Q/C565P |
| 238 | + | F18H/L47A/M364L/T389Q/C565P |
| 239 | + | F18H/T54K/G59R/L214Q/T389Q/Q521K |
| 240 | + | F18H/L47A/S73K/L214Q/T389Q |
| 241 | + | F18H/L47A/T54K/L214Q |
| 242 | + | F18H/L47A/T54K/G59R/S73K/A97T/L214Q/M364L/C503Q |
| 243 | ++ | F18H/L47A/G59R/L214Q/T389Q/C503Q/Q521K/C565P |
| 244 | + | F18H/L47A/L214Q/C503Q/Q521K/C565P |
| 245 | + | F18H/L47A/G59R/L214Q/C503Q/Q521K/C565P |
| 246 | + | F18H/L47A/G59R/S73K/L214Q/C503Q |
| 247 | + | G59R |
| 248 | + | F18H/S73K/Q521K/C565P |
| 249 | + | F18H/L47A/T54K/A97T/L214Q/M364L/T389Q/C503Q |
| 250 | + | F18H/L47A/A97T/L214Q/M364L/T389Q/Q521K/C565P |
| 251 | ++ | F18H/L47A/G59R/S73K/T389Q/C565P |
| 252 | + | F18H/L214Q/Q521K |
| 253 | + | F18H/L47A/G59R/S73K/L214Q/M364L/T389Q/C503Q/Q521K/C565P |
| 254 | ++ | F18H/L47A/C64S/S73K/L214Q/Q521K |
| 255 | ++ | F18H/L47A/G59R/S73K/C503Q |
| 256 | + | F18H/G59R/S73K/L214Q/T389Q/C503Q |
| 257 | + | F18H/L47A/T389Q/C503Q |
| 258 | + | F18H/T54K/G59R/S73K/L214Q/M364L/C503Q/Q521K |
| 259 | + | F18H/L47A/S73K/L214Q/T389Q/C503Q/Q521K |
| 260 | + | L214Q/Q521K/C565P |
| 261 | + | F18H/L214Q/M364L/C503Q/Q521K |
| 262 | + | F18H/L47A/G59R/A97T/L214Q/T389Q/C503Q/Q521K/C565P |
| 263 | + | F18H/L47A/M364L/T389Q/C503Q/Q521K/C565P |
| 264 | + | F18H/G59R/L214Q/Q521K |
| 265 | + | F18H/L47A/T54K/S73K/L214Q/M364L/C503Q/C565P |
| 266 | + | L47A/L214Q/M364L |
| 267 | ++ | F18H/G59R/S73K/C503Q |
| 268 | + | F18H/T46N/L47A/S73K/L214Q/M370Q/C503Q/Q521K |
| 269 | + | F18H/L47A/L214Q/T389Q/C503Q/Q521K |
| 270 | ++ | F18H/L47A/C503Q |
| 271 | + | F18H/L47A/T54K/S73K/L214Q/C503Q/Q521K/C565P |
| 272 | ++ | F18H/L47A/A97T/M364L/Q521K |
| 273 | + | F18H/L47A/S73K/A97T/L214Q/T389Q/C503Q/Q521K |
| 274 | ++ | L47A/G59R/T389Q/C503Q/Q521K/C565P |
| 275 | ++ | F18H/G59R/S73K/L214Q/M364L |
| 276 | + | S73K/L214Q/T389Q/C503Q/Q521K/C565P |
| 277 | + | F18H/L47A/C64S/S73K/C503Q/C565P |
| 278 | ++ | F18H/L47A/G59R/L214Q/M364L |
| 279 | ++ | F18H/L47A/L214Q/M364L/Q521K/C565P |
| 280 | ++ | F18H/G59R/S73K/M364L/C565P |
| 281 | + | L47A/L214Q/C503Q |
| 282 | + | F18H/S73K/L214Q/Q521K |
| 283 | + | F18H/L47A/C64S/S73K/L214Q/T389Q/C503Q/Q521K/C565P |
| 284 | ++ | F18H/L47A/T54K/A97T/M364L/C503Q |
| 285 | + | F18H/L47A/G59R/L214Q/M364L/T389Q/C503Q/Q521K/C565P |
| 286 | ++ | F18H/L47A/S73K/A97T/M364L/C503Q/Q521K |
| 287 | ++ | F18H/L47A/S73K/A97T/L214Q/M364L/C503Q |
| 288 | + | F18H/L47A/T54K/G59R/L214Q/M364L/C503Q |
| 289 | ++ | F18H/L47A/A97T/L214Q/M364L/C503Q |
| 290 | + | Y160P/M372S |
| 291 | + | S175A |
| 292 | + | Y160P/Q336V |
| 293 | + | Y160P |
| 294 | + | V484A |

[1] Relative activity was calculated as activity of the variant/activity of SEQ ID NO: 14 (encoded by SEQ ID NO: 13).
[2] + = < 1.1 relative activity over SEQ ID NO: 14; and
++ = > 1.1 relative activity over SEQ ID NO: 14.

HTP-Analysis of Clarified Lysates Pretreated with Protease:

TAL variants were challenged with chymotrypsin and trypsin to simulate the environment of the lower intestine. First, 30 μL of protease mix (0.01-100 mg/ml chymotrypsin (C4129, Sigma Aldrich), 0.01-100 mg/ml trypsin (T7409, Sigma Aldrich), 1 mM $CaCl_2$, and 1 mM HCl), 30 μL of 0-50 mM sodium taurocholate in 500 mM sodium phosphate pH 7.0, and 90 μL clarified lysate were added to a 96-well round bottom plate (Costar #3798, Corning). The plates were sealed and incubated at 37° C., 400 rpm, 1" throw for 1h prior to analysis. Residual activity was determined by adding 100 uL of sodium phosphate and tyrosine (to final concentrations of 100 mM and 1.3 mM respectively), pH 7.0 and 100 μL of protease treated lysate are added to a polyacrylate 96-well plate (Costar #3635, Corning). The reactions are mixed briefly and the activity is determined as described in "Analysis of Clarified lysate" above. The results of this assay are provided in Table 4-7.

TABLE 4-7

Relative Activities of TAL Variants (1.4 g/L trypsin and chymotrypsin)[1,2]

| Variant No. | Activity Relative to SEQ ID NO: 14 | Amino Acid Differences Relative to SEQ ID NO: 14 |
|---|---|---|
| 155 | + | F18H/L47A/T54K/G59R/L214Q/Q521K |
| 156 | ++ | F18H/L47A/G59R/A97T/L214Q/M364L/C503Q/Q521K |
| 157 | + | F18H/T54K/S73K/C503Q/Q521K/V554I |
| 158 | + | F18H/L47A/T54K/G59R/S73K/Q521K/C565P |
| 159 | + | F18H/L47A/T54K/L214Q/C565P |
| 160 | ++ | F18H/L47A/G59R/L214Q |
| 161 | + | F18H/L47A/S73K/L214Q/M364L/T389Q/Q521K |
| 162 | ++ | F18H/L47A/S73K/L214Q/T389Q/C503Q |
| 163 | + | F18H/G59R/Q521K |
| 164 | + | F18H/C503Q/C565P |
| 165 | ++ | L47A/G59R/L214Q/M364L/T389Q/C503Q |
| 166 | ++ | F18H/G59R/L214Q/C503Q |
| 167 | + | F18H/L47A/L214Q/M364L/T389Q/C503Q/Q521K |
| 168 | ++ | F18H/G59R/S73K/L214Q/M364L/T389Q |
| 169 | ++ | F18H/L47A/G59R/S73K/A97T/L214Q/M364L/C503Q |
| 170 | ++ | F18H/L47A/S49I/T54K/S73K/A97T/L214Q/M364L |
| 171 | ++ | F18H/S73K |
| 172 | + | F18H/T54K/G59R/L214Q/C503Q/Q521K |
| 173 | ++ | F18H/L47A/S73K/L214Q/Q521K |
| 174 | + | F18H/S73K/N193D/R305M/C503Q/Q521K |
| 175 | ++ | F18H/L47A/L214Q/T389Q/Q521K |
| 176 | + | F18H/L47A/M364L/T389Q/Q521K |
| 177 | + | F18H/L214Q/T389Q/C503Q |
| 178 | + | F18H/C503Q |
| 179 | + | F18H/L47A/S73K/L214Q/C565P |
| 180 | + | F18H/L47A/T54K/S73K/L214Q/T389Q/C503Q |
| 181 | + | F18H/L47A/S73K/L214Q/R305M/T389Q |
| 182 | ++ | F18H/L47A/G59R/L214Q/C565P |
| 183 | + | F18H/L47A/T54K/G59R/C64S/S73K/L214Q/T389Q/C503Q |
| 184 | + | F18H/L47A/S73K/L214Q/C503Q/Q521K/C565P |
| 185 | ++ | F18H/L47A/T54K/G59R/S73K/L214Q/C565P |
| 186 | + | F18H/S73K/C503Q/C565P |
| 187 | + | F18H/S73K/L214Q/T389Q/C503Q/Q521K |
| 188 | + | F18H/L47A/L214Q/M364L/T389Q/C503Q |
| 189 | + | F18H |
| 190 | ++ | F18H/L47A/G59R/S73K/L214Q/C503Q/C565P |
| 191 | + | F18H/L47A/S73K/L214Q/M364L/Q521K/C565P |
| 192 | ++ | F18H/L47A/G59R/S73K/M364L |
| 193 | ++ | F18H/S73K/L214Q/C503Q/Q521K |
| 194 | + | F18H/L47A/L214Q/C503Q |
| 195 | ++ | F18H/L47A/T54K/G59R/S73K/L214Q/C503Q |
| 196 | + | F18H/T389Q/Q521K |
| 197 | + | F18H/T54K/L214Q/C503Q |
| 198 | ++ | F18H/L47A/A97T/L214Q/M364L/C503Q/Q521K/C565P |
| 199 | + | F18H/L47A/S73K/R305M/T389Q/C503Q |
| 200 | + | F18H/L47A/M364L/Q521K |
| 201 | + | F18H/L214Q |
| 202 | + | F18H/G59R/M364L/Q521K |
| 203 | + | F18H/L47A/T54K/G59R/S73K/L214Q/H250N/T389Q |
| 204 | + | F18H/L214Q/C503Q/Q521K |
| 205 | ++ | F18H/L47A/G59R/S73K/A97T/L214Q/M364L/C503Q/Q521K/C565P |
| 206 | + | F18H/T54K/G59R/S73K |
| 207 | + | F18H/L47A/A97T/L214Q/M364L/Q521K |
| 208 | + | F18H/L47A/S73K/R305M/Q521K/C565P |
| 209 | + | F18H/L47A/S73K/L214Q/M364L/C503Q/Q521K |
| 210 | + | F18H/S73K/L214Q/T389Q/C503Q |
| 211 | + | F18H/L47A/T54K |
| 212 | + | F18H/T54K/C503Q/C565P |
| 213 | + | F18H/L47A/C64S/S73K/A97T/L214Q/M364L/C503Q |
| 214 | + | F18H/S73K/C503Q/Q521K |
| 215 | ++ | F18H/L47A/Q521K/C565P |
| 216 | + | F18H/L47A/G59R/L214Q/M364L/C503Q/Q521K |
| 217 | ++ | F18H/L47A/C503Q/Q521K/C565P |
| 218 | + | F18H/L47A/G59R/L214Q/R305M/T389Q/C503Q/Q521K |
| 219 | ++ | F18H/L47A/G59R/S73K/L214Q/T389Q/C503Q |
| 220 | + | F18H/L47A/G59R/M364L/C503Q/Q521K/C565P |
| 221 | + | F18H/L47A/G59R/M364L/C503Q/Q521K |
| 222 | + | F18H/L47A/T54K/G59R/S73K/L214Q/C503Q/Q521K/C565P |
| 223 | + | F18H/L47A/S73K/A97T/L214Q/R305M/M364L/Q521K/C565P |
| 224 | + | F18H/S73K/M364L/C565P |
| 225 | ++ | F18H/L47A |
| 226 | + | F18H/L47A/C64S/S73K/L214Q/M364L/C503Q/C565P |
| 227 | + | F18H/S73K/L214Q/Q521K/C565P |
| 228 | + | F18H/L47A/T54K/S73K/L214Q/L392Q/C503Q/Q521K |
| 229 | ++ | F18H/L47A/T54K/G59R/S73K/L214Q/M364L/T389Q/C503Q/Q521K |

TABLE 4-7-continued

Relative Activities of TAL Variants (1.4 g/L trypsin and chymotrypsin)[1,2]

| Variant No. | Activity Relative to SEQ ID NO: 14 | Amino Acid Differences Relative to SEQ ID NO: 14 |
|---|---|---|
| 230 | ++ | F18H/L47A/T54K/G59R/L214Q/M364L/C503Q/C565P |
| 231 | ++ | F18H/L47A/S73K/L214Q/C503Q/Q521K |
| 232 | ++ | F18H/L47A/T54K/S73K/A97T/L214Q/M364L/T389Q/C503Q |
| 233 | ++ | F18H/L47A/L214Q/C503Q/Q521K |
| 234 | ++ | F18H/L47A/T54K/T389Q |
| 235 | ++ | F18H/L47A/T54K/L214Q/C503Q/Q521K |
| 236 | + | F18H/T54K/G59R |
| 237 | ++ | F18H/L47A/G59R/L214Q/M364L/C503Q/C565P |
| 238 | ++ | F18H/L47A/M364L/T389Q/C565P |
| 239 | + | F18H/T54K/G59R/L214Q/T389Q/Q521K |
| 240 | ++ | F18H/L47A/S73K/L214Q/T389Q |
| 241 | ++ | F18H/L47A/T54K/L214Q |
| 242 | ++ | F18H/L47A/T54K/G59R/S73K/A97T/L214Q/M364L/C503Q |
| 243 | ++ | F18H/L47A/G59R/L214Q/T389Q/C503Q/Q521K/C565P |
| 244 | ++ | F18H/L47A/L214Q/C503Q/Q521K/C565P |
| 245 | ++ | F18H/L47A/G59R/L214Q/C503Q/Q521K/C565P |
| 246 | ++ | F18H/L47A/G59R/S73K/L214Q/C503Q |
| 247 | + | G59R |
| 248 | + | F18H/S73K/Q521K/C565P |
| 249 | ++ | F18H/L47A/T54K/A97T/L214Q/M364L/T389Q/C503Q |
| 250 | ++ | F18H/L47A/A97T/L214Q/M364L/T389Q/Q521K/C565P |
| 251 | ++ | F18H/L47A/G59R/S73K/T389Q/C565P |
| 252 | + | F18H/L214Q/Q521K |
| 253 | ++ | F18H/L47A/G59R/S73K/L214Q/M364L/T389Q/C503Q/Q521K/C565P |
| 254 | ++ | F18H/L47A/C64S/S73K/L214Q/Q521K |
| 255 | ++ | F18H/L47A/G59R/S73K/C503Q |
| 256 | ++ | F18H/G59R/S73K/L214Q/T389Q/C503Q |
| 257 | ++ | F18H/L47A/T389Q/C503Q |
| 258 | + | F18H/T54K/G59R/S73K/L214Q/M364L/C503Q/Q521K |
| 259 | ++ | F18H/L47A/S73K/L214Q/T389Q/C503Q/Q521K |
| 260 | + | L214Q/Q521K/C565P |
| 261 | + | F18H/L214Q/M364L/C503Q/Q521K |
| 262 | ++ | F18H/L47A/G59R/A97T/L214Q/T389Q/C503Q/Q521K/C565P |
| 263 | + | F18H/L47A/M364L/T389Q/C503Q/Q521K/C565P |
| 264 | + | F18H/G59R/L214Q/Q521K |
| 265 | + | F18H/L47A/T54K/S73K/L214Q/M364L/C503Q/C565P |
| 266 | + | L47A/L214Q/M364L |
| 267 | ++ | F18H/G59R/S73K/C503Q |
| 268 | ++ | F18H/T46N/L47A/S73K/L214Q/M370Q/C503Q/Q521K |
| 269 | ++ | F18H/L47A/L214Q/T389Q/C503Q/Q521K |
| 270 | ++ | F18H/L47A/C503Q |
| 271 | ++ | F18H/L47A/T54K/S73K/L214Q/C503Q/Q521K/C565P |
| 272 | ++ | F18H/L47A/A97T/M364L/Q521K |
| 273 | + | F18H/L47A/S73K/A97T/L214Q/T389Q/C503Q/Q521K |
| 274 | ++ | L47A/G59R/T389Q/C503Q/Q521K/C565P |
| 275 | ++ | F18H/G59R/S73K/L214Q/M364L |
| 276 | + | S73K/L214Q/T389Q/C503Q/Q521K/C565P |
| 277 | ++ | F18H/L47A/C64S/S73K/C503Q/C565P |
| 278 | ++ | F18H/L47A/G59R/L214Q/M364L |
| 279 | ++ | F18H/L47A/L214Q/M364L/Q521K/C565P |
| 280 | ++ | F18H/G59R/S73K/M364L/C565P |
| 281 | ++ | L47A/L214Q/C503Q |
| 282 | ++ | F18H/S73K/L214Q/Q521K |
| 283 | + | F18H/L47A/C64S/S73K/L214Q/T389Q/C503Q/Q521K/C565P |
| 284 | ++ | F18H/L47A/T54K/A97T/M364L/C503Q |
| 285 | ++ | F18H/L47A/G59R/L214Q/M364L/T389Q/C503Q/Q521K/C565P |
| 286 | ++ | F18H/L47A/S73K/A97T/M364L/C503Q/Q521K |
| 287 | ++ | F18H/L47A/S73K/A97T/L214Q/M364L/C503Q |
| 288 | + | F18H/L47A/T54K/G59R/L214Q/M364L/C503Q |
| 289 | ++ | F18H/L47A/A97T/L214Q/M364L/C503Q |
| 290 | + | Y160P/M372S |
| 291 | + | S175A |
| 292 | + | Y160P/Q336V |
| 293 | + | Y160P |

[1]Relative activity was calculated as activity of the variant/activity of SEQ ID NO: 14 (encoded by SEQ ID NO: 13).
[2]+ = < 1.5 relative activity over SEQ ID NO: 14;
++ = > 1.5 relative activity over SEQ ID NO: 14; and
+++ = > 2 relative activity over SEQ ID NO: 14.

HTP-Analysis of Clarified Lysates Pretreated with Acid:

TAL variants are challenged under acidic conditions to simulate the environment of the stomach. First, 20 μl of 1M sodium citrate (pH 4.05) and 30 μL of water or 50 μL of 400 mM sodium citrate pH 4.05, followed by 50 uL of clarified lysate are added to a 96-well round bottom plate (Costar #3788, Corning). The plate is sealed and incubated at 37° C., 400 rpm, 1" throw for 1h prior to analysis. The acid-treated lysate is clarified by centrifuging the samples (3200× g for 10 min at 4° C.). Then, 100 μL of 200 mM sodium phosphate, 0.01-3 mM tyrosine, 80 μL of 1.0 M sodium phosphate pH 7.0, and 20 μL of acid-treated lysate are added to a poly-acrylate 96-well plate (Costar #3635, Corning). The reactions are mixed briefly, and the activity is determined as described above.

HTP Analysis of Clarified Lysates Pretreated with Pepsin:

TAL variants are challenged with acidic conditions and pepsin to mimic the environment of the stomach. First, 50 μl of 0.01-100 mg/ml pepsin in 400 mM sodium citrate pH 1.5-4, and 50 μL of clarified lysate are added to a 96-well round bottom plate (Costar #3798, Corning. The plate is sealed and incubated at 37° C., 400 rpm, 1" throw for 1-12h prior to analysis.) Then, 100 μl of 200 mM sodium phosphate/50 mM tyrosine pH 7.0, 80 uL of 1M sodium phosphate, and 20 μl of acid-treated lysate are added to a poly-acrylate 96-well plate (Costar #3635, Corning). The reactions are mixed briefly, and the activity is determined as described above.

Example 5

Assays to Determine Protein Aggregation of TAL Variants

Propensity to aggregation is determined using the ProteoStat® Protein Aggregation Assay kit (Enzo) according to the manufacturer's instructions. Briefly, purified TAL at 0-100 μM is mixed with ProteoStat® detection reagent (1:2000) and analyzed via flow cytometry. Samples are assessed for fluorescence consistent with the ProteoStat® aggregation standards as known in the art (See e.g., Bershtein et al., Mol. Cell, 133-144 [2013]).

Example 6

Purification of TAL from Shake Flask Cultures

TAL variants are grown in shake flask cultures as described above. Saturated cultures are pelleted by centrifugation (4000 rpm×20 min) and the cell pellets are stored at −80° C. prior to purification. Cell pellets are thawed at room temperature and resuspended in 25 mM Tris, pH 8 with 130 mM NaCl at 5 mL of buffer/g of cells. Sample slurry is lysed using a microfluidizer with a pressure setting of 110 psi. Lysate is clarified by centrifugation at 10,000 rpm for 1 hour, followed by filtration through 0.2 μm PES (polyethersulfone) filter (Millipore).

After lysis, the resulting lysate is heated at 85° C. for 1.5-2 hours. The lysate is removed from the heat and clarified by centrifugation at 10,000 rpm at 4° C. for 1 hour. The supernatant containing soluble TAL is filtered through a 0.2 μm PES filter prior to loading onto a chromatography column.

The heat-treated, filtered lysate (80-100 mg of total protein) is diluted two-fold using 25 mM Tris, pH 8 with 1.2 M ammonium sulfate. The sample is loaded on to a HiPrep 16/10 Phenyl FF (hi sub) column (GE Healthcare) pre-equilibrated with the 25 mM Tris, pH 8, with 0.6M ammonium sulfate. Following sample loading, the column is washed with three column volumes of the same buffer, followed by a linear gradient of 0.6 M-0 M ammonium sulfate in 25 mM Tris, pH 8 for one column volume. TAL that is tightly bound to the column is eluted using an isocratic flow of 25 mM Tris, pH 8 for three column volumes. Fractions containing active and pure TAL are pooled.

Purified TAL from the phenyl column is buffer-exchanged into 0.5 M Tris, pH 8.5, and concentrated. Concentrated TAL is analyzed by SDS-PAGE and found to be present in a band at ~60 kDa. The purified TAL samples are filtered through a 0.45 μm PES filter and are stored at ~80° C. until ready for use.

Purified TAL from the phenyl column is buffer-exchanged into 0.5 M Tris, pH 8.5 and concentrated. Concentrated TAL is analyzed by SDS-PAGE and found to be present in a band at ~60 kDa. The purified TAL samples are stored at ~80° C. until ready for use.

Example 7

Characterization of Purified TAL and TAL Variants

In this Example, various assays conducted to characterize variant TALs are described.

Tolerance to Acidic pH:

Lyophilized powders of TAL variants produced as described in Example 2 are dissolved at 1-80 g/L in 20 mM sodium phosphate pH 7.0. Then, 50 μl of each of the enzyme solutions are mixed with 50 μL of 400 mM citric acid (pH 1-5.2) or 100 mM sodium phosphate and reactions are incubated at 37° C. for 1 h at 400 rpm (1" throw). Then, 20 μl of the reaction are mixed with 80 μL of 1M sodium phosphate pH 7.0 and 100 μl of 200 mM sodium phosphate/0.01-3 mM tyrosine pH 7.5. The reaction is mixed briefly, and the enzymatic activity is determined, as described in Example 4.

Determination of $K_M$:

To evaluate if the mutations in the TAL variants had altered kinetics, the Michaelis constant and maximum velocity ($V_{max}$) were determined for each. To assay, 20 μl of diluted TAL and 180 μl of 2× serially diluted tyrosine (0-2.48 mM tyrosine in 200 mM Tris, pH 7.0), were added to the wells of a poly-acrylate 96-well plate (Costar #3625, Corning). The reaction was mixed briefly and initial rates were determined by tracking the absorbance at 290 nm over time (every 12-20s over 5-20 min) using a SpectraMax® Plus$^{384}$ or a SpectraMax® 190 (Molecular Devices) absorbance microplate reader. The $V_{max}$ and $K_M$ for each tested TAL variant was determined by fitting the data to a Michaelis-Menten equation using non-linear regression.

Amino Acid Specificity:

Some tyrosine ammonia lysases demonstrate activity against phenylalanine and/or histidine in addition to tyrosine. To evaluate whether the mutations present in the TAL variants alter the specificity of TAL variants, the activities variants for these three amino acids are monitored. First, 100 μL of 0-80 g/L of shake flask powder in 10 mM sodium phosphate pH 7.0, and 100 μL of 50 mM phenylalanine or histidine or 2.5 mM tyrosine in 200 mM sodium phosphate pH 7.0, are added to a polyacrylate 96-well plate (Costar #3635, Corning). The reaction is mixed briefly and initial rates of enzymatic activity are determined as described in Example 4.

Resistance to Porcine and Bovine Proteases:

To evaluate the relative stability of evolved enzymes to representative proteases, porcine trypsin and bovine chymotrypsin (100 mg each) were dissolved in 2 ml of 100 mM sodium phosphate pH 7.0, and serially diluted 2-fold ten times in 1 mM HCl and 1 mM $CaCl_2$. To 15 µl of the protease dilution series was added 15 µL of a solution containing 500 mM sodium phosphate pH 7 and 20 mM sodium taurocholate. Then, 20 µL of diluted TAL was added and the mixtures were incubated at 37° C. for 1 h at 800 rpm (1" throw). After incubation, 180 µl of 2.48 mM tyrosine in 200 mM sodium phosphate, pH 7.0 was added to each well. The reactions were mixed briefly and activity was determined by tracking the absorbance at 290 nm over time (every 12-20s over 5-20 min) using a SpectraMax® Plus$^{384}$ or a SpectraMax® 190 (Molecular Devices) absorbance microplate reader. Protease resistance was calculated as a percentage residual activity against the control (no protease treatment) sample.

Thermostability of Engineered Variants:

Improved thermostability is a valuable trait useful in manufacture and storage of enzyme therapeutics and often occurs as a byproduct of other stabilization efforts. To assess the relative stability of the variants produced during the development of the present invention, the thermostability of the variants was assessed as follows: 75 µl of TAL variants (~5 g/L in 100 mM sodium phosphate pH 7.0) were incubated for 1h at 50-94° C. Samples were cooled to RT and 20 µl was transferred to a poly-acrylate 96-well plate (Costar #3635, Corning) containing 180 µl of 2.48 mM tyrosine in 200 mM sodium phosphate, pH 7.0. The reactions were mixed briefly and activity was determined by tracking the absorbance at 290 nm over time (every 12-20s over 5-20 min) using a SpectraMax® Plus$^{384}$ or a SpectraMax® 190 (Molecular Devices) absorbance microplate reader. The temperature stability was calculated as a percentage residual activity against an unheated control.

Resistance to Human Proteases:

As described above, some evolved TAL variants are first screened against porcine trypsin and bovine chymotrypsin. Some evolved variants are also tested using human enzymes to confirm that they are resistant to the human homologues of the porcine and/or bovine enzymes. TAL variants (0-80 g/L in 100 mM sodium phosphate, pH 7.0) are incubated with human chymotrypsin (Athens Research) 0-80 BTEE units/ml or human trypsin (ProSpec) (0-10,000 BAEE units/ml) at 37° C. for 2 h. First, 100 µL of the reaction mixture, followed by 100 µL of 0-3 mM tyrosine, 100 mM sodium phosphate pH 7.0, are added to a polyacrylate 96-well plate (Costar #3635, Corning). The reaction is mixed briefly and initial rates were determined as described in Example 4.

Resistance to Crude Pancreatic Extract:

The evolved variants are tested against crude porcine pancreatic extract to demonstrate increased resistance to the enzymes present in the extract, as compared to SEQ ID NO:8 or other reference enzyme(s). Shake flask samples of the enzymes are prepared as described in Example 5 are used. The enzymes are provided at 0-80 g/L in 50 mM potassium phosphate pH 6.8) and are mixed 1:1 with porcine pancreatin (4× Sigma-Aldrich) and incubated at 37° C. with shaking (400 rpm, 1" throw) for up to 23 h.

At the chosen time points, a 10 µl aliquot of each reactions is added to 190 µL of 0-3 mM tyrosine, 100 mM sodium phosphate pH 7.0 in a poly-acrylate 96-well plate (Costar #3635). The reaction is mixed briefly and initial rates are determined as described in Example 4.

Example 8

Intestinal Stability of Variant TAL

To assess the stability and activity of TAL variants as they transit through an animal gut, mice are gavaged with purified enzyme variants. Healthy C57Bl/6 mice, 10-12 weeks old and weighing 20-26 g, are maintained in a metabolic cage and fasted for 15h. Water is provided ad libitum. Following the overnight fast, animals are gavaged using a 21-gauge gavage needle with 0.3 ml of 0.5 M Tris-HCl pH 8.5, or TAL variants (purified as described in Example 5) 0-200 mg/ml in 0.5 M Tris-HCl pH 8.5. At 0.5, 2, or 6 h post-gavage, the animals are decapitated, plasma is collected using green-top capillary blood collection tubes (Ram Scientific), and the contents of the stomach, duodenum (~1-8 cm from the stomach), jejunum (~10-18 cm from the stomach), ileum (~8 cm above the cecum), and colon (~5 cm below the cecum) are collected. The weight of these contents is recorded and the contents are stored at −80° C. prior to analysis.

Stomach or intestinal contents are diluted 4× with 100 mM sodium phosphate pH 7.0, mixed briefly, and centrifuged at 14,000 rpm×2 min. The supernatants are transferred to a 350 µL, 0.45 µM, AcroPrep™ Advanced 96-well filter plate (Pall Corp), and particulates are removed via vacuum filtration. The clarified filtrate is assessed for enzymatic activity as described in the previous Examples and for the presence of intact PAL protein by SDS-PAGE.

Example 9

Reduction of Serum Tyr Levels in a Mouse Model of Tyrosinemia

To assess the therapeutic value of TAL variants, a mouse model of Type I tyrosinemia find use. Mice deficient in the fumarylacetoacetate hydrolase (FAH) gene (FAH mice; See, Grompe et al., Genes Dev., 7:2298-2307 [1993]) are maintained on nitisinone from conception until 3 months of age (See, Overturf et al., Hum. Gen. Ther., 9:295-304 [1998]). Nitisinone is removed for 0-6 weeks and tyrosine levels are monitored by periodically collecting serum and analyzing it for tyrosine levels as described in Example 10. Once mice have established a consistent tyrosine profile, TAL variants are evaluated for their ability to impact serum Tyr levels. On the day of treatment, at time 0h, serum is sampled to establish a baseline level for each individual mouse. The mice are gavaged three times with 0.3 ml of 0-100 g/L of BSA or of TAL variants purified as described in Example 7, at times 1h, 3h, and 5h. At 6h, 7h, and 9h, additional serum samples are taken and analyzed for tyrosine levels as described in Example 10.

An alternative to the oral therapeutic approach described above is intraperitoneal injection of the TAL. In this method, FAH mice off of nitisinone are analyzed to establish baseline tyrosine levels. The mice are injected with 0.2 ml of 0-100 g/L TAL variants, and blood is sampled at 1, 2, 4, or 24 h post-injection. Blood samples are analyzed via LC-MS/MS as described in Example 10.

Example 10

Plasma Tyrosine Levels

Mouse plasma collected as described in Example 8 is evaluated to determine the quantity of tyrosine present.

Mouse plasma (50 μL) is combined with 250 μL of acetonitrile containing 0.6 mM of 1-Tyr (Ring D4, i.e., tyrosine isotopically labeled with deuterium). The samples are mixed at RT for 5 min, centrifuged at 3200×g for 10 min at 4° C. and the supernatants are transferred to a plate for sample analysis. For analysis, 10 μL of each sample is injected into an ABSciex 3200 QTRAP® LC/MS/MS (AB Sciex) and samples are analyzed for levels of tyrosine using methods known in the art.

Example 11

Deimmunization of TAL

In this Example, experiments conducted to identify diversity that would remove T-cell epitopes from TAL are described.
Identification of Deimmunizing Diversity:
To identify diversity that would remove T-cell epitopes, computational methods are used to identify TAL epitopes that would be predicted to elicit a T-cell response. In addition, experimental searches for diversity are also conducted, particularly for protein sites that maintain protein activity in an unchallenged assay (e.g., in the assays described in Example 2). Active variants are then analyzed for their effects on immunogenicity.
Computational Identification of Putative T-Cell Epitopes in a Variant TAL:
Putative T-cell epitopes in TAL variants are identified using the Immune Epitope Database (IEDB) tools, as known in the art and proprietary statistical analysis tools (See e.g., iedb.org and Vita et al., Nucl. Acids Res., 38(Database issue):D854-62 [2010]. Epub 2009 Nov. 11]). Each variant is parsed into all possible 15-mer analysis frames where each frame overlaps the last by 14 amino acids. The 15-mer analysis frames are evaluated for immunogenic potential by scoring their 9-mer core regions for predicted binding to eight common class II HLA-DR alleles (DRB1*0101, DRB1*0301, DRB1*0401, DRB1*0701, DRB1*0801, DRB1*1101, DRB1*1301, and DRB1*1501) that collectively cover nearly 95% of the human population (See e.g., Southwood et al., J. Immunol., 160:3363-3373 [1998]), using IEDB recommended methods. Potential T-cell epitope clusters contained within the variant TAL (i.e., sub-regions contained within the variant TAL that have an unusually high potential for immunogenicity) are identified using statistical analysis tools, as known in the art. The identified T-cell epitope clusters are screened against IEDB database of known epitopes, as well as the GenBank protein database.
Design of Demonizing Libraries:
Libraries are designed that use saturation mutagenesis to mutagenize amino acids within the identified T-cell epitopes that are capable or reducing the computed immunogenicity score.
Identification of Deimmunizing Diversity:
Active TAL variants are analyzed for their immunogenicity levels by evaluating their binding to the eight common Class II HLA-DR alleles described above. The total immunogenicity score reflects the overall immunogenicity of the variant (i.e., the higher the score, the greater the immunogenicity). The immunogenic "hit count" indicates the number of 15-mer analysis frames with an unusually high potential for immunogenicity (i.e., the higher the hit count, the greater the immunogenicity). Mutations in the variants that exhibit a lower total immunogenicity score and/or an immunogenic hit count less than that of the reference enzyme (e.g., WT AvPAL and/or Variant No. 8) are considered to be "deimmunizing mutations." All of the deimmunizing mutations are recombined to generate a number of variants that are active and significantly less immunogenic than the starting reference variant TAL.
Construction and Screening of Deimmunizing Libraries:
Combinatorial and saturation mutagenesis libraries designed to incorporate the deimmunizing diversity as described above are constructed by methods known to those skilled in the art, and tested for activity in an unchallenged assay as described in Example 2. Active variants are identified and sequenced.

Example 12

Assay to Determine Immunogenicity of TAL Variants

After biochemical characterization the most-promising TAL variants are screened for their ability to elicit a T-cell response. Any suitable T-cell assay finds use (See e.g., Tangri et al., J. Immunol., 174:3187-3196 2005]) to establish both the number of healthy human donors who respond to the protein and the intensity of that response. Briefly, in some embodiments, blood samples from approximately 50 healthy human donors are selected based on the distribution of HLA allotypes representative of the human population. PBMCs depleted of CD8+ T cells are isolated from the buffy coats of the blood samples and are used as a source of CD4+ T cells and antigen presenting cells (primarily monocytes and dendritic cells). The TAL variants are then added to the mixtures and early-stage T cell responses are measured by both T-cell proliferation (3H-thymidine incorporation) and release of IL-2.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this application is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

What is claimed is:

1. A recombinant polynucleotide encoding a recombinant tyrosine ammonia lyase, wherein said encoded recombinant tyrosine ammonia lyase comprises an amino acid sequence comprising at least 90% sequence identity to SEQ ID NO:14, and wherein said encoded recombinant tyrosine ammonia lyase comprises a mutation at position 18.

2. The recombinant polynucleotide encoding a recombinant tyrosine ammonia lyase of claim 1, wherein said encoded recombinant tyrosine ammonia lyase further comprises at least one additional mutation in at least one position selected from 47, 54, 59, 64, 73, 77, 88, 91, 93, 95, 97, 107, 108, 214, 219, 222, 253, 304, 307, 315, 364, 367, 389, 394, 396, 400, 401, 423, 447, 453, 462, 490, 500, 503, 521, 550, 554, 564, and/or 565, and wherein the positions correspond to SEQ ID NO:14.

3. The recombinant polynucleotide encoding a recombinant tyrosine ammonia lyase of claim 2, wherein said encoded recombinant tyrosine ammonia lyase further comprises at least one mutation in at least one position selected from S73, I77, A88, V91, S93, E95, A97, L108, L219, M222, D253, Y304, G307, S315, L364, Y367, Q389, A394, P396, N400, G401, I423, A447, N453, A462, R490, A500, A550, and/or P564, and wherein the positions correspond to SEQ ID NO:10.

4. The recombinant polynucleotide encoding a recombinant tyrosine ammonia lyase of claim 2, wherein said encoded recombinant tyrosine ammonia lyase further comprises at least one mutation selected from S73I, I77M, A88S, V91R, S93L/P/R/T/W, E95D, A97T, L108C, L219M, M222T, D253G, Y304F, G307P/H, S315A, L364H/M/Y, Y367F, Q389T, A394V, P396Q, N400M/T, G401C/L, I423F, A447T, N453C, A462T, R490T, A500S, A550V, P564S, and wherein the positions correspond to SEQ ID NO:10.

5. The recombinant polynucleotide encoding a recombinant tyrosine ammonia lyase of claim 1, wherein said encoded recombinant tyrosine ammonia lyase further comprises a substitution set selected from F18H/L47A/T54K/G59R/I77M/L214Q/S315A/L364M/Q389T/N400M/N453C/Q521K; F18H/L47A/G59R/I77M/A97T/L214Q/S315A/Q389T/N400M/N453C/C503Q/Q521K; F18H/T54K/S73K/I77M/S315A/L364M/Q389T/N400M/N453C/C503Q/Q521K/V554I; F18H/L47A/T54K/G59R/S73K/I77M/S315A/L364M/Q389T/N400M/N453C/Q521K/

C565P; F18H/L47A/T54K/I77M/L214Q/S315A/L364M/ Q389T/N400M/N453C/C565P; F18H/L47A/G59R/I77M/ L214Q/S315A/L364M/Q389T/N400M/N453C; F18H/ L47A/S73K/I77M/L214Q/S315A/N400M/N453C/Q521K; F18H/L47A/S73K/I77M/L214Q/S315A/L364M/N400M/ N453C/C503Q; F18H/G59R/I77M/S315A/L364M/Q389T/ N400M/N453C/Q521K; F18H/I77M/S315A/L364M/ Q389T/N400M/N453C/C503Q/C565P; F18H/G59R/I77M/ L214Q/S315A/L364M/Q389T/N400M/N453C/C503Q; F18H/L47A/I77M/L214Q/S315A/N400M/N453C/C503Q/ Q521K; F18H/G59R/S73K/I77M/L214Q/S315A/N400M/ N453C; F18H/L47A/G59R/S73K/I77M/A97T/L214Q/ S315A/Q389T/N400M/N453C/C503Q; F18H/L47A/S49I/ T54K/S73K/I77M/A97T/L214Q/S315A/Q389T/N400M/ N453C; F18H/S73K/I77M/S315A/L364M/Q389T/N400M/ N453C; F18H/T54K/G59R/I77M/L214Q/S315A/L364M/ Q389T/N400M/N453C/C503Q/Q521K; F18H/L47A/S73K/ I77M/L214Q/S315A/L364M/Q389T/N400M/N453C/ Q521K; F18H/S73K/I77M/N193D/R305M/S315A/L364M/ Q389T/N400M/N453C/C503Q/Q521K; F18H/L47A/I77M/ L214Q/S315A/L364M/N400M/N453C/Q521K; F18H/ L47A/I77M/S315A/N400M/N453C/Q521K; F18H/I77M/ L214Q/S315A/L364M/N400M/N453C/C503Q; F18H/ I77M/S315A/L364M/Q389T/N400M/N453C/C503Q; F18H/L47A/S73K/I77M/L214Q/S315A/L364M/Q389T/ N400M/N453C/C565P; F18H/L47A/T54K/S73K/I77M/ L214Q/S315A/L364M/N400M/N453C/C503Q; F18H/ L47A/S73K/I77M/L214Q/R305M/S315A/L364M/N400M/ N453C; F18H/L47A/G59R/I77M/L214Q/S315A/L364M/ Q389T/N400M/N453C/C565P; F18H/L47A/T54K/G59R/ C64S/S73K/I77M/L214Q/S315A/L364M/N400M/N453C/ C503Q; F18H/L47A/S73K/I77M/L214Q/S315A/L364M/ Q389T/N400M/N453C/C503Q/Q521K/C565P; F18H/ L47A/T54K/G59R/S73K/I77M/L214Q/S315A/L364M/ Q389T/N400M/N453C/C565P; F18H/S73K/I77M/S315A/ L364M/Q389T/N400M/N453C/C503Q/C565P; F18H/ S73K/I77M/L214Q/S315A/L364M/N400M/N453C/ C503Q/Q521K; F18H/L47A/I77M/L214Q/S315A/N400M/ N453C/C503Q; F18H/I77M/S315A/L364M/Q389T/ N400M/N453C; F18H/L47A/G59R/S73K/I77M/L214Q/ S315A/L364M/Q389T/N400M/N453C/C503Q/C565P; F18H/L47A/S73K/I77M/L214Q/S315A/Q389T/N400M/ N453C/Q521K/C565P; F18H/L47A/G59R/S73K/I77M/ S315A/Q389T/N400M/N453C; F18H/S73K/I77M/L214Q/ S315A/L364M/Q389T/N400M/N453C/C503Q/Q521K; F18H/L47A/I77M/L214Q/S315A/L364M/Q389T/N400M/ N453C/C503Q; F18H/L47A/T54K/G59R/S73K/I77M/ L214Q/S315A/L364M/Q389T/N400M/N453C/C503Q; F18H/I77M/S315A/L364M/N400M/N453C/Q521K; F18H/ T54K/I77M/L214Q/S315A/L364M/Q389T/N400M/ N453C/C503Q; F18H/L47A/I77M/A97T/L214Q/S315A/ Q389T/N400M/N453C/C503Q/Q521K/C565P; F18H/ L47A/S73K/I77M/R305M/S315A/L364M/N400M/N453C/ C503Q; F18H/L47A/I77M/S315A/Q389T/N400M/N453C/ Q521K; F18H/I77M/L214Q/S315A/L364M/Q389T/ N400M/N453C; F18H/G59R/I77M/S315A/Q389T/ N400M/N453C/Q521K; F18H/L47A/T54K/G59R/S73K/ I77M/L214Q/H250N/S315A/L364M/N400M/N453C; F18H/I77M/L214Q/S315A/L364M/Q389T/N400M/ N453C/C503Q/Q521K; F18H/L47A/G59R/S73K/I77M/ A97T/L214Q/S315A/Q389T/N400M/N453C/C503Q/ Q521K/C565P; F18H/T54K/G59R/S73K/I77M/S315A/ L364M/Q389T/N400M/N453C; F18H/L47A/I77M/A97T/ L214Q/S315A/Q389T/N400M/N453C/Q521K; F18H/ L47A/S73K/I77M/R305M/S315A/L364M/Q389T/N400M/ N453C/Q521K/C565P; F18H/L47A/S73K/I77M/L214Q/ S315A/Q389T/N400M/N453C/C503Q/Q521K; F18H/ S73K/I77M/L214Q/S315A/L364M/N400M/N453C/ C503Q; F18H/L47A/T54K/I77M/S315A/L364M/Q389T/ N400M/N453C; F18H/T54K/I77M/S315A/L364M/Q389T/ N400M/N453C/C503Q/C565P; F18H/L47A/C64S/S73K/ I77M/A97T/L214Q/S315A/Q389T/N400M/N453C/ C503Q; F18H/S73K/I77M/S315A/L364M/Q389T/N400M/ N453C/C503Q/Q521K; F18H/L47A/I77M/S315A/L364M/ Q389T/N400M/N453C/Q521K/C565P; F18H/L47A/G59R/ I77M/L214Q/S315A/Q389T/N400M/N453C/C503Q/ Q521K; F18H/L47A/I77M/S315A/L364M/Q389T/N400M/ N453C/C503Q/Q521K/C565P; F18H/L47A/G59R/I77M/ L214Q/R305M/S315A/L364M/N400M/N453C/C503Q/ Q521K; F18H/L47A/G59R/S73K/I77M/L214Q/S315A/ L364M/N400M/N453C/C503Q; F18H/L47A/G59R/I77M/ S315A/Q389T/N400M/N453C/C503Q/Q521K/C565P; F18H/L47A/G59R/I77M/S315A/Q389T/N400M/N453C/ C503Q/Q521K; F18H/L47A/T54K/G59R/S73K/I77M/ L214Q/S315A/L364M/Q389T/N400M/N453C/C503Q/ Q521K/C565P; F18H/L47A/S73K/I77M/A97T/L214Q/ R305M/S315A/Q389T/N400M/N453C/Q521K/C565P; F18H/S73K/I77M/S315A/Q389T/N400M/N453C/C565P; F18H/L47A/I77M/S315A/L364M/Q389T/N400M/N453C; F18H/L47A/C64S/S73K/I77M/L214Q/S315A/Q389T/ N400M/N453C/C503Q/C565P; F18H/S73K/I77M/L214Q/ S315A/L364M/Q389T/N400M/N453C/Q521K/C565P; F18H/L47A/T54K/S73K/I77M/L214Q/S315A/L364M/ Q389T/L392Q/N400M/N453C/C503Q/Q521K; F18H/ L47A/T54K/G59R/S73K/I77M/L214Q/S315A/N400M/ N453C/C503Q/Q521K; F18H/L47A/T54K/G59R/I77M/ L214Q/S315A/Q389T/N400M/N453C/C503Q/C565P; F18H/L47A/S73K/I77M/L214Q/S315A/L364M/Q389T/ N400M/N453C/C503Q/Q521K; F18H/L47A/T54K/S73K/ I77M/A97T/L214Q/S315A/N400M/N453C/C503Q; F18H/ L47A/I77M/L214Q/S315A/L364M/Q389T/N400M/ N453C/C503Q/Q521K; F18H/L47A/T54K/I77M/S315A/ L364M/N400M/N453C; F18H/L47A/T54K/I77M/L214Q/ S315A/L364M/N400M/N453C/C503Q/Q521K; F18H/T54K/G59R/I77M/S315A/L364M/Q389T/N400M/ N453C; F18H/L47A/G59R/I77M/L214Q/S315A/Q389T/ N400M/N453C/C503Q/C565P; F18H/L47A/I77M/S315A/ N400M/N453C/C565P; F18H/T54K/G59R/I77M/L214Q/ S315A/L364M/N400M/N453C/Q521K; F18H/L47A/ S73K/I77M/L214Q/S315A/L364M/N400M/N453C; F18H/ L47A/T54K/I77M/L214Q/S315A/L364M/Q389T/N400M/ N453C; F18H/L47A/T54K/G59R/S73K/I77M/A97T/ L214Q/S315A/Q389T/N400M/N453C/C503Q; F18H/ L47A/G59R/I77M/L214Q/S315A/L364M/N400M/N453C/ C503Q/Q521K/C565P; F18H/L47A/I77M/L214Q/S315A/ L364M/Q389T/N400M/N453C/C503Q/Q521K/C565P; F18H/L47A/G59R/I77M/L214Q/S315A/L364M/Q389T/ N400M/N453C/C503Q/Q521K/C565P; F18H/L47A/G59R/ S73K/I77M/L214Q/S315A/L364M/Q389T/N400M/ N453C/C503Q; F18H/S73K/I77M/S315A/L364M/Q389T/ N400M/N453C/Q521K/C565P; F18H/L47A/T54K/I77M/ A97T/L214Q/S315A/N400M/N453C/C503Q; F18H/L47A/ I77M/A97T/L214Q/S315A/N400M/N453C/Q521K/ C565P; F18H/L47A/G59R/S73K/I77M/S315A/L364M/ N400M/N453C/C565P; F18H/I77M/L214Q/S315A/ L364M/Q389T/N400M/N453C/Q521K; F18H/L47A/ G59R/S73K/I77M/L214Q/S315A/N400M/N453C/C503Q/ Q521K/C565P; F18H/L47A/C64S/S73K/I77M/L214Q/ S315A/L364M/Q389T/N400M/N453C/Q521K; F18H/ L47A/G59R/S73K/I77M/S315A/L364M/Q389T/N400M/ N453C/C503Q; F18H/G59R/S73K/I77M/L214Q/S315A/ L364M/N400M/N453C/C503Q; F18H/L47A/I77M/S315A/ L364M/N400M/N453C/C503Q; F18H/T54K/G59R/S73K/ I77M/L214Q/S315A/Q389T/N400M/N453C/C503Q/

Q521K; F18H/L47A/S73K/I77M/L214Q/S315A/L364M/N400M/N453C/C503Q/Q521K; F18H/I77M/L214Q/S315A/Q389T/N400M/N453C/C503Q/Q521K; F18H/L47A/G59R/I77M/A97T/L214Q/S315A/L364M/N400M/N453C/C503Q/Q521K/C565P; F18H/L47A/I77M/S315A/N400M/N453C/C503Q/Q521K/C565P; F18H/G59R/I77M/L214Q/S315A/L364M/Q389T/N400M/N453C/Q521K; F18H/L47A/T54K/S73K/I77M/L214Q/S315A/Q389T/N400M/N453C/C503Q/C565P; F18H/G59R/S73K/I77M/S315A/L364M/Q389T/N400M/N453C/C503Q; F18H/T46N/L47A/S73K/I77M/L214Q/S315A/L364M/M370Q/Q389T/N400M/N453C/C503Q/Q521K; F18H/L47A/I77M/L214Q/S315A/L364M/N400M/N453C/C503Q/Q521K; F18H/L47A/I77M/S315A/L364M/Q389T/N400M/N453C/C503Q; F18H/L47A/T54K/S73K/I77M/L214Q/S315A/L364M/Q389T/N400M/N453C/C503Q/Q521K/C565P; F18H/L47A/I77M/A97T/S315A/Q389T/N400M/N453C/Q521K; F18H/L47A/S73K/I77M/A97T/L214Q/S315A/L364M/N400M/N453C/C503Q/Q521K; F18H/G59R/S73K/I77M/L214Q/S315A/Q389T/N400M/N453C; F18H/L47A/C64S/S73K/I77M/S315A/L364M/Q389T/N400M/N453C/C503Q/C565P; F18H/L47A/G59R/I77M/L214Q/S315A/Q389T/N400M/N453C; F18H/L47A/I77M/L214Q/S315A/Q389T/N400M/N453C/Q521K/C565P; F18H/G59R/S73K/I77M/S315A/Q389T/N400M/N453C/C565P; F18H/S73K/I77M/L214Q/S315A/L364M/Q389T/N400M/N453C/Q521K; F18H/L47A/C64S/S73K/I77M/L214Q/S315A/L364M/N400M/N453C/C503Q/Q521K/C565P; F18H/L47A/T54K/I77M/A97T/S315A/Q389T/N400M/N453C/C503Q; F18H/L47A/G59R/I77M/L214Q/S315A/N400M/N453C/C503Q/Q521K/C565P; F18H/L47A/S73K/I77M/A97T/S315A/Q389T/N400M/N453C/C503Q/Q521K; F18H/L47A/S73K/I77M/A97T/L214Q/S315A/Q389T/N400M/N453C/C503Q; F18H/L47A/T54K/G59R/I77M/L214Q/S315A/Q389T/N400M/N453C/C503Q; and F18H/L47A/I77M/A97T/L214Q/S315A/Q389T/N400M/N453C/C503Q, and wherein the positions correspond to SEQ ID NO:10.

6. The recombinant polynucleotide of claim 1, wherein said polynucleotide sequence is codon-optimized.

7. An expression vector comprising the recombinant polynucleotide sequence of claim 6.

8. The expression vector of claim 7, wherein said recombinant polynucleotide sequence is operably linked to a control sequence.

9. The expression vector of claim 8, wherein said control sequence is a promoter.

10. The expression vector of claim 9, wherein said promoter is a heterologous promoter.

11. A host cell comprising the expression vector of claim 9.

12. The host cell of claim 11, wherein said host cell is prokaryotic or eukaryotic.

13. The host cell of claim 12, wherein said host cell is *Escherichia coli.*

14. A host cell comprising the expression vector of claim 10.

15. The host cell of claim 14, wherein said host cell is prokaryotic or eukaryotic.

16. The host cell of claim 15, wherein said host cell is *Escherichia coli.*

17. A method of producing a recombinant tyrosine ammonia lyase variant, comprising culturing said host cell of claim 11, under conditions that said recombinant tyrosine ammonia lyase variant encoded by said recombinant polynucleotide is produced.

18. The method of claim 17, further comprising the step of recovering said recombinant tyrosine ammonia lyase variant.

19. The method of claim 18, further comprising the step of purifying said recombinant tyrosine ammonia lyase variant.

20. A method of producing a recombinant tyrosine ammonia lyase variant, comprising culturing said host cell of claim 14, under conditions that said recombinant tyrosine ammonia lyase variant encoded by said recombinant polynucleotide is produced.

21. The method of claim 20, further comprising the step of recovering said recombinant tyrosine ammonia lyase variant.

22. The method of claim 21, further comprising the step of purifying said recombinant tyrosine ammonia lyase variant.

* * * * *